United States Patent [19]
Abbenante et al.

[11] Patent Number: 6,043,357
[45] Date of Patent: Mar. 28, 2000

[54] HIV PROTEASE INHIBITORS

[75] Inventors: John Abbenante, Chelmer; Doug Bergman, Taringa; Ross Brinkworth, Toowong, all of Australia; Robert Dancer, Cambridge, United Kingdom; Bronwyn Garnham, Eagle Heights, Australia; Peter Hunt, Over Cambridgeshire, United Kingdom; David Fairlie, Springwood, Australia; Darren March, St. Lucia, Australia; Jennifer Martin, Indooroopilly, Australia; Robert Reid, Browns Plains, Australia

[73] Assignee: The University of Queensland, Queensland, Australia

[21] Appl. No.: 08/849,599
[22] PCT Filed: Dec. 4, 1995
[86] PCT No.: PCT/AU95/00817
    § 371 Date: Sep. 9, 1997
    § 102(e) Date: Sep. 9, 1997
[87] PCT Pub. No.: WO96/16950
    PCT Pub. Date: Jun. 6, 1996

[30] Foreign Application Priority Data

Dec. 2, 1994 [AU] Australia ................. PM9825

[51] Int. Cl.$^7$ ................................ C07D 245/00
[52] U.S. Cl. ............................................ 540/460
[58] Field of Search ..................... 540/460, 451; 514/183

[56] References Cited

PUBLICATIONS

Swain, et al. "X–ray crystallographic structure of a complex between a synthetic protease of human immunodeficiency virus 1 and a substrate–based hydroxyethylamine inhibitor", *Proc. Natl. Acad. Sci.*, 87:8805–8809 (1990).

Abbenante, et al. "Regioselective Structural and Functional Mimicry of Peptides. Design of Hydrolytically–Stable Cyclic Peptidomimetic Inhibitors of HIV–1 Protease", *J. Am. Chem. Soc.*, 117:10220–10226 (1995).

*Primary Examiner*—Amelia Owens
*Attorney, Agent, or Firm*—Townsend and Townsend and Crew LLP

[57] ABSTRACT

A HIV-1 protease inhibitor which includes a n-terminal cycle (A) or a C-terminal cycle (B) or both cycles (A) and (B) wherein Y is selected from side chains of Asn or Ilc or Val or Glu and alkyl of 1–6 carbon atoms inclusive of linear branched chains as well as cycloalkyl; and X is selected from $(CH_2)_n$ where n=3–6, —CH(OH)—CH(OH)—CH2; CH(CO2H)—CH2—CH2; CH2CONHCHR where R=D or L amino acids and alkyl of 1–6 carbon atoms inclusive of linear or branched chains.

14 Claims, 12 Drawing Sheets

HIV PROTEASE INHIBITORS

This application is a 371 of PCT/AU95/00817 filed Dec. 4, 1995.

FIELD OF THE INVENTION

This invention relates to HIV protease inhibitors.

BACKGROUND OF THE INVENTION

In recent years, the worldwide research focus on the development of anti-HIV drugs has tested the viability of receptor-based drug design and has helped to focus on de novo drug design. The proteinase of the Human Immunodeficiency Virus, HIV-1 protease (Blundell et al., 1990, TIBS 15 425–430; Huff, J., 1991, J. Med. Chem. 34 2305–2314; Darke, P. L. and Huff, J. R., 1994, Adv. Pharm. 25 399–454; Debouck, C., 1992, AIDS Res. & Hum. Retrovir 8 153–164), is a conspicuous example of a receptor for which drug design methodologies have been applied with some success. The rational design of clinically effective inhibitors for this enzyme has remained elusive.

The Human Immunodeficiency Virus (HIV) now infects over 15 million people worldwide, including some 20,000 individuals in Australia. Drugs aimed at treating HIV infection are being rationally developed to target key regulatory proteins that are essential for the replication of HIV. One of these proteins, HIV-1 protease (HIVPR), is an aspartic protease (James, M. N. G. & Sielecki, A. R., 1989, in Biological Macromolecules & Assemblies (Jurnak, F. A. & McPherson, A. M., eds), Wiley, N.Y., Vol. 3, p. 413; Fitzgerald, P. M. & Springer, J. P., 1991, Ann. Rev. Biophys. Chem. 20 299–320) that acts late in the viral replicative cycle by processing polypeptides (Pr160 and Pr50) transcribed from the gag and pol genes. The protease is essential for assembly and maturation of infectious virions but becomes inactivated by a single mutation (Asp25) in the active site, resulting in immature, non-infective virus particles (Kohl et al., supra; Ashorn et al., Proc. Natl. Acad. Sci. U.S.A. 87 7472–7476; Lambert et al., 1992, Antimicrob. Agents. Chemother. 36 982–988). Since inhibitor binding to HIVPR can also prevent infection of immune cells by HIV, the protease is a valid target for chemotherapeutic intervention (Kohl, N. E., 1988, Proc. Natl. Acad. Sci. USA 85 4686–4690; Ashorn et al., supra; Lambert et al., supra). Inhibitors of HIVPR can be expected to be possible treatments for HIV-infections. Indications are that resistance is more difficult to develop against HIVPR inhibitors (Roberts et al., 1990, Science 248 358–631; Craig et al., 1991, Antiviral Res. 16 295–305; Muirhead et al., 1993, 9th Intl. Cong. AIDS (Berlin), Abs PO-B30-2199; Muirhead et al., 1992, Br. J. Clin. Pharm. 34 170–171; Roberts et al., 1992, Biochem. Soc. Trans. 20 513–516) than reverse transcriptase inhibitors (Tomasselli et al., 1992, Chimicaoggi 6–27), but resistance is still proving to be a major problem.

HIVPR is a homo-dimer, consisting of two identically folded 99 amino acid subunits that form a hydrophobic active site cavity. The $C_2$ symmetry of the enzyme is a unique feature among aspartic proteinases. HIVPR is also characterised by two conformationally flexible flaps (one per subunit) which are able to close around the substrate. The three dimensional crystal structures of both recombinant and synthetic HIVPR have been reported for the enzyme as well as enzyme-inhibitor complexes (Tozser et al., 1992, Biochemistry 31 4793–4800; Swain et al., 1990, Proc. Natl. Acad. Sci. USA 87 8805–8809). The major difference between these enzyme conformations is in the location of the flaps and some residues in the hinge region. The amino acids of HIVPR that line the substrate-binding groove, which is 24 Å long by 6–8 Å diameter, are symmetrically disposed around the catalytic residues located near the centre of the active site.

The first approaches to developing inhibitors of HIVPR involved a combination of analogue-based and mechanism-based drug design that focused on the amino acid sequence of substrates for HIVPR. These inhibitors were based on the observed preference for proteolysis of substrates with a scissile hydrophobic-hydrophobic or aromatic-proline peptide bond (Griffiths, J. T., 1992, Biochemistry 31 5193–5200) and were both potent and selective for HIVPR. Aside from optimising the fitting of amino acid side chains into the corresponding binding pockets (Wlodawer, A. & Erickson, J. W., 1993, Ann. Rev. Biochem. 62 543–585 and references therein) that line the substrate-binding groove of HIVPR, inhibitor design must also take into account hydrogen bonding and electrostatic interactions which occur along the binding groove.

Roberts et al., 1992, Biochem. Soc. Trans. 20 513–516; Pharmaprojects AN 017782 9202. PJB Publications Ltd., Richmond, Surrey, U.K.,; Paessens et al., 1993, 9th Intl. Cong. AIDS (Berlin) Abs PO-A25-0591 & PO-A25-0611; Pharmaprojects AN 019149 9212 & AN 020519 9310, PJB Publications Ltd., Richmond, Surrey, U.K.; 206th ACS (Chicago), 1993, MEDI 138; 32nd ICAAC (Anaheim) 1992, Abs 315 & 1501; Getman et al., 1993, J. Med. Chem. 36 288–291; Alteri et al., 1993, Antimicrob. Agents. Chemother. 37 2087–2092; Pharmaprojects AN 020519 9310, PJB Publications Ltd., Richmond, Surrey, Kim et al., 1993, 9th Intl. Cong. AIDS (Berlin) Abs PO-A25-0622; Vacca et al., 1994, Proc. Natl. Acad. Sci. USA 91 4096–4100; Pharmaprojects AN 020180 9307, PJB Publications Ltd., Richmond, Surrey, U.K.; Jadhav et al., 9th Int. Cong. AIDS (Berlin) Abs PO-A25-585; Vacca et al., 9th Int. Cong. AIDS (Berlin) Abs PO-B26-2023; Young et al., 1992, J. Med. Chem. 35 1702–1709; Cohen et al., 1990, J. Med. Chem. 33 883–894; Thiasrivongs et al., August 1994, Proc. 10th Int. Conf. AIDS (Yokohama) Abs 322A; Pharmaprojects AN 018824 9209, PJB Publications Ltd. Richmond, Surrey, U.K.; Kiso et al., 1993, 9th Intl. Cong. AIDS (Berlin) Abs PO-A25-567; 32nd ICAAC (Anheim), 1992, Abs 317–318; Kageyama et al., 1993, Antimicrob. Agents Chemother 37 810–817; Mimoto et al., 1992, Chem. Pharma. Bull 40 2251–2253; Scrip-world Pharmaceutical News, 1992, 1633 p 26; The Blue Sheet, 1993 35 p 8; Pharmaprojects AN 014606 9108, PJB Publications Ltd. Richmond, Surrey, U.K.; Danner et al., 1993, 9th Intl. Cong. AIDS (Berlin) Abs WS-B2606; Kempf et al., 1991, Antimicrob. Agents Chemother 35 2209–2214; Kort et al., 1993, Antimicrob. Agents Chemother 37 115–119.26; Kempf et al., 1992, J. Org. Chem. 57 5692–5700; Kempf et al., 1993, J. Med. Chem. 36 320–330; Erickson et al., 1990, Science 249 527–533; Pharmaprojects AN 018825 9209, PJB Publications Ltd. Richmond, Surrey, U.K.; 8th Intl. Conf. AIDS (Amsterdam), 1992, Abs ThA1507; Melnick et al., 1994, Proc. 207th ACS National Meeting (San Diego) Abs MEDI-20; Reich, S. H. 1994, Proc. of New Advances in Peptidomimetics and Small Molecule Design (Philadelphia); Sheety et al., August 1994, Proc. 10th Int. Conf. AIDS (Yokohama) Abs 321A; Lam et al., 1994, Science 263 380–384; Grzesiek et al., 1994, J. Am. Chem. Soc. 116 1581–2 and Otto et al., August 1994; Proc. 10th Int. Conf. AIDS (Yokohama) Abs 320A describe some of the more established potent inhibitors of HIVPR in vitro. Reference may be made to Smith et al., 1994, Biorganic & Medicinal Chemistry Letters 4 No. 18

2217–2222 which refers to HIV proteases comprising conformationally constrained peptide based hydroxyethylamines with 17 to 19 membered macrocyclic ring systems. These inhibitors all require the decahydroisoquinoline ring at the C terminus and the large size of the ring system does not permit these compounds to specifically mimic the substrate(s) of HIV protease.

All of the inhibitors in the abovementioned references are potent inhibitors of infection of cultured human cells in vitro, although their potency is usually 1–2 orders of magnitude lower in cells than against HIVPR in vitro. This problem is also discussed in Rich et al., 1990, J. Med. Chem. 33 1285; Toth et al., 1990, Int. J. Peptide Protein Res. 36 544–550; Brinkworth et al., 1991, Biochem. Biophys. Res. Comm. 176 241–246 and Majer et al., 1993, Arch. Biochem. Biophys. 304 1–8. Most of these compounds are being or have been investigated by pharmaceutical companies in vitro and in vivo and as prospective anti-viral drugs.

In contrast to reverse transcriptase inhibitors referred to in Tomasselli et al., supra, and Petteway et al., 1991, TiPS 12 28–34; Clercq, E. D., 1987, TiPS 8 339–345 and Field, H. & Goldthorpe, S. E., 1989, TiPS 10 333–337, protease inhibitors are able to block HIV infection in chronically as well as acutely infected cells which is crucial for clinical efficacy (Roberts et al., 1990, supra; Craig et al., 1991, supra; Muirhead et al., 1993, supra; Muirhead et al., 1992, supra and Roberts et al., 1992, supra, for example.

All of the substrate-based protease inhibitors described in the abovementioned references which are potent inhibitors of HIV infection of cultured human cells in vitro suffer as drugs from a combination of pharmacodynamic and pharmacokinetic problems. These problems are also discussed in Field, H. & Goldthorpe, S. E., 1989, TiPS 10 333–337; Kageyama et al., 1992, Antimicrob. Agents Chemother. 36 926–933; Sandstrom, E. & Obert, B. 1993, Drugs 45 637–653 and PALLAS pKalc and PrologP available from Compudrug Chemistry Ltd., Hungary. These problems include:

(i) short serum half lives ($t_{1/2}$) and high susceptibility to hydrolysis by degradative enzymes present in the blood stream, gut and cells;

(ii) poor absorption, low water-solubility and oral bio-availability; and (iii) rapid liver clearance and biliary excretion.

To improve their stability and bioavailability, various synthetic modifications need to be made but if these become too sophisticated, the economic feasibility of drug production can be compromised.

Structural modifications, involving polar ionisable groups that lead to increased gastrointestinal absorption and plasma concentrations of a renin inhibitor (Rosenberg et al., 1981, J. Med. Chem. 34 469–471), are also being made to improve the pharmacological profile of protease inhibitors. This approach is discussed in Flentge et al., 1984, Proc. 206th ACS National Meeting (San Diego), MEDI-35.

A major strategy to reduce pharmacological problems is to develop inhibitors which either structurally or functionally mimic bioactive peptides but have reduced or no peptide character. Few non-peptide inhibitors have been reported to date. Some are described in Debouck, C., 1992, supra; Brinkworth, R. I. & Fairlie, D. P. 1992, Biochem. Biophys. Res. Commun. 188 624–630; Lam et al., 1994, supra; Grzesiek et al., 1994, supra; Otto et al., supra; Tung et al., August 1994, Proc. 10th Int. Conf. AIDS (Yokohama) Abs 426A; DesJairlais et al., 1990, Proc. Nat. Acad. Sci USA 87 6644–664; Rutenber et al., 1993, J. Bio. Chem. 268 15343–15346 and Saito et al., 1984, J. Biol. Chem. 269 10691–10698. This approach is described in Vacca et al., 1994, supra; Pharmaprojects AN 020180 supra; Jadhav et al., 1993, supra; Vacca et al., 9th Int. Cong. AIDS (Berlin) Abs PO-B26-2023; Young et al., 1992, supra; Tucker et al., 1992, supra and Bone et al., supra which refers to decrease in inhibitor size, which might theoretically minimise biliary excretion while at the same time increasing water solubility. However, such an approach has so far met with limited success.

However, from the foregoing, it will be appreciated that prior art HIV-1 protease inhibitors which are mostly peptides or peptide derived in character have suffered from a number of disadvantages which include:

(i) they are subject to proteolysis or hydrolysis by peptidases and therefore do not reach cells infected with HIV-1;

(ii) they do not have a stable receptor-binding configuration insofar as they are capable of many different conformations; or (iii) they are not anti-viral in nature, i.e. they do not prevent viral replication.

SUMMARY OF THE INVENTION

An object of the invention is to provide HIV-1 protease inhibitors that can structurally and functionally mimic the substrates of the enzyme HIV-1 protease and thus alleviate the aforementioned problems of the prior art.

Therefore, the invention provides HIV-1 protease inhibitors that include an N-terminal cycle

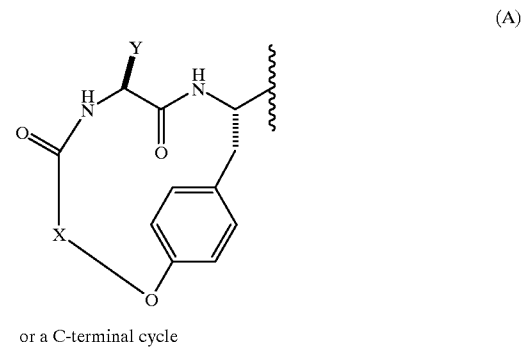

(A)

or a C-terminal cycle

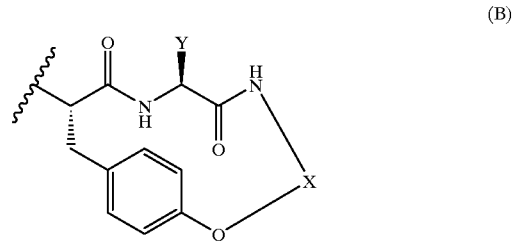

(B)

or both cycles (A) and (B) wherein X and Y are as hereinafter defined.

In regard to structures (A) and (B) above, it will be appreciated that such structures are the same with the exception that the two amide bonds are inverted.

Therefore, the invention includes within its scope, protease inhibitors having the following structures (i), (ii) and (iii) set out hereinbelow which include cycles (A) or (B) or both.

N-Terminus Cyclic Inhibitors (i)

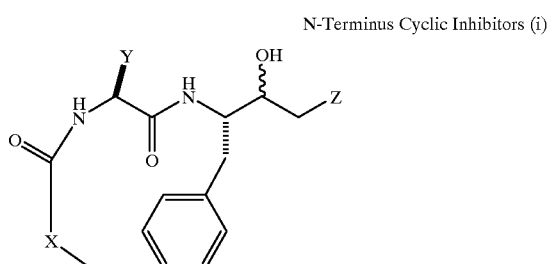

C-Terminus Cyclic Inhibitors (ii)

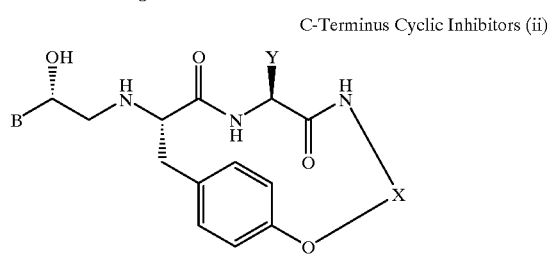

Bicyclic Inhibitors (iii)

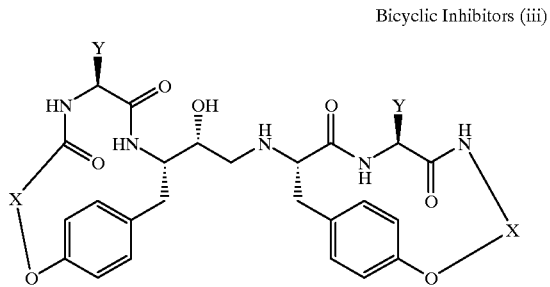

In the structures (i), (ii) and (iii) above,

X=—(CH$_2$)$_n$— where n=3–6 but is preferably 3, 4 or 5, alkyl of 1–6 carbon atoms inclusive of linear and branched chains as well as cycloalkyl —CH(OH)—CH(OH)—CH$_2$—, —CH(CO$_2$H)—CH$_2$—CH$_2$—, or —CH$_2$CONHCHR— where R=D- or L- amino acids and especially Lys, Arg, His, Tyr, Phe, Glu, Gln, Ile, Val or Asp, Y=side chains of Asn or Ile or Val or Glu; or alkyl of 1–6 carbon atoms inclusive of linear and branched chains as well as cycloalkyl

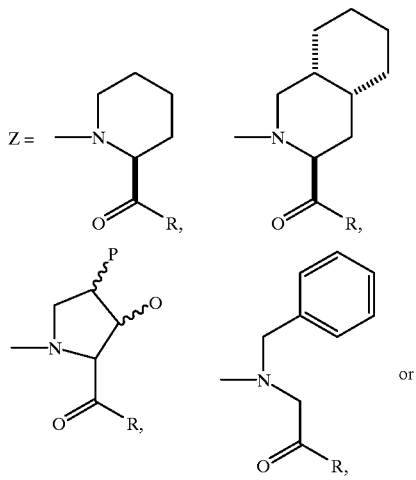

-continued

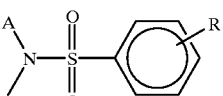

wherein P=H, alkyl, aryl, Oalkyl, Nalkyl

Q=H, alkyl, aryl, Oalkyl, Nalkyl

R$_1$=NHtBu, OtBu, NHiBu, NHiPr, NHnBu, NHnPr, NHalkyl, Oalkyl; or

A=alkyl of 1–6 carbon atoms inclusive of linear or branched structures as well as cycloalkyl; and R=is selected from amino, O-alkyl or N-alkyl

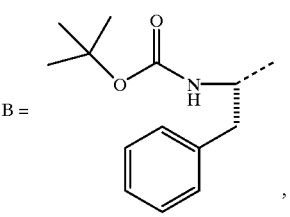

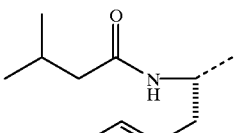

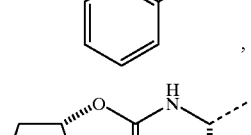

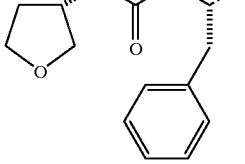

or quinoline—Val-Phe-.

Representative values of branched chain alkyl include isoamyl, isobutyl and isopropyl. Representative values of N-alkyl include NMe$_2$ and O-alkyl includes O—Me. Cycloalkyl may include cyclohexyl or cyclophentyl.

To achieve the objectives of the present invention, we have taken a completely different approach. The X-ray crystal structure is known at 2.2 Å resolution for Ac-Ser-Leu-Asn-Phe-[CHOH—CH$_2$]-Pro-Ile-Val-OMe known as JG-365 bound to HIVPR (Fitzgerald, P. M. & Springer, J. P., 1991, Ann. Rev. Biophys. Biophys. Chem. 20 299–320). Using molecular modelling techniques to visualize this structure, we noticed that alternate amino acid side chains were adjacent and close enough to be linked together. For example, the proximity of Phe and Leu side chains, suggested the possibility of constructing a small macrocycle as a structural replacement for Leu-Asn-Phe in JG-365. Macrocycles have previously been used (McKervey, M. A. & Ye, T., Tetrahedron 48, 37 8007–22) in the construction of renin but these were abandoned as drug leads. Unexpectedly, computer models of these macrocycles superimposed precisely upon linear peptides such as JG-365 and hence this provided a novel method of imitating the structural and functional properties of bioactive peptides. Furthermore, by twisting these peptide sequences into cycles, a surprising result was the cycles were resistant to degradative peptidases. A third benefit was as a result of the stability of the cycles, such cycles showed anti-viral activity whereas peptides such as JG-365 do not have anti-viral activity.

Similarly, cycles can be used to mimic the C-terminal portion fo linear inhibitors such as compounds 87 to 93 in Table 9 hereinafter. In these cases, a C-terminal cycle represents a structural mimic of Phe-Ile-Leu-Val.

By combining the N-terminal cycle with a C-terminal cycle, bicyclic inhibitors can be produced such as compound 111 in Table 11 hereinafter.

FIGS. 11, 12, 13 and 14 show the receptor bound conformations of compounds 3, 87, 134 and 111 (modelled structures overlid on receptor bound conformation of JG-365 (x-ray structure).

Figure 13:
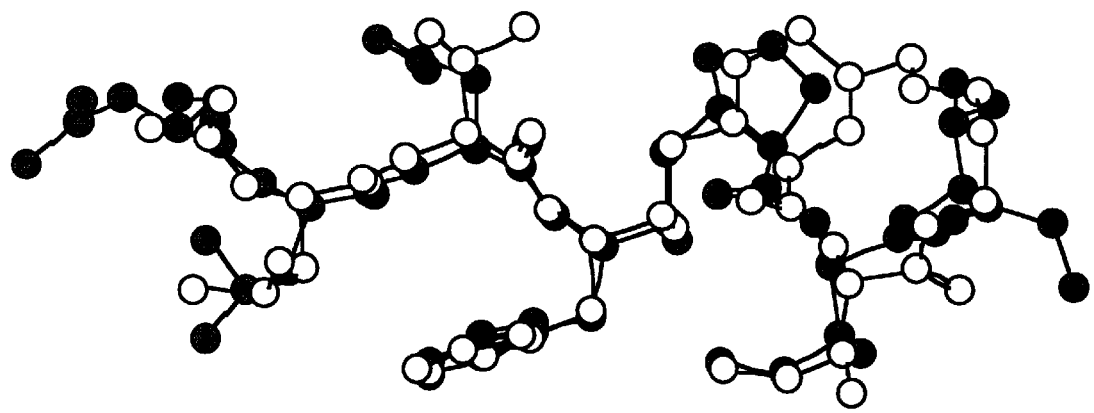
Figure 14:
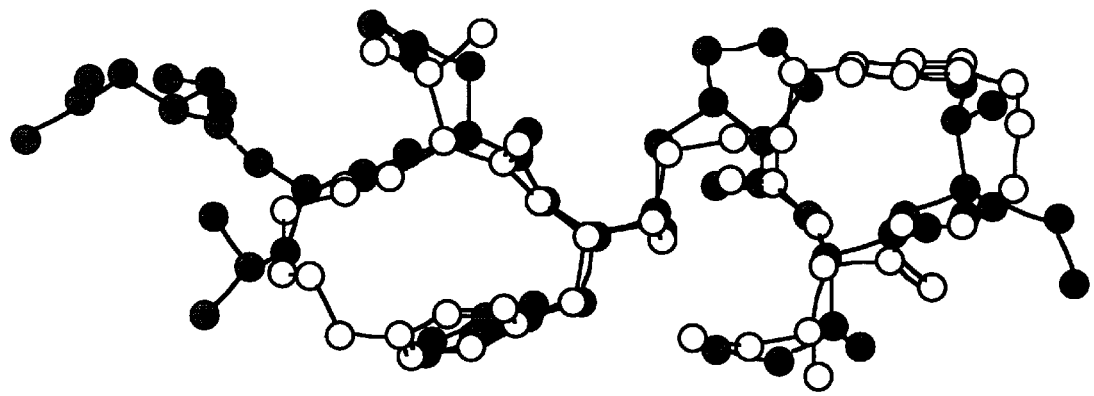

FIGS. 13–14 demonstrate that cyclic inhibitors of the invention are accurate structural mimics of the peptide JG-365. The inhibitory data indicated that the compounds also exhibited functional mimicry in that they had comparable protease inhibiting activities compared to JG-365.

EXPERIMENTAL

Determination of Inhibition Data

HIV-1 protease activity was measured at 37° C. using a continuous fluorimetric assay based on the method of Toth et al., (Toth et al., 1990, Int. J. Pept. Res. 36 544–550). The substrate, 2-aminobenzoyl-threonine-isoleucine-norleucine-(p-nitro)-phenylalanine-glutamine-arginine-$NH_2$ (Abz-$NF^*$-6), was synthesised by solid phase peptide synthesis (Kent et al., 1991, In: Peptides 1990: Proceedings of the Twenty-First European Peptide Symposium (Girault, E. and Andrew, D. eds.) pp 172–173, ESCOM, Leiden). Enzyme activity was measured as the increase in fluorescence intensity upon substrate hydrolysis. The change in fluorescence intensity was monitored with a Perkin Elmer LS50B luminescence spectrometer fitted with a thermostatted micro cuvette holder. Measurements were carried out using an excitation wavelength of 320 nm (bandwith 5 nm) and an emission wavelength of 320 nm (bandwith 5 nm).

Inhibition assays were routinely carried out at pH 6.5 and $\mu$=0.1 M using a single substrate concentration. The assay mixtures contained 50 $\mu$M Abz-$NF^*$-6 in 100 mM 2-(N-morpholino)ethanesulphonate buffer, containing 10% (v/v) glycerol and 50 $\mu$g/ml bovine serum albumin, in a total final volume of 400 $\mu$l. Where inhibitors had to be dissolved in dimethyl sulphoxide or other organic solvents, the final concentration of solvent in the control and inhibition assays were kept absolutely constant because of the severe inhibitory effect of some solvents on the enzyme activity (Bergman et al., 1992, 17th Ann. Lorne Conf. on Protein Struct. and Funct. Abstr.). In all assays, the reaction was initiated by the addition of 10 $\mu$l of enzyme solution.

Inhibition was expressed in terms of the $IC_{50}$ value (i.e. the concentration of inhibitor that caused 50% loss of enzyme activity in the standard assay (50 mM Abz-$NF^*$-6, pH 6.5, $\mu$=0.1 M, 37° C.)).

The data obtained by the assays discussed above is reported in Tables 1 to 13.

Structure-Activity Relationships for Cyclic Inhibitors

The class of inhibitors that were investigated in Tables 1 to 13 were based upon natural substrate sequence: Ser-Leu-Asn-Phe-Pro-Ile-Val.

The first change involving replacement of the scissile amide bond with a "transition-state isostere" gave the known inhibitor JG-365. Inhibitor potencies shown below refer to our assays.

| AcSerLeuAsnPhe[*CHOH—$CH_2$—N]ProIleValOMe | | |
|---|---|---|
| * stereochemistry at this centre | Inhibitor | Potency |
| S-isomer | $IC_{50}$ | 6 nM |
| R-isomer | | 44 nM. |

This compound is, however, inactive at 100 $\mu$M against HIV in cells. This is likely due to either:

(a) hydrolysis of peptide bonds inside cells by other peptidases en route to HIV-1 protease; or (b) inability to enter cells.

Truncation of the Serine reduces protease inhibition 10-fold:

AcLeuAsnPhe[˙CHOH—$CH_2$N]ProIleValOMe $IC_{50}$ 60 nM

Compound 1

We set out to make a range of macrocycles (Tables 1–13 attached) as mimics of this peptide, constraining the LeuAsnPhe component while at the same time providing stability. The cyclization process was expected to protect the peptide amide bonds "invisible" to peptidase enzymes that normally break down peptides. Thus the macrocycles were expected to behave as non-peptide "space-filling" groups.

Table 1: Compound 2 and 3 were computer modelled and 3 seemed to overlay reasonably well on compound 1. These were synthesized and the activities indicated that 3 had successfully functionally mimicked compound 1. Interestingly, truncation of the C-terminal end reduced potency (cf. 3 with 5 and 7).

The magnitude of this loss of activity is sufficient to account entirely for the inactivity of JG-365 against HIV in cells if cellular peptidases were chopping it up (explanation (a) above).

Next we derivatised the cycle at the N-terminus in an attemp to improve/optimise its activity. Compounds 8–13 (Tables 1 & 2) suggest that expanding the —$(CH_2)_3$— linker in the cycle with a —$(CH_2)_4$— or 4 atom spacer did not reduce the potency and modelling suggested that the fit to the enzyme groove was better. Compounds 10 & 11 (Table 1) were thought to offer additional binding from the 2 OH groups to the enzyme's Arg-8 located nearby. This was unsuccessful, since no improvement was observed in potency compared to 3 or 9. However, the stereochemistry of the alcohols needed to be specific to make such interactions and the stereoisomers were not isolated in this work.

Table 2: Compounds 14 & 15 show that the uncyclized version had slightly reduced potency—the reason for cyclizing these molecules was to gain increased stability to hydrolytic enzymes that might "chew" up the inhibitors before they reach their target HIV protease. Surprisingly, there was no dramatic increase in potency for the cyclised inhibitor (e.g. 13) over the uncyclised analogue (e.g. 15), an increase that might have been expected on the basis of conformational entropy arguments—the cycle was preorganised for interacting with the enzyme whereas the more flexible uncyclised inhibitor requires energy to rearrange into a binding conformer.

Compounds 16 and 17 were attempts to increase potency by increasing the size of the macrocyclic ring—activity was instead reduced.

Table 3: Compounds 18–25 were made in the hope of increasing potency due to extension of a group from the macrocyclic ring into a position occupied by Ser of JG-365. (Note that JG-365 was more potent than compound 1). Activities were no better than compound 3. The modelling of the inhibitors suggested that the 3 dangling groups on the left hand side of these cycles in 18–23 have the wrong stereochemistry to mimic the Serine of JG-365. Hence compounds 24 & 25 were made (opposite stereochemistry for $NH_2CO(CH_2)_2$— substituent on left hand side).

Table 4: These were attempts at remodelling the C-terminus of the cycle (i.e. replacing the Pro-Ile-Val ("PIV") with other groups). Compounds 26 & 27 show that the right hand side has not been as good as PIV since activity is only $\mu$M instead of nM. Similarly 28–35 were also less effective. The results for 30–35 did suggest, however, that the R substituent was better for isobutyl than for isopropyl or tertiary butyl.

Table 5: On the other hand, Table 5 shows that Pro-NtBu on the C-terminus is satisfactory with an $IC_{50}$ of 194 nM (compound 38). Note that the cycle is important as 36 & 37 were much less active than 38 & 39. This was encouraging because in 38 the right hand side of the molecule has been truncated by effectively one amino acid (the Val of JG-365). The tertiary butyl side chain that hangs off the proline ring likely fills P2' and there is not much unfilled space in the P2' pocket as shown by the fact that 40 & 41 (were 2 isopropyl groups need more space than 1 tertiary butyl) are much less active.

Compounds 42–45 were designed to keep the t-butyl in P2' and bulk out the P1' position formerly fileld by the 5-membered ring of proline. Compound 44 successfully did this and was a landmark compound for this series of inhibitors. Since the cycle is stable, we do not believe that this type of molecule can now be cleaved readily by other peptidases. We did, however, anticipate a problem with cellular uptake since the $LogP_{o/w}$ (octanol-water partition co-efficient) was ~0.0, indicating low lipophilicity. Results initially indicated high potency against HIV in cell culture ($EC_{50}$ ~15 nM). However, this compound was a poor inhibitor of viral replication in cells ($EC_{50}$ ~5 $\mu$M), a result attributed to the anticipated poor cellular penetration. Attempts have been made to improve cellular permeability by making these compounds more lipophilic without completely losing water solubility.

Table 6: Compounds 46, 47 tested the effect of phenylalanine in the P1' position versus proline used in earlier Tables—there was not a great deal of difference although one feature of the inhibitors which did emerge was that a proline-like P1' substituent goes better with Asn in P2 and a phenylalanine-like P1' substituent goes better with Val in P2.

Compounds 48–53 compare the effect of ring size on inhibitor activity, we find that the larger ring did impart slightly more activity to the inhibitor. Compounds 54 & 55 demonstrated that the isobutyl substituent on the ring was also slightly better than the isopropyl of 48/49. Compounds 56 & 57 tested the effect of inserting a sulfonate into the backbone of the ring in anticipation of interacting the Arg8/108 of the enzyme.

Table 7: Compounds 58 and 60 use the same macrocycle as before, but report on the usefulness of a sulfonamide in P1' and P2'. Greater activity was obtained with the free amine terminus (60) than the amide (59), although both compounds were potent inhibitors of HIV-1 protease. Compound 60 thus became a lead compound for further development as a potential anti-viral compound. It does indeed show anti-viral activity at concentrations below 1 $\mu$M. Compounds 60–73 were developed as more lipophilic derivatives for evaluation against the virus, with the exception that they might more effectively penetrate cell membranes.

Table 8: Compounds in Table 8 were designed and synthesized to test different P1' and P2' handles on the N-terminal cycle. 74/75, 78/79 and 80/81 contain benzylic groups in P1 and P1' while 76/77 and 82/83 contain a benzylic group on P1 and a proline mimetic in P1'. All R-isomer had values for $IC_{50}$ 1–1000 nM. The benzimidazole at P2' in 74–77 can hydrogen bond through its NH proton, similar to the hydroxyl group of the indane of 78/79 and the hydroxyl group of the phenylglycinol in 80/81. In compounds 82/83, the benzylic substituent on the pyrazine ring extends into the P3' position affording increased potency.

The same idea exploited for mimicking the N-terminal tripeptide Leu-Asn/Val-Phe with a macrocycle can also be applied to the C-terminal tripeptides Phe-Ile-Val and Pro-Ile-Val.

Table 9: This Table refers to use of a cyclic mimetic of the C-terminal tripeptide Phe-Ile-Val with varying N-terminal substituents. Clearly this cycle leads to potent inhibitors of HIV-1 protease with $IC_{50}$ values in the range of 1–60 nM. The preferred stereochemistry at the alcohol was R in most cases. The ring size had little effect (cf. 87 versus 88), the hydroxyl group of the transition state isostere was, however, critical for high potency (89 versus 90). The tetrahydrofuran group of 91 was not better as a P2 filler over the t-butyl group in 89 but both were more effective than the aromatic ring in 92 as P2 substituents. Compound 93 containing the quinoline group was a very potent inhibitor of HIV-1 protease and represented a good lead compound for development of anti-viral potential. It is equipotent as a protease inhibitor with the DuPont-Merck compound DM323 but binds by a very different mechanism. It also shows anti-viral activity against HIV in cell culture with an $IC_{50}<1$ $\mu$M.

Table 10: Compounds 95–106 were attempts to improve lipophilicity to enhance cellular penetration to further increase anti-viral activity. In these examples, the idea is that the substituent (R) carries a lipophilic tail to add fat solubility without interfering with interactions between the inhibitor and enzyme.

Compound 107/108 have slightly enhanced activity due to the better fit and hydrogen-bonding interactions between the Gln side chain and the protease.

A logical extension of the concept of mimicking the tripeptides Leu-(Val/Asn)-Phe and Phe-Ile-Val or Pro-Ile-Val is to combine these monocyclic components into a bicyclic hexapeptide mimic. Thus the bicyclic molecules described in Tables 11–13 are potent inhibitors of HIV-1 protease.

Table 11: Compound 109 was 100-fold more potent than 110. The R-stereochemistry generally being more favourable for these bicycles which tend to be low nM inhibitors of HIV-1 protease. Compound 111 ($IC_{50}$ 1 nM) was taken as a lead compound for further development. Changes that increase activity include replacing Val with Leu (113/114) and increasing ring size (115/116).

Table 12: Compounds 117–120 compare the effect of an hydroxyproline with a thioproline as P1' substituents of the macrocycle. 121 shows the effect of Asn versus Val in P2 (119) in the presence of a pro-mimic at P1'. 123 has a bulkier piperazine at P1' and this more successfully mimics JG-365, moreover with an Asn instead of Val at P2 even better activity is obtained. Table 13: Compounds 127–130 utilise a phenylglycine at P2 and/or P2'. In our work, we have compared a range of over a dozen peptidic inhibitors of HIV-1 protease by overlaying their known X-ray crystal structures. Remarkably we find that the "consensus" inhibitor is a bicycle with phenylglycien at positions P2 and P2'. Compound 131/132 with a D-Gln at position P2' were also quite active.

Cell Penetration

By developing potent (nM) inhibitors of HIV-1 protease without susceptibility to peptidases (i.e. 'peptide-like' properties), we envisaged that the ability to enter cells would be related to the partioning between water and cell membrane.

To predict the partition co-efficients, we used a modelling programme and found that anti-viral activity requires a Log P of 2.5.

We have calculated some partition co-efficients (Log P values) describing solubilities in octanol (o), as being indicative of lipid or membrane permeability, over water (w) to predict likely uptake of our inhibitors. The following list suggests that the macrocycles are more soluble in octanol than water (Log P>zero) whereas peptides have very little octanol solubility and are very water soluble (Log P is negative). Our macrocyclic compounds are clearly more water soluble than current HIV-1 protease inhibitors that exhibit anti-viral activity.

To check the importance of Log P, we have calculated it for some non-steroidal anti-inflammatory drugs in the market place and find their numbers are 3–4. Some indications of Log P values for our macrocycles are given below.

| Compound | Log P (o/w) |
|---|---|
| 3 | −0.69 |
| 18 | −0.46 |
| 20 | −2.03 |
| 22 | −2.80 |
| 25 | −2.97 |
| 34 | +0.06 (i.e. octanol solubility = water solubility |
| 40 | +3.61 |
| 42 | −0.11 |
| 44 | +2.74 |
| 46 | +3.25. |

HIV-1 PR: Inhibitor Co-crystallisation and Structure Determination

Figure 1:
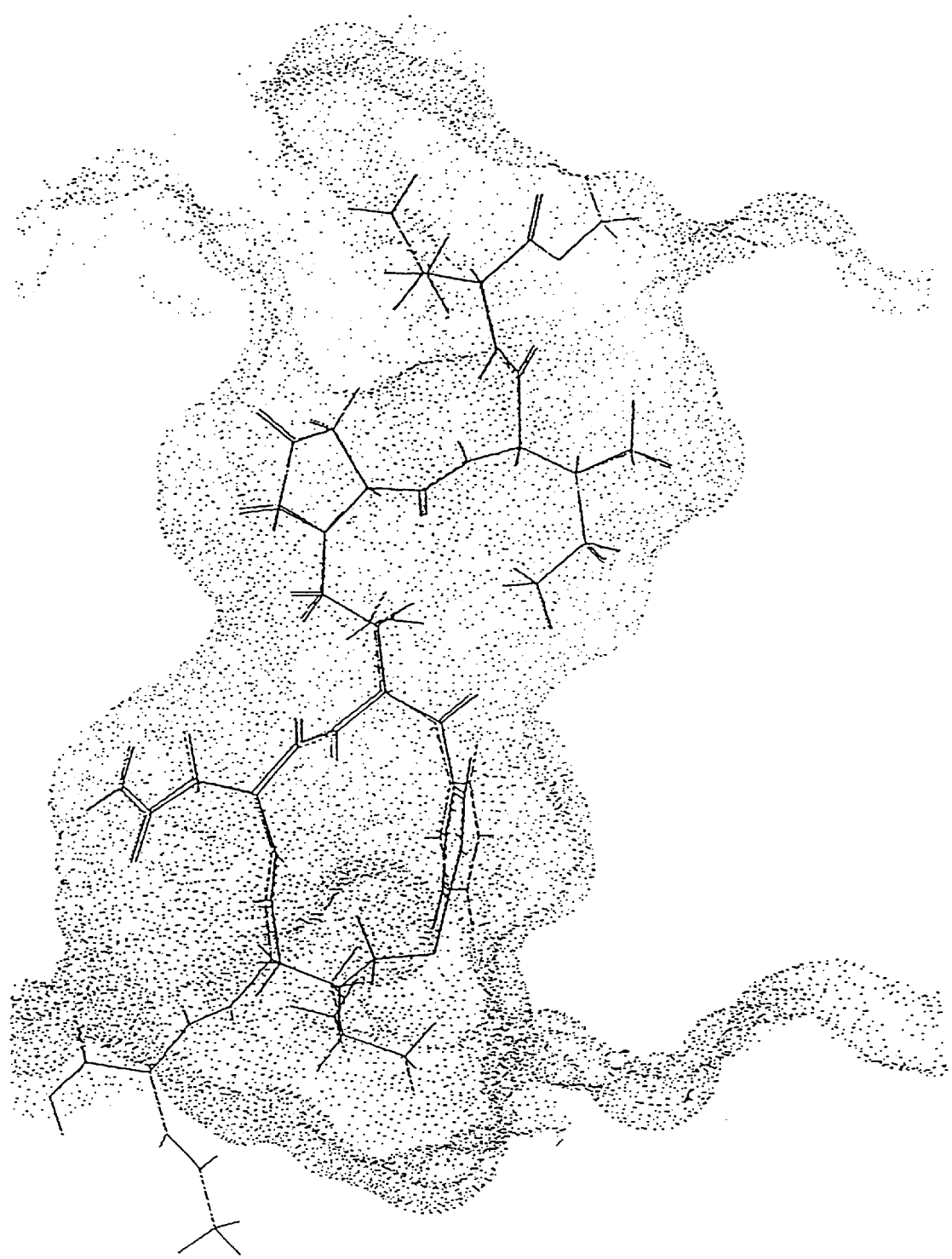
FIG. 1 hereinafter shows a model of the structural mimic 3 (Table 1 hereinafter —S-isomer) superimposed on the protease-bound conformation of JG-365. While there was a good match for the structures, including the PIV region which was unaffected by the macrocycle substitution, the R-isomer of the chiral alcohol superimposed poorly. The slightly larger N-terminal cycle 13 (Table 2 hereinafter) superimposed better than compound 3 referred to in Table 1A hereinafter upon the linear inhibitor whereby the benzyclic ring matched the phenylalanine side chain.

For co-crystallation studies, the inhibitor referred to in FIG. 1 was dissolved in DMSO to give a 130 mM solution. This was mixed in a 1:10 ratio with the Aba-substituted synthetic HIV-1 PR (5 mg/ml in 0.1 M acetate buffer pH 5.5) to give a final inhibitor concentration of inhibitor. The protease:inhibitor mixture crystallised from 40% ammonium sulphate and 0.1 M acetate buffer, pH 5.5.

A rod-shaped crystal measuring 0.4×0.1×0.1 mm was used for X-ray data measurement of the HIV-1 PR inhibitor complex. Crystallographic data to Å were measured on an imaging plate area detector RAXIS IIC using CuKα X-rays (60 kV, 90 mA) from an RU-200 rotating anode X-ray generator.

The crystal spacegroup is $P2_12_12_1$, with a unit cell of a=51.3 Å, b=58.8 Å, c=62.3 Å, α=90°, β=90°, γ=90° which is isomorphous with several previously reported HIV-1 PR:inhibitor complexes. The merged data (11,924 reflections from 69,201 observations) has an overall $R_{mer}$ of 8.0%, overall I/sigI of 10.7 and represents 97% of all data to 2.06 Å. The highest resolution shell (2.06–2.25 Å) is 95% complete with I/sigI of 3.7.

The structure of the protease:inhibitor complex was solved by difference Fourier analysis using the protease structure from the complex with JG365 (7hvp.pdb). The inhibitor and solvent atoms were removed from this structure, and the cysteines were modified to Aba residues. The initial R factor, using $F_c$ and $\Phi_c$ from this protease model gave an R factor of 31.2% with the measured $F_o$. The first difference Fourier map ($F_o$-$F_c$) showed density for the inhibitor at the active site.

The inhibitor was modelled into the density and the structure of the complex refined using X-PLOR. After several rounds of model building, inclusion of solvent, and refinement the current R factor is 17.4% (6 to 2 Å) with rms deviations in bond length and bond angles of 0.012 Å and 2.073°, respectively.

Figure 2:
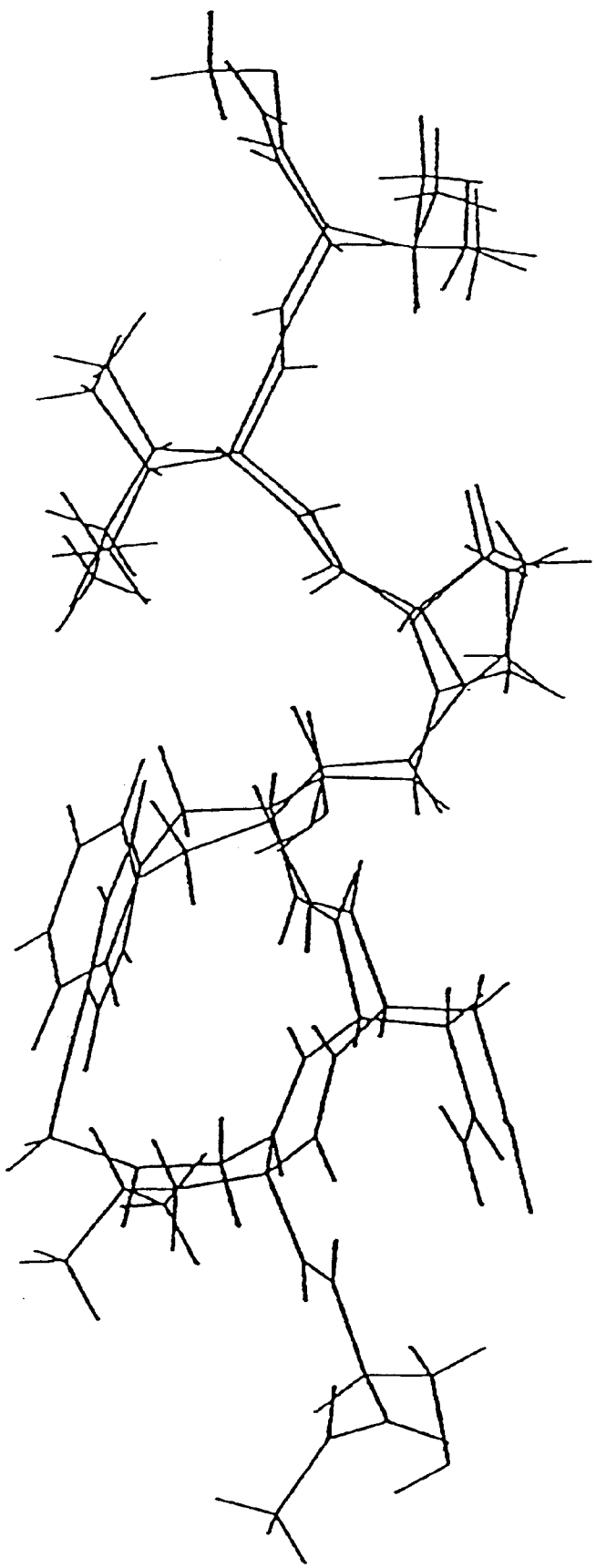
Figure 3:
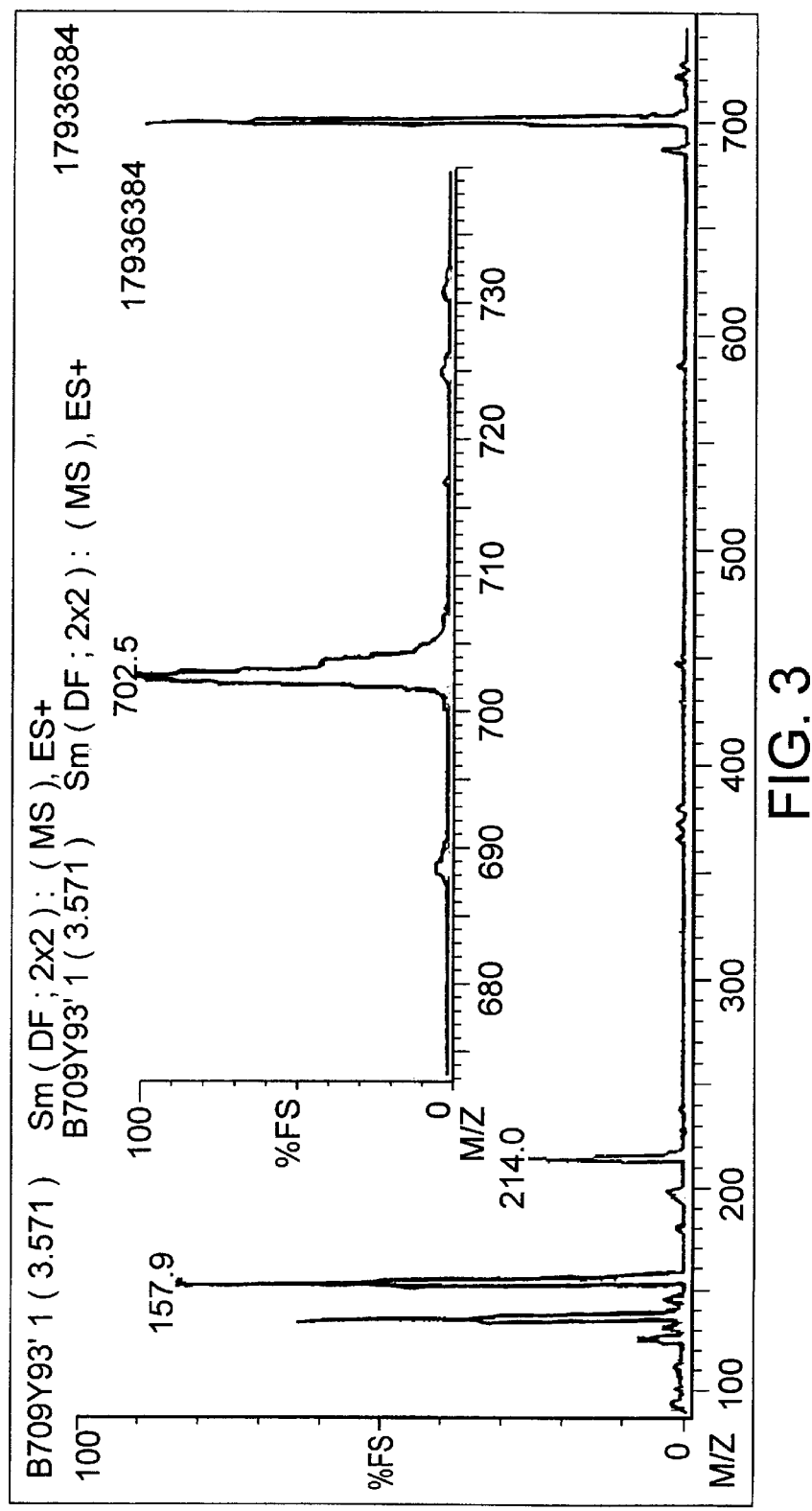
Figure 4:
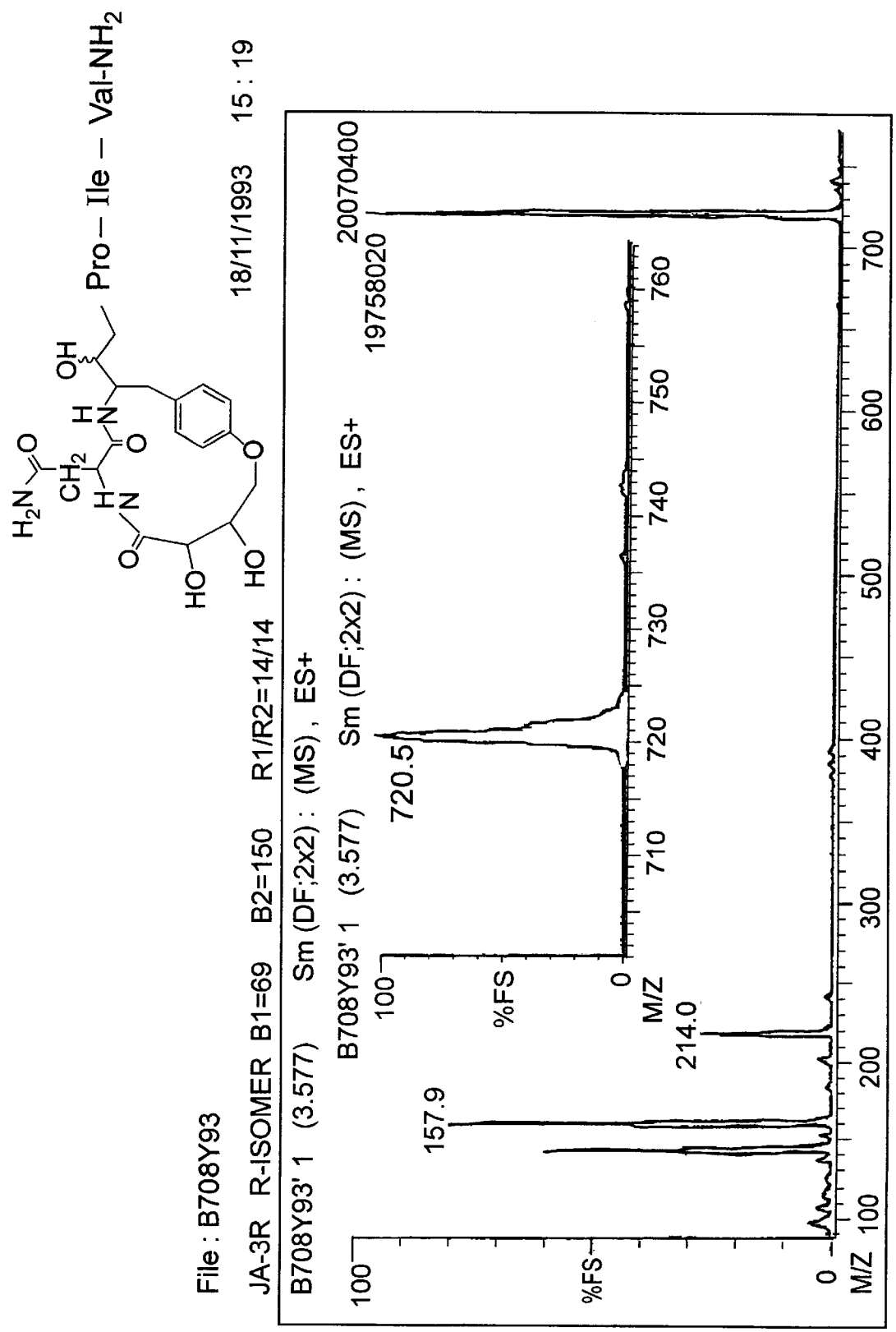
Figure 5:
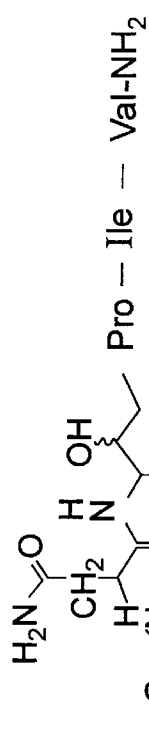
Figure 5:
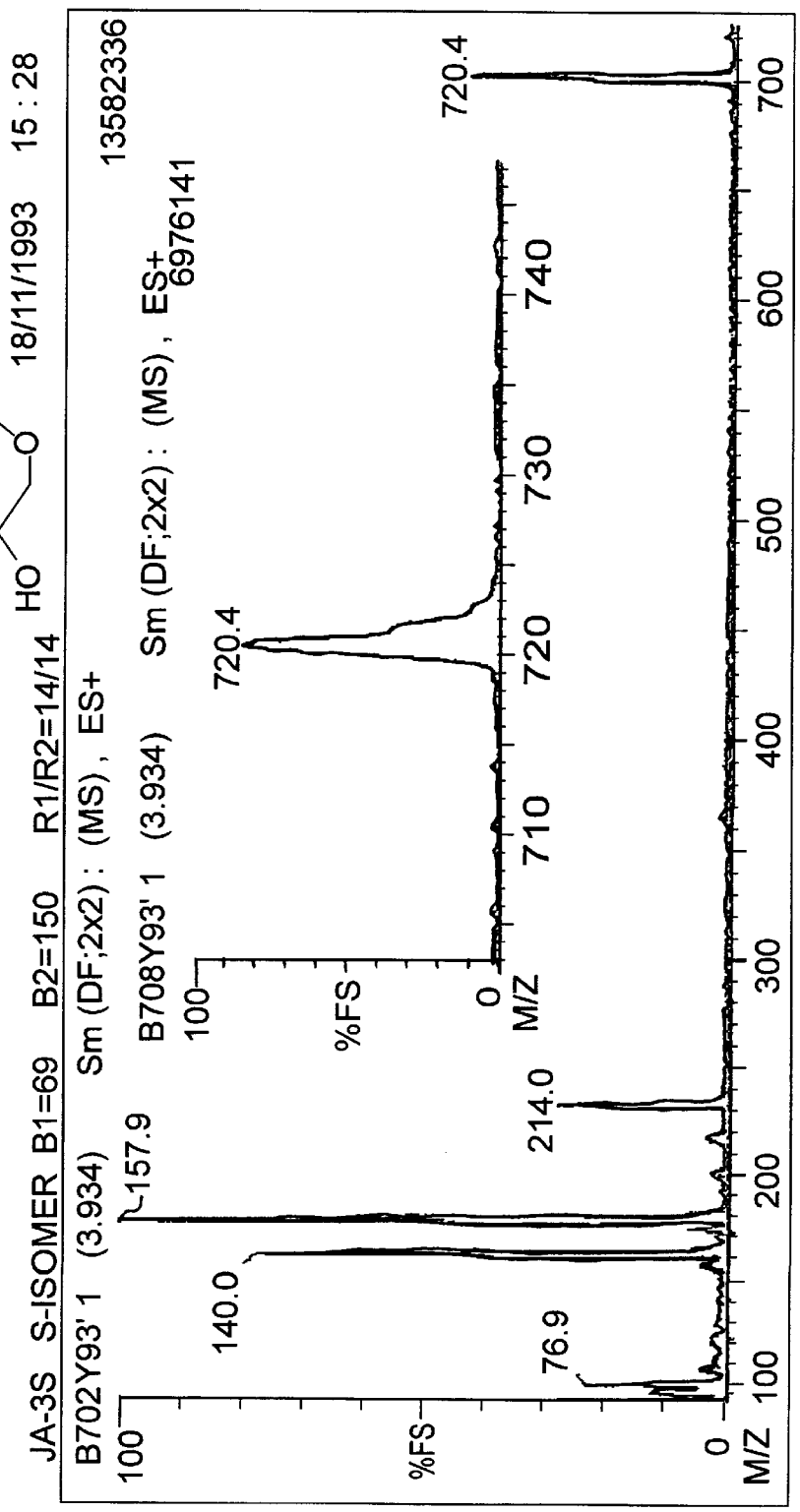
Figure 6:
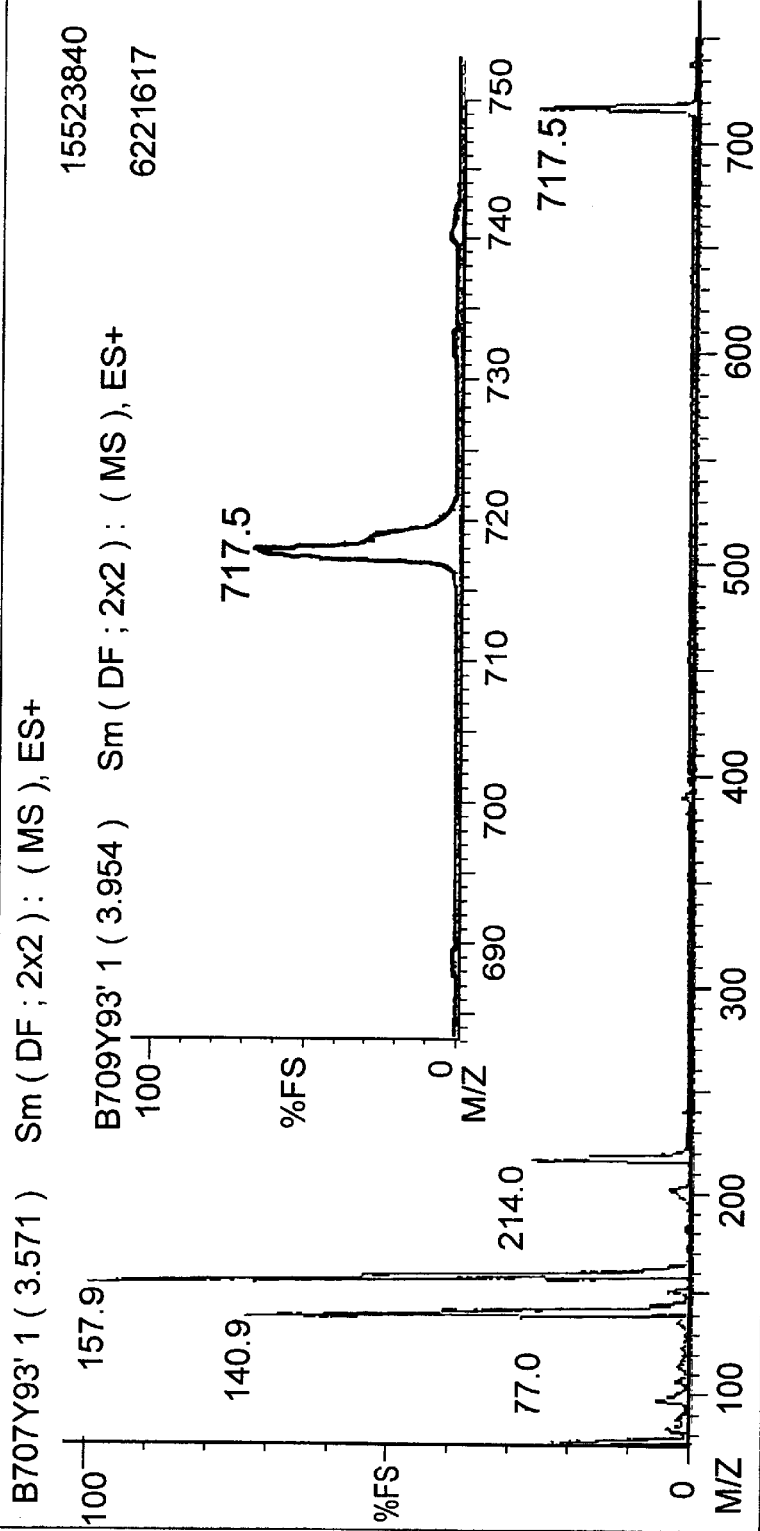
Figure 7:
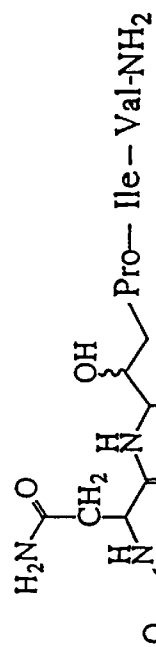
Figure 7:
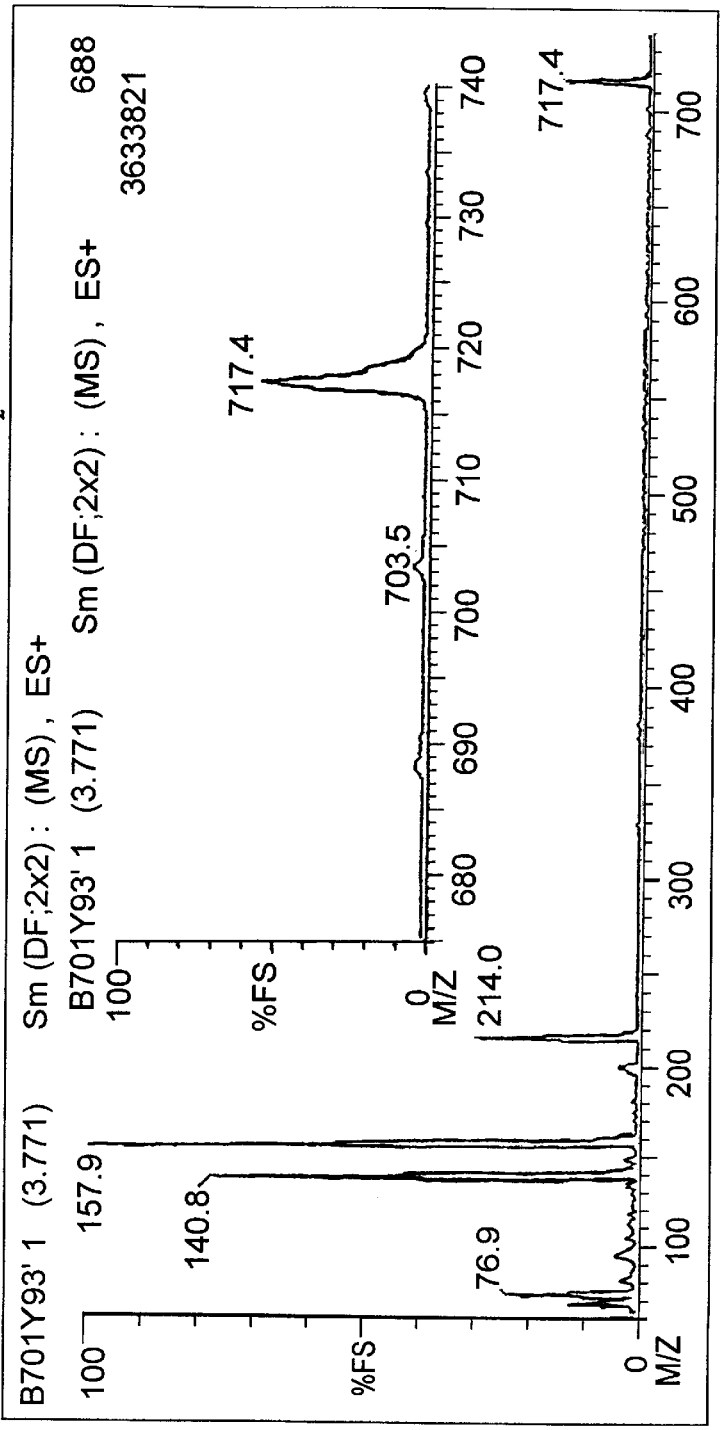
Figure 8:
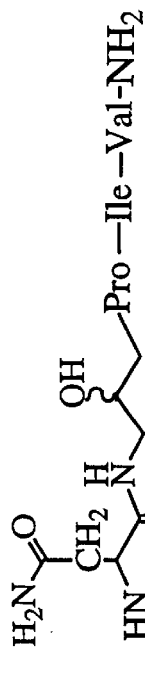
Figure 8:
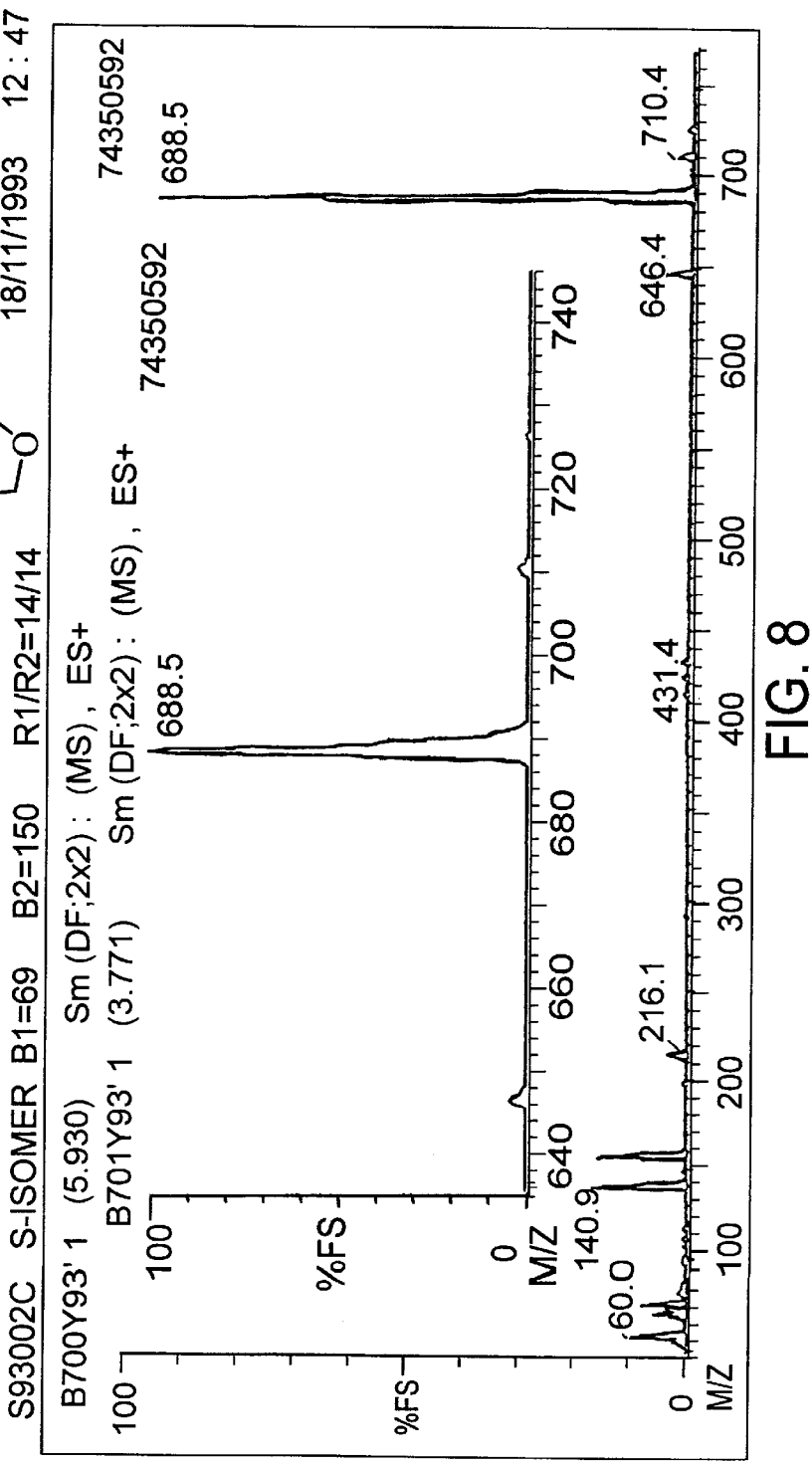
Figure 9:
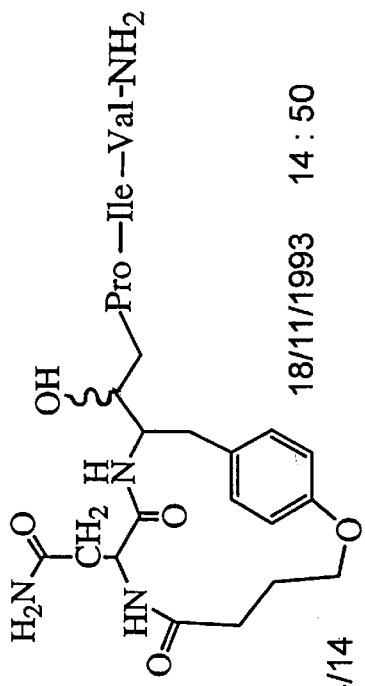
Figure 9:
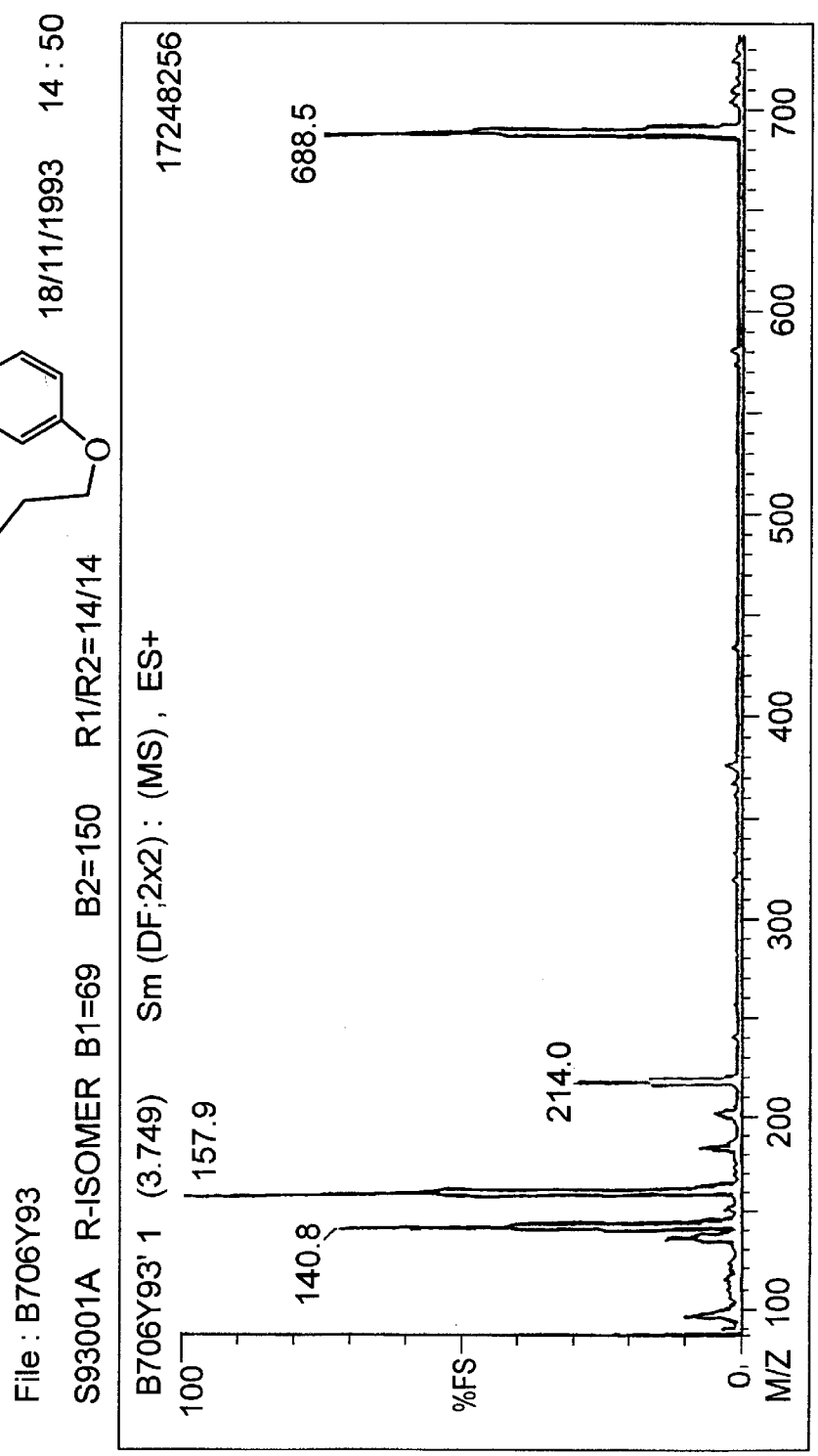
Figure 10:
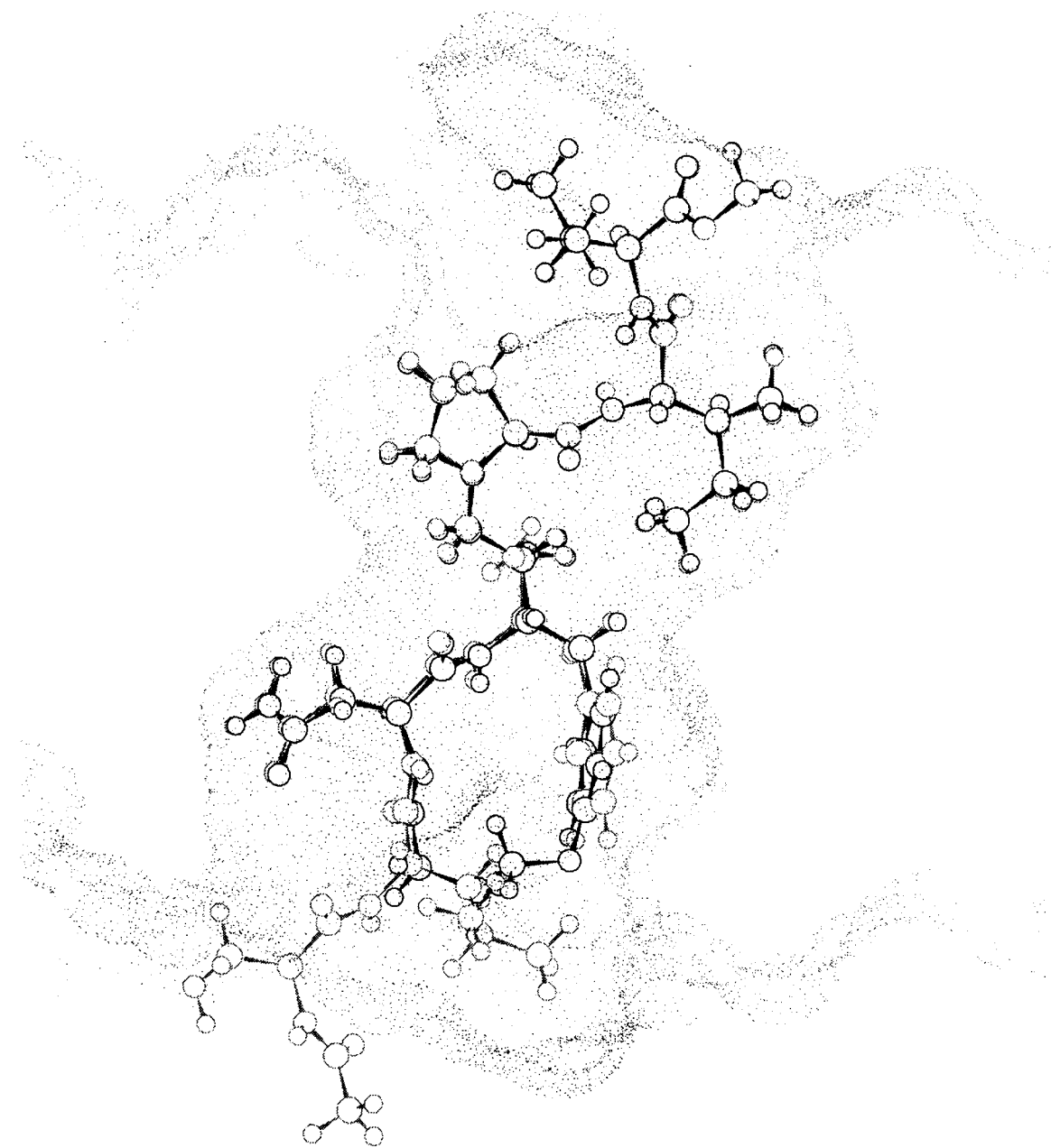
Figure 11:
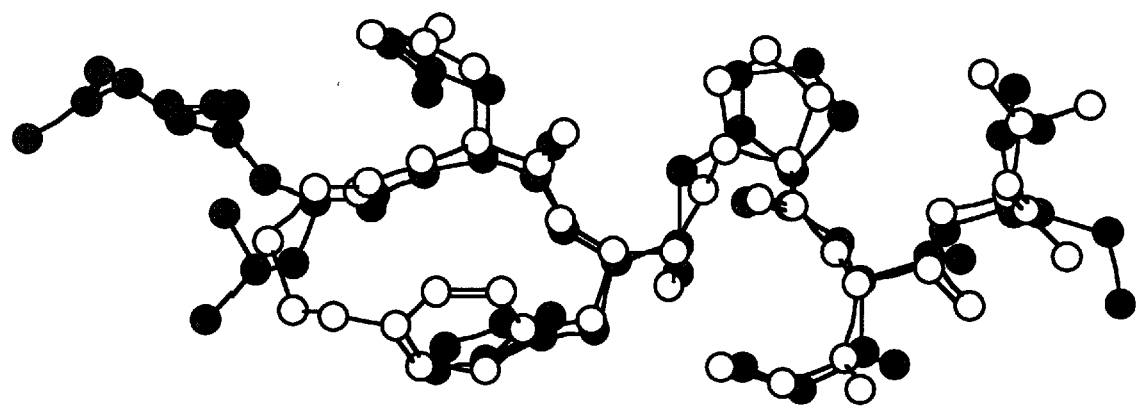
Figure 12:
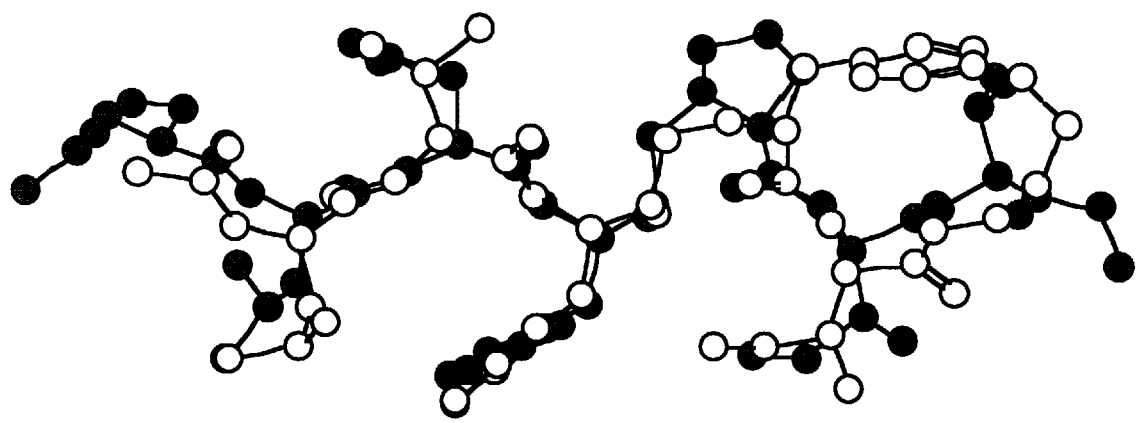

The structure showed that the inhibitor binds to the protease dimer in much the same way as JG-365 as shown in FIG. 2. There is no observed density for one of the $(CH_2)_3$ carbons atoms in the ring, indicating that this part of the structure is flexible. Other atoms in this ring may also be poorly localised since the density is weak and during structure minimisation these atoms have refined with high B factors. Nevertheless, the structure clearly shows that the cycle overlays or superimposes closely on JG-365 as it exists in the conformation bound to HIV-1 protease.

Three other inhibitors, i.e. compounds 44, 89 and 123 in addition to compound 3 have also been co-crystallised with HIVPR and their X-ray crystal structures determined (see Table 14). The full X-ray structural data for compounds 3, 44, 89 and 133 has been deposited in the Brookhaven Protein Data Bank in the United States.

Stability of Macrocycles

Evidence of macrocycle stability is shown in FIGS. 3–9 which show mass spectra of macrocycles after exposure to the gastric peptidases pepsin 3a, gastrixin and cathepsin D. This data demonstrates that the macrocycles are proteolytically stable in vitro.

In this procedure, the relevant compounds were exposed to peptidases for 1 hour at 37° C. and then assayed by electrospray mass spectroscopy. Molecular weights were determined from the data indicating that the macrocycles remained intact after contact with the peptidases.

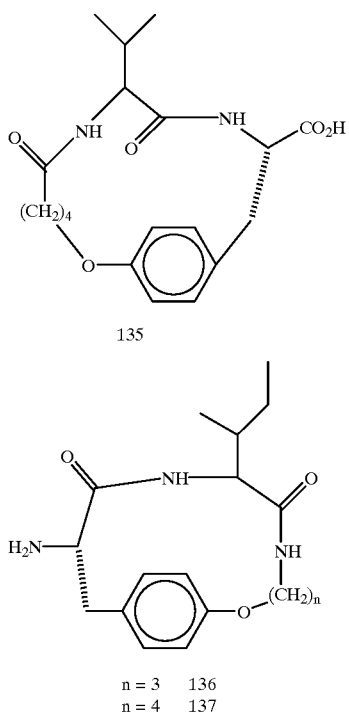

n = 3  136
n = 4  137

These above cycles were also evaluated for stability in 3 M HCl and human blood.

Stability in Hydrochloric Acid

The above cycles were dissolved in 3 M HCl and heated to ~45° C. The reactions were monitored daily for 4 days by mass spectrometry. There was no hydrolysis or degradation of the cycles over this time.

Stability in Human Blood

Human blood (5 ml) was allowed to clot for 1 hour before centrifuging (5 min). Test compound (200 μg) was assayed in duplicate by adding 450 μl saline or serum, vortexing and incubating (1 hr, 37° C.). After adding acetonitrile (1 ml, 4° C.), vortexing (30 s) and centrifuging (5 min, 4° C.), the supernatant was removed. After freezing in liquid nitrogen, lyophilizing to dryness, resuspending in 100 μl buffer, the products were analysed by HPLC and electrospray mass spectrometry. No degradation products were observed, only the unchanged cyclic compounds were detected.

Assay for Anti-viral Activity

Method: Target cells (PHA-stimulated cord blood mononuclear cells) were washed free of PHA and inoculated with HIV-1 (strain TC354) at a multiplicity of infection of 1, in the presence of 20 μg/ml DEAE-dextran for 30 mins. Cells were washed to remove unbound virus and residual DEAE-dextran. $10^5$ cells were added to each well of 96 well plate, solutions of test compounds were added, each tested in triplicate. Dilutions were prepared in RPMI/1640. Tissue culture medium (RPMI/1640 buffer, 10% FCS, 20 U/ml rU-2) was added to a final volume of 200 μl. Reverse transcriptase activity was assayed four days post inoculation, RT activity >30 cpm was considered positive for HIV-1 replication.

Representative test compounds subjected to anti-viral testing included 44, 68 and 93. These compounds inhibited replication of the virus in the above assay with effective concentrations of 1 μM, 100 nM and 100 μM respectively.

Synthesis of Cyclic Inhibitors

In relation to preparation of the protease inhibitors of the present invention, suitable methods of preparation of these compounds are described in Schemes 1, 2, 3 and 4 attached herewith. Scheme 1 is suitable for preparation of compounds of structure (i) where Z is peptide, Scheme 2 is suitable for preparation of compounds of structure (i) where Z is non-peptide and Scheme 3 and 4 are suitable for preparation of compounds of structure (ii). Structure (iii) may be made by a combination of Schemes 1, 2 and 3 or closely related synthetic methods.

Scheme 1 depicts a synthesis of macrocycle 2 and 3 which, with minor modifications was also used for the synthesis of derivatives 4–25. The direct alkylation of Boc-tyrosine 1 with ethyl 4-bromobutyrate gave exclusively the O-alkylated tyrosine 1a. This was converted by an established method (McKervey, M. A. & Ye, T., Tetrahedron, 48, 37, 8007–22) to the diazoketone, and subsequently to the bromomethyl ketone 1b with Hbr. Tripeptide 4 was assembled on MBHA resin using HBTU, alkylated with the bromomethyl ketone (1b), followed by reduction with sodium borohydride to give the hydroxyethylamine isostere 5. After introducing Asn, the peptide was cleaved from resin (HF), de-esterified with NaOH, and the mixture of diastereomers (6) was purified by reverse phase HPLC in 54% overally yield. Dilute (mM) solutions of (6) were cyclized intramolecularly using BOP to give 2 and 3. The diastereomers were separated by RP-HPLC to give pure 2, S (21%) and 2, R (28%) which were characterised by ionspray mass spectrometry (M+H, 688). The stereochemistry of the alcohol was verified for the S-isomer by X-ray crystallography of the inhibitor-bound complex 3-HIVPR (The three dimensional crystal structure was determined for a complex of 7a with HIVPR (Wickramsinghe, W. & Martin, J., University of Queensland, unpublished work) to a resolution of 2.1 A. This structure identified the isomer as 7a,S and showed almost identical structural overlay as the model on the crystal structure of JG-365 bound to HIVPR.) The two chiral centres in the macrocycles 2 and 3 were thus derived from simple L-amino acids.

Also attached herewith is details of Schemes 2 and 3 which describes the synthesis of other N-terminal cycles and Schemes 3 and 4 describe alternative syntheses of C-terminal cyclic inhibitors.

The bicycles (Tables 11–14) were prepared by general synthesis involving coupling of the C-terminal cycle (compound 4 in Scheme 3) with (compound bottom LHS) compound Z from Scheme 4.

Synthesis of Compounds Comprising Hydrolytically Stable Cyclic Mimetics of Tripeptides Leu-Asn-Phe and Phe-Ile-Val General Methods All materials were obtained commercially as reagent grade unless otherwise stated. Melting points were determined on a Reichert hot stage apparatus and are uncorrected. $^1$H NMR spectra were recorded on a Bruker ARX 500 MHz spectrometer using $D_2O$ as internal standard for water-soluble samples or TMS for spectra recorded in $CDCl_3$. Proton assignments were determined by 2D COSY & TOCSY experiments. $^{13}$C NMR spectra were measured on a Varian Gemini 300 NMR spectrometer and chemical shifts are reported in ppm relative to $CD_3OH$, EtOH or $CDCl_3$. Preparative scale reverse phase HPLC separations were performed on Waters Delta-Pak PrepPak $C_{18}$ 40 mm×100 mm cartridges (100 Å); analytical reverse phase HPLC on Waters Delta-Pak Radial-Pak $C_{18}$ 8 mm×100 mm cartridges (100 Å); using gradient mixtures of water/0.1% TFA and water 10%/acetonitrile 90%/TFA 0.1%.

Mass spectra were obtained on a triple quadrupole mass spectrometer (PE SCIEX API III) equipped with an Ionspray (pneumatically assisted electrospray) (Bruins et al., 1987, Anal. Chem. 59 2642) atmospheric pressure ionisation source (ISMS). Solutions of compounds in 9:1 acetonitrile/0.1% aqueous trifluoroacetic acid were injected by syringe infusion pump at μM-pM concentrations and flow rate of 2–5 μl/minutes into the spectrometer. Molecular ions, {[M+nH]$^{n+}$}/n, were generated by the ion evaporation process (Iribane, J. V. & Thomson, B. A., 1976, 64 2287) and focussed into the analyser of the mass spectrometer through a 100 mm sampling orifice. Full scan data was acquired by scanning quadrupole-1 from m/z 100–900 with a scan step of 0.1 dalton and a dwell time of 2 msec. Accurate mass determinations were performed on a KRATOS MS25 mass spectrometer using Electron Impact ionisation.

| Abbreviations | |
|---|---|
| LNF = | Leu-Asn-Phe; |
| PIV = | Pra—Ile-Val; |
| DIPEA = | diisopropylethylamine; |
| MBHA = | p-Methylbenzhydrylamine resin. HCl, 0.79 meq/g; |
| MF = | dimethylformamide; |
| BOP = | [Benzotriazol-1-yl-oxy-tris(dimethylamino) phosphonium]hexafluorophosphate; |
| HBTU = | O-Benzotriazole N',N',N',N'-tetramethyluronium hexafluorophosphate; |
| TFA = | Trifluoroacetic acid. |
| Ethyl | 4-[4'(2-(t-butoxycarbonylamino)-2-carboxy)ethyl]phenoxy butanoate (Z) |

To a suspension of NaH (1.2 g, 50 mmol) in dry THF (80 ml) was slowly added Boc-tyrosine (3.5 g, 12.46 mmol), under an argon atmosphere. The solution was stirred at room temperature for 5 minutes, after which ethyl 4-bromobutanoate (7.28 g, 37.35 mmol) was added in one portion and the suspension heated at reflux for 16 hrs. A further 3 eq. of both NaH and ethyl 4-bromobutanoate was added and heating was continued for 5 hrs. Solvent was removed under reduced pressure, the residue dissolved in water (100 ml), and the basic solution was extracted with diethyl ether (3×40 ml) to remove unreacted ethyl 4-bromobutanoate and ethyl cyclopropanecarboxylate side product. The aqueous layer was acidified (pH=2) with 1 M KHSO$_4$ and extracted with ethyl acetate (4×50 ml). The organic phase was dried and evaporated to give the title compound (4.2 g, 91%) as a colourless oil. Although used directly for subsequent reactions, a small amount was purified by reverse phase HPLC (70:30, water/acetonitrile/0.1% TFA) to give a colourless oil. $^1$H NMR (CDCl$_3$) δ; AA'BB' system: 7.08 (d, $J_{AB}+J_{AB'}$, 2H, 8.61Hz, ArH ortho to CH$_2$), 6.81 (d, $J_{AB}+J_{AB'}$, 8.61Hz, 2H, ArH ortho to O), 6.60 (br. s., 1H, COOH), 4.94 (d, 7.6Hz, 1H, NH), 4.55 (m, 1H, Tyr αCH, 4.14 (q, J=7.2Hz, 2H, OCH$_2$CH$_3$), 3.98 (t, J=6.1Hz, 2H, O—CH$_2$—CH$_2$—CH$_2$), 3.14 (dd, J=12.8, 5.1Hz, 1H, Tyr βCH), 3.02 (dd, J=12.8, 6.0Hz, 1H, Tyr βCH), 2.50 (t, J=7.3Hz, 2H, CH$_2$COOEt), 2.09 (m, 2H, CH$_2$—CH$_2$—CH$_2$), 1.42 (s, 9H t-butyl), 1.26 (t, J=7.2 Hz, 3H, OCH$_2$CH$_3$). $^{13}$C NMR (CDCl$_3$) δ 14.19 (OCH$_2$CH$_3$), 24.62 (CH$_2$—CH$_2$—CH$_2$), 28.12 (t-butyl CH$_3$), 30.74 (CH$_2$COOEt), 36.88 (Tyr βCH), 54.35 (Tyr αCH), 60.47 (O—CH$_2$), 66.66 (OCH$_2$CH$_3$), 80.18 (t-butyl), 114.44 (ArC, ortho to CH$_2$), 127.78 (Ar-CH$_2$), 130.37 (ArC, ortho to O), 155.36 (ArC—O), 157.93 (C=O, carbamate), 173.35 (C=O, ethyl ester), 176.25 (C=O, COOH). ISMS 413(M+NH$_4$), 396(M+H), 340(M+H-isobutene), 296(M+H-BOC). HRMS calcd for $C_{20}H_{29}NO_7$, 395.1944; found 395.1943.

(S)-3-(t-Butoxycarbonylamino)-1-diazo-4-(4'-[3-carboethoxy]propyloxy)phenyl-2-butanone (Y)

To a solution of alkylated Boc-tyrosine (Z) (4 g, 10.1 mmol) in dry THF (50 ml) was added N-methyl piperidine (1.58 ml, 12.1 mmol). The solution was cooled to −10° C. under an atmosphere of dry nitrogen and ethyl chloroformate (1.2 g, 1.05 ml, 11.1 mmol) was added in one portion. The solution was stirred for 10 mins during which N-methyl piperidine hydrochloride precipitated. An ethereal solution of diazomethane (excess) was added dropwise to this suspension over 30 mins at −5° C. The reaction mixture was allowed to warm to room temperature over 1 hr after which a slow stream of nitrogen was bubbled through the solution for 15 mins to remove any unreacted diazomethane. The solution was diluted with ether (150 ml) and washed with water (3'100 ml), saturated NaHCO$_3$ (2×100 ml) and brine (1×100 ml). The organic phase was dried with MgSO$_4$ and evaporated in vacuo to give the title compound as a light yellow oil (3.2 g, 75%). While sufficiently pure for synthetic purposes, a small amount was purified by radial chromatography (ethyl acetate/light petroleum, 1:3) and subsequently recrystallised from hexane to give colourless needles, m.p. 73–75° C. $^1$H NMR (CDCl$_3$) δ AA'BB' system: 7.08 (d, $J_{AB}+J_{AB'}$=8.52Hz, 2H, ArH ortho to CH$_2$), 6.82 (d, $J_{AB}+J_{AB'}$=8.52Hz, 2H, ArH ortho to O), 5.21 (s, 1H, CHN$_2$), 5.12 (d, J=8.1Hz, 1H, NH), 4.36 (m, 1H, Tyr αC—H), 4.15 (q, J=7.2Hz, 2H, OCH$_2$CH$_3$), 3.98 (t, J=6.1Hz, 2H, O—CH$_2$), 2.95 (d, J=6.4Hz, 2H, Tyr βCH), 2.51 (t, J=7.3Hz, 2H, CH$_2$COOEt), 2.10 (m, 2H, CH$_2$—CH$_2$—CH$_2$), 1.41 (s, 9H, t-butyl), 1.26 (t, J=7.2 Hz, 3H, OCH$_2$CH$_3$), $^{13}$C NMR (CDCl$_3$) δ 14.22 (OCH$_2$CH$_3$); 24.63 (CH$_2$—CH$_2$—CH$_2$); 28.28 (t-butyl CH$_3$); 30.79 (CH$_2$COOEt); 37.73 (Tyr βCH); 54.41 (Tyr αC—H); 58.50 (CHN$_2$); 60.43 (O—CH$_2$); 66.69 (OCH$_2$CH$_3$); 80.07 (t-butyl); 114.58 (ArC, ortho to CH$_2$); 128.21 (Ar-CH$_2$); 130.34 (ArC, ortho to O); 155.13 (ArC-O); 157.85 (C=O, carbamate); 173.20 (C=O, ethyl ester); 193.13 (diazoketone). ISMS: 437(M+NH$^4$); 420(M+H); 336 (M+H-isobutene-N$_2$); 292(M+H-BOC-N$_2$); Anal. calcd for $C_{21}H_{29}N_3O_6$ C, 60.13%, H, 6.97%; N, 10.02%; Found: C, 60.16%; H, 6.97%; N, 9.85%.

1-Bromo-(S)-3-(t-butoxycarbonylamino)-4-(4'-[3'-carboethoxy]propyloxy)phenyl-2-butanone (X)

A saturated solution of HBr in ethyl acetate was diluted 1:9 with ethyl acetate and added in 1 ml aliquots to a cold solution (0° C.) of the diazoketone (Y) (1.75 g, 4.18 mmol) in ethyl acetate (40 ml). The progress of the reaction was followed by thin layer chromatography. On completion the reaction mixture was washed with a 0.1 M NaHSO$_4$ (2×50 ml), saturated NaHCO$_3$ (2×40 ml) and brine (1×40 ml). The organic phase was dried with MgSO$_4$ and evaporated to dryness to give the title compound as a colourless solid (1.5 g, 75%). While sufficiently pure for synthetic purposes, a small amount was purified by radial chromatography (ethyl acetate/light petroleum, 1:3) and subsequently recrystallised from hexane/dichloromethane to give colourless needles, m.p. 92–94° C. $^1$H NMR (CDCl$_3$) δ AA'BB' system: 7.07 (d, $J_{AB}+J_{AB'}$=8.60Hz, 2H, ArH ortho to CH$_2$), 6.83 (d, $J_{AB}+J_{AB'}$=8.60Hz, 2H, ArH ortho to O); 5.03 (d, J=7.2Hz, 1H, —NH); 4.67 (m, 1H, Tyr αC—H), 4.15 (q, J=7.2Hz, 2H, OCH$_2$CH$_3$), 3.99 (t, J=6.1Hz, 2H, O—CH$_2$), 3.97 (d, J=13.9Hz, 1H, —CHBr), 3.83 (d, J=13.9Hz, 1H, —CHBr), 2.95 (m, 2H, Tyr βCH), 2.51 (t, J=7.3Hz, 2H, CH$_2$COOEt), 2.10 (m, 2H, CH$_2$—CH$_2$—CH$_2$), 1.42 (s, 9H, t-butyl), 1.26 (t, J=7.2 Hz, 3H, OCH$_2$CH$_3$). $^{13}$C NMR (CDCl$_3$) δ 14.15 (OCH$_2$CH$_3$); 24.54 (CH$_2$—CH$_2$—CH$_2$); 28.19 (t-butyl CH$_3$); 30.71 (—CH$_2$COOEt); 33.37 (—CH$_2$Br), 37.00 (Tyr βCH); 58.61 (Tyr αCH); 58.50 (CHN$_2$); 60.37 (O—CH$_2$); 66.66 (O CH$_2$CH$_3$); 80.34 (t-butyl); 114.77 (ArC, ortho to CH$_2$); 127.58 (Ar—CH$_2$); 130.09 (ArC, ortho to O); 155.15 (ArC-O); 157.99 (C=O, carbamate); 173.12 (C=O, ethyl ester); 200.95 (C(O)CH$_2$Br). ISMS: 491/489 (M+NH$_4$, 1:1); 474/472 (M+H,1:1); 418/416 (M+H-isobutene,1:1); 374/372 (M+H-BOC, 1:1); Anal. calcd for C$_{21}$H$_{30}$BrNO$_6$ C, 53.40%; H, 6.40%; N, 2.97%, Found: C, 53.37%; H, 6.30%; N, 2.84%.

[(2S) and (2R)] (S)-3-((S)-Asparaginyl)amino-4-(4'-[3'-carboethoxy]propyl oxy)-phenyl-1-((S)-N-prolyl-(S)-isoleucyl-(S)-valine amide)butan-2-ol (W)

Assembly of the uncyclised peptidomimetic (W) was accomplished by solid phase peptide synthesis (Alewood et al., 1992, Teett. Lett. 33 977–80). MBHA resin (2.15 g, 2 mmol, S.V.=0.93 meq/g) was shaken with DIPEA (0.7 ml, 4.0 mmol) in DMF (12 ml) for 2 mins. The resin was filtered and to it was added a solution of Boc-valine (1.74 g, 8 mmol), HBTU (0.5 M solution in DMF, 16 ml, 8 mmol) and DIPEA (2.75 ml, 16 mmol). The resin was shaken with this solution for 10 mins and reaction was monitored by the negative ninhydrin test, which indicated that a 99.65% coupling was achieved. The resin was washed with DMF, treated with TFA (2×10 ml, 1 min each) to give the deprotected valine on resin, and the procedure was repeated for Boc-isoleucine (99.99%) and Boc-proline (99.96%). The hydroxyethylamine isostere was introduced by shaking the resin with a solution of the ketobromide (X) (2.36 g, 5 mmol) and DIPEA (1.72 ml, 10 mmol) in DMF (16 ml) for 30 mins. The resultant ketone was reduced by shaking the resin, at room temperature for 1 hr, with sodium borohydride (0.6 g, 16.2 mmol) in THF (16 ml). Boc-asn was coupled to the peptide using the same procedure described above (99.66%). The weight of dried resin was 3.8 g (theoretical wt.=3.85 g). The peptide was cleaved from resin (0.8 g, 0.42 mmol) with HF, lyophilised and treated with a 0.1 M ammonium carbonate solution at room temperature for 15 mins, and again lyophilised to give 279 mg of a powder consisting of a diastereomeric mixture of peptides, ISMS 734(M+H). The diastereomeric mixture was deesterified without further purification by dissolving in a mixture of water (3 ml) and 0.57 M NaOH solution (2.16 ml, 12.3 mmol). The suspension was made homogeneous by the gradual addition of THF and the resulting solution stirred at room temperature for 30 mins. The mixture was neutralised with 1 M HCl to pH=7 and the solvent evaporated in vacuo. Purification by HPLC (gradient; water 0.1% TFA to 50:50 water/acetonitrile 0.1% TFA over 75 mins) gave a diastereomeric mixture of (W) (156 mg, 53% overall yield from beginning of the solid phase synthesis). ISMS; 706 (M+H).

[2(S),11'(S),8'(S)]-2-[11'-[6',9'-dioxo-8'-(ethanamide)-2'-oxa-7',10'-diazabicyclo[11.2.2] heptadeca-13',15',16'-triene]]-1-(N-(S)-prolyl-(S)-isoleucyl-(S)-valine amide)ethan-2-ol (V)

1a S. The diastereomeric mixture (W) (66 mg, 0.093 mmol) was dissolved in DMF (800 ml, C=1.16×10$^{-4}$ M), BOP reagent (61.6 mg, 0.14 mmol) and DIPEA (0.1 ml, 0.58 mmol) were added, and the solution stirred at room temperature for 1 hr. The solvent was evaporated in vacuo and the residue redissolved in distilled water (20 ml). Insoluble precipitate was filtered from the solution and the diastereomeric mixture was purified by reverse phase HPLC (gradient; water 0.1% TFA to 50:50 (water/0.1% TFA)/ (water 10%/acetonitrile 90%/TFA 0.1%) over 75 mins) to give a pure sample of both 1a R (18 mg, 28%) and 1a S (13 mg, 21%) as white powders, after lyophilisation. The two diastereomers were pure by analytical HPLC analysis (gradient; water 0.1% TFA to 50:50 (water/0.1% TFA)/ (water 10%/acetonitrile 90%/TFA 0.1%) over 50 mins), 1a S rt=39.9 min; 1a R rt=42.2 min. $^1$H NMR 1aS (H$_2$O/D$_2$O, 8:2, 313 K) δ 8.69 (br.s., 1H, Ile-NH), 8.22 (d, J=7.23Hz, 1H, Val-NH), 7.71 (d, J=9.8Hz, 1H, 10'-NH), 7.65 (br.s., 1H, Val-1°amide), 7.47 (br.s., 1H, Asn-1°amide), 7.21 (d, J=8.8Hz, 1H, Asn-NH), 7.20 (dd, J=2.1, 8.4Hz, 1H, H17'), 7.15 (dd, J=2.2, 8.4Hz, 1H, H14'), 7.09 (br.s., 1H, Val-1°amide), 7.00 (dd, J=2.7, 8.4Hz, 1H, H16'), 6.95 (dd, J=2.7, 8.4Hz, 1H, H15'); 6.72 (br.s., 1H, Asn-1°amide), 4.42–4.48 (m, 1H, H-3'), 4.29–4.38 (m, 2H, Asn-αCH & H-3'), 4.10–4.16 (m, 2H, Pro-αCH & H-2), 3.8 (m, 1H, Pro-δCH), 3.15–3.28 (m, 3H, Pro δCH & H-1), 3.12 (dd, J$_{H12'-H12'}$=3.5Hz, J$_{H12'-H11'}$=5.6Hz, 1H, H-12'), 2.78 (dd, J$_{H12'-H11'}$=13.5Hz, J$_{H12'-H12'}$=13.5Hz, 1H, H-12'); 0.94 (t, 3H, J=7.4Hz, Ile-δCH$_3$), 4.22–4.29 (m, 1H, H-11'), 4.19 (m, 1H, Val-αCH), 2.55 (m, 1H, Pro-βCH), 2.42–2.51 (m, 3H, Asn-βCH$_2$ & H-5'), 2.29 (ddd,J$_{H5'-H5'}$=16.2Hz, J$_{H5'-H4'}$=7.6Hz, J$_{H5'-H4'}$=3.6Hz,1H, H-5'), 2.19 (m, 1H, Pro-γCH), 1.98–2.14 (m, 5H, Val-βCH, Pro-βCH, Pro-γCH, Ile-γCH & H-4'), 1.89–1.98 (m, 1H, Ile-βCH), 1.51–1.61 (m, 1H, Ile-γCH), 1.20–1.30 (m, 1H, Ile-γCH), 1.02 (d, J=6.8Hz, 6H, Val-γ CH$_3$), 0.98 (d, J=6.8Hz, 3H, Ile-γCH$_3$). $^{13}$C NMR: (H$_2$O/ D$_2$O, 8:2, ref: EtOH); 10.59, 15.06, 18.21, 18.69, 23.08, 24.25, 24.98, 30.04, 30.23, 31.50, 35.63, 36.51, 38.86, 50.51, 53.84, 55.49, 58.19, 59.18, 59.74, 68.42, 68.78, 78.50, 114.98, 117.23, 117.83, 129.45, 131.27, 132.44, 156.90, 158.00, 171.93, 173.71, 174.50, 176.13. ISMS: 688(M+H).

3-[N-t-Butoxycarbonyl-(S)-isoleucinyl]amino-1-bromopropane (U)

To a solution of Boc-isoleucine hemihydrate (2.4 g, 10 mmol) and BOP reagent (4.42 g, 10 mmol) in dry THF (50 ml) was added DIPEA (1.29 g, 10 mmol) and the solution stirred for five mins. 3-Bromopropylamine.HBr (2.4 g, 11 mmol) and DIPEA (1.56 g, 12 mmol) were then added to the solution. After 30 mins, the solvent was removed under vacuum, the residue redissolved in ethyl acetate (100 ml) and thoroughly washed with 1 M hydrochloric acid (4×50 ml), saturated sodium bicarbonate (2×50 ml), brine (1×50 ml), and dried over sodium sulphate. Purification by column chromatography (silica; 40% ethyl acetate in hexane (R$_f$= 0.8)) provided the title compound (3.3 g, 94%) as a white solid. $^1$H NMR (CDCl$_3$): δ 6.50 (br.s, 1H, NH), 5.15 (br.s, 1H, Ile-NH), 3.85 (m, 1H, Ile-αCH), 3.40 (m, 4H, NCH$_2$, BrCH$_2$), 2.05 (m, 2H, CH$_2$), 1.85 (m,1H, Ile-βCH), 1.40 (m, 10H, Ile-γCH & (CH$_3$)$_3$), 1.10 (m, 1H, Ile-γCH), 0.90 (d, J=6.82 Hz, 3, Ile-γCH$_3$), 0.86 (t, J=7.73 Hz, 3H, Ile-δCH$_3$); ISMS (M+H) 351/353.

3-[N-t-Butoxycarbonyl-(S)-tyrosinyl-(S)-isoleucinyl] amino-1-bromopropane (T)

Compound (U) (3.51 g, 10 mmol) was dissolved in a solution of 25% TFA in DCM (10 ml) and stirred at room temperature for 30 mins. The solution was evaporated to dryness in vacuo and the residue evaporated from DCM three more times to remove residual traces of TFA. This residue was coupled to Boc-tyrosine (2.8 g, 10 mmol) using the procedure described for the synthesis of compound (U). The resultant product was purified by column chromatography (silica; 50% ethyl acetate in hexane ($R_f$=0.19)) as a colourless powder (4.9 g, 96%), mp 96–100° C. $^1$H NMR (CDCl$_3$): δ 6.7–7.1 (m, 6H, ArH, Ile-NH, NH), 5.15 (d, J=8.2 Hz, 1H, Tyr-NH), 4.30 (m, 1H, αCH), 4.2 (m, 1H, αCH), 3.35–3.50 (m, 1H, NCH), 3.40 (t, J=6.0 Hz, 2H, CH$_2$Br), 3.25 (m, 1H, NCH), 3.01 (dd, J=6.1, 13.6 Hz, 1H, Tyr-βCH), 2.93 (dd, J=6.1, 13.6 Hz, 1H, Tyr-βCH), 2.05 (m, 2H, CH$_2$), 1.9 (m, 1H, Ile-βCH), 1.4 (m, 10H, Ile-γCH, (CH$_3$)$_3$), 1.05 (m, 1H, Ile-γCH), 0.89 (d, J=6.32 Hz, 3H, Ile-γCH$_3$), 0.83 (t, J=7.37 Hz, 3H, Ile-δCH$_3$). ISMS 514/516 (M+H). HRMS calcd for C$_{23}$H$_{35}$N$_3$O$_5$(M-HBr), 433.2577; found 433.2573.

[11(S),8(S)]-11-(t-Butoxycarbonylamino)-7,10-dioxo-8-(1-methylpropyl)-2-oxa-6,9-diazabicyclo[11.2.2]heptadeca-13,15,16-triene (S)

The dipeptide (T) (1 g, 1.9 mmol) was added to a solution of sodium methoxide (0.1 g, 1.9 mmol) in methanol (40 ml) and stirred at room temperature for 96 hrs. The solution was evaporated to dryness and diluted with ethyl acetate (50 ml) washed with 1 M hydrochloric acid (1×25 ml), saturated sodium bicarbonate (1×25 ml), brine (1×25 ml). The organic phase dried and the solvent removed. The crude product was purified by column chromatography (silica; 50% ethyl acetate in hexane ($R_f$=0.17)) providing the title compound (0.63 g, 75%) as a colorless solid m.p. 248–252° C. $^1$H NMR (CDCl$_3$) δ 7.85 (m, 1H, NH-6), 7.16 (d, J=8.75Hz, 1H, ArH), 6.97 (d, 1H, J=7.50Hz, Ile-NH), 6.94 (d, J=7.50Hz, 1H, Tyr-NH), 6.83–6.90 (m, 3H, ArH), 4.38 (dt, $J_{H3-H3}$=12.5Hz $J_{H3-H4}$=5.00Hz, 1H, H-3), 4.22 (m, 1H, H-3), 4.14 (m, 1H, H-11), 3.45–3.55 (m, 2H, H-8 & H-5), 3.08 (dd, $J_{H12-H12}$=13.1Hz $J_{H11-H12}$=6.25Hz, 1H, H-12), 2.84 (m, 1H, H-5), 2.59 (m, 1H, H-12), 2.19 (m, 1H, H-4), 1.79 (m, 1H, H-4), 1.57 (m, 1H, Ile-βCH), 1.43–1.49 (m, 10H, Ile-γCH & t-Butyl), 0.98 (m, 1H, Ile-γCH), 0.83 (d, J=7.5Hz, 3H, Ile-γCH$_3$), 0.76 (d, J=6.3Hz, 3H, Ile-δCH$_3$). ISMS 434 (M+H). HRMS calcd for C$_{23}$H$_{35}$N$_3$O$_5$, 433.2577; found 433.2584.

Methyl-(S)-2-(t-butoxycarbonyl-(S)-valinyl)amino-3-phenyl Propanoate (R)

The title compound was prepared by coupling Boc-valine 2.17 g, 10 mmol) and phenylalanine methyl ester.HCl (2.3 g, 11 mmol) with BOP reagent according to the procedure described for (S). Purification of the crude residue by column chromatography (silica; 50% ethyl acetate in hexane) gave (R) (3.66 g, 97%) as a white solid. mp 103–106° C. $^1$H NMR (CDCl3): δ 7.1–7.35 (m, 5H, ArH), 6.35 (d, J=8.33 Hz, 1H, Phe-NH), 5.05 (d, J=7.7 Hz, 1H, Boc-NH), 4.85 (ddd, J=6.3, 6.3, 8.33 Hz, 1H, Phe-αCH), 3.9 (dd, J=7.7, 7.7 Hz, 1H, Val-αCH), 3.7 (s, 3H, OCH$_3$), 3.15 (dd, J=6.3, 14.1 Hz, 1H, Phe-βCH), 3.08 (dd, J=6.3, 14.1 Hz, 1H, Phe-βCH), 2.1 (m, 1H, Val-βCH), 1.45 (s, 9H, (CH$_3$)$_3$), 0.9 (d, J=5.0 Hz, 3H, Val-γCH$_3$), 0.85 (d, J=5.0 Hz, 3H, Val-γCH$_3$). ISMS 379 (M+H). HRMS calcd for C$_{20}$H$_{30}$N$_2$O$_5$, 378.2155; found 378.2151.

Methyl-(S)-2-(t-butoxycarbonyl-(S)-leucinyl-(S)-valinyl)amino-3-phenyl Propanoate (Q)

The dipeptide (R) (3.5 g, 9.2 mmol) was deprotected at the N-terminus with a solution of 25% TFA in DCM (10 ml) and the resultant amine coupled to Boc-leucine (2.49 g, 10 mmol) using the same procedure described for (U) above. Column chromatography (silica; 50% ethyl acetate in hexane) provided (Q) (4.3 g, 95%) as a white solid, mp 133–134° C. $^1$H NMR (CDCl$_3$): δ 7.00–7.30 (m, 5H, ArH), 6.70 (d, J=9.30 Hz, 1H, Val-NH), 6.55 (d, J=8.14 Hz, 1H, Phe-NH), 5.00 (d, J=8.20 Hz, 1H, Bocleu-NH), 4.85 (m, 1H, Phe-αCH), 4.27 (m, 1H, αCH), 4.10 (m, 1H, αCH), 3.50 (s, 3H, OCH$_3$), 3.10 (m, 2H, Phe-βCH$_2$), 2.10 (m, 1H, Val-βCH), 1.35–1.70 (m, 12H, (CH$_3$)$_3$, Leu-βCH$_2$, Leu-γCH), 0.70–1.00 (m, 12H, Val-γCH$_3$, Leu-δCH$_3$). ISMS 492 (M+H). HRMS calcd for C$_{26}$H$_{41}$N$_3$O$_6$, 491.2995; found 491.2996.

Methyl-(S)-2-(acetyl-(S)-leucinyl-(S)-valinyl)amino-3-phenyl Propanoate (P)

The tripeptide (P) was prepared by deprotection of (Q) (4 g, 8.1 mmol) with 25% TFA in DCM. The solvent and excess TFA was evaporated before diluting the residue with THF (100 ml). To the solution was added DIPEA (approx. 10 ml, excess) and DMAP (1 mole %). The resulting solution was then cooled to 0° C. in an ice-bath before adding acetic anhydride (5 equivalents). The mixture was warmed to room temperature and stirred for a further 30 mins. The solvent was removed and the residue redissolved in ethyl acetate (200 ml). The organic phase was washed with 1 M hydrochloric acid (1×50 ml), saturated sodium bicarbonate (1×50 ml), brine (1×50 ml), dried and the solvent evaporated. The product was recrystallised from ethyl acetate to provide the title compound (3.45 g, 99%) as a white solid mp 216–217° C. $^1$H NMR (CDCl$_3$): δ 7.10–7.30 (m, 6H, ArH, NH), 7.0 (d, J=9.0 Hz, 1H, NH), 6.5 (d, J=9.1 Hz, 1H, NH), 4.9 (m, 1H, Phe-αCH), 4.60 (m, 1H, Leu-αCH), 4.45 (m, 1H, Val-αCH), 3.70 (s, 3H, O—CH$_3$), 3.10 (m, 2H, Phe-βCH$_2$), 2.10 (m, 1H, Val-βCH), 2.00 (s, 3H, CH$_3$C(O)), 1.45–1.70 (m, 3H, Leu-γCH & Leu-CH$_2$), 0.90–1.05 (m, 12H, Val-γCH$_3$ & Leu-δCH$_3$). $^{13}$C NMR: (CDCl$_3$) 18.18, 18.99, 22.32, 22.92, 22.99, 24.82, 31.14, 35.07, 41.42, 51.74, 52.23, 52.26, 58.41, 127.11, 128.57, 129.17, 135.82, 170.20, 170.80, 171.84, 172.35. ISMS: 434 (M+H). HRMS calcd for C$_{23}$H$_{35}$N$_3$O$_5$, 433.2577; found 433.2576.

(S)-2-(Acetyl-(S)-leucinyl-(S)-valinyl)amino-1-diazo-3-phenyl Butan-2-one (O)

The tripeptide (O) (1 g, 2.3 mmol) was deesterified by dissolving in a mixture of dioxan (50 ml) and 1 M sodium hydroxide (10 ml), stirring at room temperature for 30 mins, before neutralising with 1 M hydrochloric acid. The solvent was removed under vacuum to yield (S)-2-(acetyl-(S)-leucinyl-(S)-valinyl)amino-3-phenyl propanoic acid (0.92 g, 95%). This compound (0.87 g, 2 mmol) and N-methyl piperidine (0.25 g, 2.5 mmol) was dissolved in a mixture of dry THF (50 ml) and DMF (5 ml) at room temperature under an atmosphere of nitrogen. The resultant solution was cooled to −15° C. and ethyl chloroformate (0.24 g, 2.2 mmol) added. After stirring for 5 mins an ethereal solution of diazomethane (excess) was added and the mixture allowed to warm gradually to room temperature over 2 hrs. The excess diazomethane was then removed by purging the solution with a stream of N$_2$ for 20 mins and evaporated to dryness. The residue was redissolved in ethyl acetate (100 ml), washed with saturated sodium carbonate (2×50 ml), brine (1×50 ml), and dried over sodium sulphate. The product was purified on a silica column pretreated with triethylamine to give the diazoketone (O) (0.81 g, 92%) as a light yellow solid. mp 220–230° C. (dec.). $^1$H NMR (d$_6$ DMSO): δ 8.30 (d, J=6.70 Hz, 1H, Phe-NH), 8.03 (d, J=7.05 Hz, 1H, Leu-NH), 7.6 (d, J=8.9 Hz, 1H, Val-NH), 7.23 (m, 5H, ArH), 6.03 (br.s, 1H, CHN$_2$), 4.48 (m, 1H, Phe-αCH), 4.27 (m, 1H, Leu-αCH), 4.05 (dd, J=7.3, 8.9 Hz, 1H, Val-αCH), 3.02 (dd, J=4.8, 16.1 Hz, 1H, Phe-βCH), 2.75 (dd, J=4.8, 16.1 Hz, 1H, Phe-βCH), 1.85 (m, 1H, Val-βCH), 1.83 (s, 3H, acetyl), 1.55 (m, 1H, Leu-γCH), 1.36 (m, 1H, Leu-βCH$_2$), 0.86 (d, J=6.73 Hz, 3H, Leu-δCH$_3$), 0.81 (d, J=6.73 Hz, 3H, Leu-δCH$_3$), 0.75 (d, J=4.8 Hz, 3H, Val-γCH$_3$), 0.72 (d, J=4.8 Hz, 3H, Val-γCH$_3$); ISMS 444 (M+H). HRMS calcd for C$_{23}$H$_{33}$N$_5$O$_4$(M—N$_2$), 415.2583; found 415.2578.

(S)-2-(Acetyl-(S)-leucinyl-(S)-valinyl)amino-1-bromo-3-phenyl Butan-2-one (N)

The diazoketone (O) (0.75 g, 1.7 mmol) was dissolved in ethyl acetate (10 ml) and treated with HBr under identical conditions used for the preparation of 5. Purification by column chromatography (silica; 50% ethyl acetate in hexane) afforded the ketobromide (X) (0.82 g, 99%) as a colorless solid: mp 184–185° C.; $^1$H NMR (d$_6$ DMSO): δ 8.5 (d, J=6.8 Hz, 1H, Phe-NH), 8.0 (d, J=6.6 Hz, 1H, Leu-NH), 7.7 (d, J=7.0 Hz, 1H, Val-NH), 7.2 (m, 5H, ArH), 4.67 (m, 1H, Phe-αCH), 4.38 (d, J=14.6 Hz, 1H, CHBr), 4.30 (d, J=14.6 Hz, 1H, CHBr), 4.25 (m, 1H, Leu-αCH), 4.03 (m, 1H, Val-αCH), 3.11 (dd, J=6.1, 15.9 Hz, 1H, Phe-βCH), 2.78 (dd, J=6.1, 15.9 Hz, 1H, Phe-βCH), 1.8 (s, 3H, acetyl), 1.55 (m, 1H, Leu-γCH), 1.35 (m, 2H, Leu-βCH$_2$), 0.86 (d, J=6.5 Hz, 3H, Leu-δCH$_3$), 0.81 (d, J=6.5 Hz, 3H, Leu-δCH$_3$), 0.76 (d, J=6.7 Hz, 3H, Val-γCH$_3$), 0.72 (d, J=6.7 Hz, 3H, Val-γCH$_3$); ISMS 496/498 (M+H).

[2(R),3(S),11'(S),8'(S)]-3-[-Acetyl-(S)-leucinyl-(S)-valinyl]amino-4-phenyl-1-[11'-[7',10'-dioxo-8'-(-1-methylpropyl)-2'-oxa-6',9'-diazabicyclo[11.2.2]heptadeca-13',15',16'-triene]amino]butan-2-ol (M)

The macrocycle (S) (30 mg, 69 μmol) was deprotected at the N-terminus with 25% TFA in DCM according to the procedure used for the synthesis of (T). The residue was diluted with DCM (50 ml), washed with 1 M sodium hydroxide to generate the free amine, and the solvent evaporated. The residue was redissolved in THF (5 ml) to which DIPEA (0.015 ml, 76 μmol) and 17 (37 mg, 76 μmol) was added, the solution stirred at room temperature for 4 hs. solvent evaporated in vacuo and the residue redissolved in ethyl acetate (20 ml), washed with 0.5 M hydrochloric acid (5 ml), dried and the solvent removed. The ketone intermediate was not purified but reduced directly to the title compound with NaBH$_4$ (40 mg, 100 mmol) in MeOH (10 ml), stirred at room temperature for 30 m before quenching the reaction with 1 M hydrochloric acid (1 ml). Subsequent purification of the crude residue by reverse phase HPLC [gradient: (water 0.1% TFA to 40:60 (water/0.1% TFA)/(water 10%/acetonitrile 90%/TFA 0.1%) over 50 mins), rt=55.8 mins and lyophilisation gave 2a as a colourless powder (7 mg, 15%) and the 2(S) diastereomer as the minor product. $^1$H NMR (CD$_3$OH, 293 K) δ 8.30 (d, J=6.05Hz, 1H, Ile-NH), 7.85 (m, 1H, 6'-NH), 7.73 (d, J=5.8Hz, 1H, Val-NH), 7.70 (d, J=8.9Hz, 1H, Phe-NH), 7.34 (d, J=7.6Hz, 1H, Leu-NH), 7.23 (m, 4H, Ph), 7.17 (m, 1H, Ph), 7.11 (dd, J=8.3, 1.9Hz, 1H, H-14'), 6.96 (dd, J=8.4, 1.9Hz, 1H, H-17'), 6.88 (dd, J=8.3, 2.6Hz, 1H, H-16'), 6.83 (dd, J=8.3, 2.6Hz, 1H, H-15'), 4.38 (m, 1H, H-3'), 4.20–4.26 (m, 2H, Ile-α(CH) & H-3'), 4.13 (m, 2H, H-11' & H-2), 3.81 (m, 2H, Val-αCH & H-1), 3.54 (m, 1H, H-5'), 3.45 (m, 1H, Leu-αCH), 3.39 (dd, J$_{H11'-H12'}$=7.0Hz, J$_{H12'-H12'}$=12.1Hz, 1H, H-12'), 3.28 (m, 1H, H-1), 3.08 (dd, J$_{H4-H4}$=12.7Hz, J$_{H4-H3}$=1Hz, 1H, H-4), 3.00 (dd, J$_{H4-H4}$=12.7Hz, J$_{H4-H3}$=6.0Hz, 1H, H-4), 2.79 (m, 2H, H-5'& H-12'), 2.70 (dd, J$_{H1-H1}$=14.0Hz, J$_{H1-H2}$=11.0Hz, 1H, H-1), 2.26 (m, 1H, H-4'), 2.04 (s, 3H, acetyl), 1.80–1.85 (m, 1H, Val-βCH), 1.72 (m, 1H, H-4'), 1.61–1.64 (m, 1H, Leu-γCH), 1.53–1.59 (m, 2H, Leu-βCH & Ile-βCH), 1.43–1.49 (m, 2H, Leu-βCH & Ile-γCH), 0.94–1.00 (m, 1H, Ile-γCH$_3$), 0.93 (d, J=6.5Hz, 3H, Leu-δCH$_3$), 0.88 (d, J=6.5Hz, 3H, Leu-δCH$_3$), 0.85 (t, J=7.4Hz, 3H, Ile-δCH$_3$), 0.76 (d, J=6.7Hz, 3H, Ile-γCH$_3$), 0.74 (d, J=6.7Hz, 3H, Val-γCH$_3$), 0.59 (d, J=6.7Hz, 3H, Val-γCH$_3$). $^{13}$C NMR (CD$_3$OH): 11.69, 14.97, 18.82, 19.29, 21.79, 22.52, 23.32, 25.74, 26.47, 27.46, 30.86, 36.60, 37.25, 37.64, 39.97, 41.12, 50.72, 54.28, 54.75, 59.99, 62.17, 63.82, 68.52, 70.74, 118.57, 118.73, 127.53, 127.90, 129.46, 130.05, 130.43, 132.35, 139.36, 159.98, 167.78, 171.39, 174.19, 174.79, 175.67. ISMS: 751 (M+H). HMRS calcd for C$_{41}$H$_{62}$N$_6$O$_7$, 750.4680; found 750.4682.

[2R,3S,11'S]-3-[[(Acetyl-(S)-leucinyl))-(S)-valinyl]amino]-4-phenyl-1-[7',10'-dioxo-8'-(-1-methylpropyl)-2'-oxa-6',9'-diazabicyclo[11.2.2]heptadeca-13',15',16'-triene-11-yl]amino]butan-2-ol (L)

This compound was synthesised using our previously described procedure (Abbenante et al., 1995, J. Am. Chem. Soc. 17 10220–10226).

[2R,3S,12'S,9'S]-3-[[(Acetyl-(S)-leucinyl)-(S)-valinyl]amino]-4-phenyl-1-[8',11'-dioxo-9'-(-1-methylpropyl)-2'-oxa-7',10'-diazabicyclo[12.2.2]octadeca-14',16',17'-triene-12-yl]amino]butan-2-ol (K)

To a stirred solution of 12-(t-butoxycarbonylamino)-8,11-dioxo-9-(1-methylpropyl)-2-oxa-7,10-diazabicyclo-[12.2.2] octadeca-14,16,17-triene 137. A synthesis of cycle 136 has been reported (Abbenante, 1995, et al., supra). 136 was made in three steps by coupling 3-bromopropylamine to Boc-Ile (94%) with BOP reagent, deprotecting (TFA), coupling with Boc-Tyr (96%) and cyclization with base (50%). 12-(t-Butoxycarbonylamine)-8,11-dioxo-9-(1-methylpropyl)-2-oxa-7,10-diazabicyclo[12.2.2.]octadeca-14,16,17-triene 137 was made similarly by coupling 4-aminobutanol to Boc-Ile, converting the hydroxyl to bromide with CBr$_4$/PPh$_3$[16], deprotecting (TFA), coupling to Boc-Tyr adn recyclizing (~50% yield overall) (30 mg, 67 μmol) in THF (5 ml) was added DIPEA (4 eq.) and 3-(S)-[Acetyl-(S)-leucinyl-(S)-valinyl]amino-1-bromo-4-phenyl-butan-2-one (Abbenante, 1995, et al., supra) (33 mg, 67 μmol). The reaction mixture was stirred for 60 mins at room temperature. The mixture was diluted with ethyl acetate (50 ml), washed with 1 M HCl dried and the solvent removed in vacuo. The resultant ketoethylamine was dissolved in methanol (10 ml), and reduced with sodium borohydride (100 μmol) by stirring the solution at −5° for 30 mins. The reaction was quenched with acetic acid, evaporated to dryness and the crude residue purified by reverse phase HPLC [gradient: (water/0.1% TFA) to 0:100 (water/0.1% TFA): (water 10%/acetonitrile 90%/TFA 0.1%) over 35 mins (flow rate 1.5 ml/min). Only the R-diastereoisomer was isolated (6 mg, 11.7%) retention time=21.15 mins. $^1$H nmr (500 MHz, 290K, CD$_3$OD): δ 8.33 (d, J=5.0 Hz, 1H, Leu-NH), 8.01 (m, 1H, NH), 7.76 (d, J=5.0 Hz, 1H, Val-NH), 7.65–7.73 (m, 2H, Ile-NH, Phe-NH), 6.80–7.30 (m, 9H, ArH), 4.32 (m, 1H, H3'), 4.25 (m, 1H, Leu-αCH), 4.13–4.19 (m, 3H, Tyr-αCH, Phe-αCH, H3'), 3.80–3.87 (m, 3H, Val-αCH, Ile-αCH, H2), 3.46 (m, 1H, H6'), 3.30 (m, 2H, Phe-βCH, Tyr-βCH), 3.00–3.43 (m, 2H, H1, H1), 2.86 (m, 1H, Tyr-βCH), 2.73 (m, 1H, Phe-βCH), 2.63 (m, 1H, H6'), 2.06 (s, 3H, acetyl), 1.97 (m, 1H, H4'), 1.85 (m, 1H, Val-βCH), 1.34–1.75 (m, 8H, H4', H5', H5', Leu-γCH, Leu-βCH$_2$, Ile-βCH, Ile-γCH), 1.04 (m, 1H, Ile-γCH), 0.95 (d, J=6.0 Hz, 3H, Leu-δCH$_3$), 0.88 (d, J=6.0 Hz, 3H, Leu-δCH$_3$), 0.87 (m, 3H, Ile-δCH$_3$), 0.81 (d, J=6.0 Hz, 3H, Ile-γCH$_3$), 0.75 (d, J=5.0 Hz, 3H, Val-γCH$_3$), 0.61 (d, J=5.0 Hz, 3H, Val-γCH$_3$). ISMS 765 (M+H). HRMS calculated for $C_{42}H_{64}N_6O_7$, 764.4837; found 764.4840.

[2R, 3S, 11'S, 8'S]-3-[t-butoxycarbonyl]amino-4-phenyl-1-[11'-[7', 10'-dioxo-8'-(1-methylpropyl)-2'-oxa-6',9'-diazabicyclo[11.2.2]heptadeca-13',15',16'-triene]amino]butan-2-ol (J)

11-(t-Butoxycarbonylamino)-7,10-dioxo-8-(1-methylpropyl)-2-oxa-6,9-diazabicyclo[11.2.2]-heptadeca-13,15,16-triene 136. 137 was made in 3 steps by coupling 3-bromopropylamine to Boc-Ile (94%) with BOP reagent deprotecting (TFA), coupling with Boc-Tyr (96%), and cyclization with base (50%). 12-(t-Butoxycarbonylamino)-8,11-dioxo-9-(1-methylpropyl)-2-oxa-7,10-diazabicyclo[12.2.2]octadeca-14,16,17-triene 137 was made similarly by coupling 4-aminobutanol to Boc-Ile, converting the hydroxyl to bromide with $CBr_4/PPh_3^{16}$, deprotecting (TFA), coupling to Boc-Tyr and cyclizing (~50% yield overall) (30 m g, 69 μmol) was deprotected by stirring in a solution of 25% TFA in DCM at room temperature for 15 mins. The TFA was evaporated in vacuo and the residue dissolved in saturated NaCHO$_3$ solution (10 ml) and extracted with ethyl acetate (3×10 ml). The organic phase was dried and evaporated and the residue redissolved in DMF (1 ml) and BocPhe epoxide (Rich et al., 1991, J. Med. Chem. 34 1222–1225) (12 mg, 46 μmol) added. The resultant mixture was heated to 70° for 12 hrs. The crude residue was purified by reverse phase HPLC [gradient: (water/0.1% TFA) to 50:50 (water/0.1% TFA): (water 10%/acetonitrile 90%/TFA 0.1%) over 60 mins] to give the title compound (5 mg, 18.2%), retention time=56.20 mins, as a white powder after lyophilisation. $^1$H NMR (500 MHz, 290K, CD$_3$OD): δ 7.81 (m, 1H, NH), 6.91–7.41 (m, 10H, ArH, Ile-NH), 6.44 (d, J=9.0 Hz, 1H, Phe-NH), 6.06 (m, 1H, Tyr-NH), 4.44 (m, 1H, H3'), 4.27 (m, 1H, H3'), 3.83 (m, 1H, H2), 3.69 (m, 2H, Tyr-αCH, Phe-αCH), 3.51 (m, 1H, Ile-αCH), 3.40 (m, 1H, H5'), 3.10–3.17 (m, 2H, Phe-βCH, Tyr-βCH), 3.03 (m, 1H, H1), 2.86–2.92 (m, 2H, H1, H5'), 2.53–2.61 (m, 2H, Phe-βCH, Tyr-βCH), 2.22 (m, 1H, H4'), 1.84 (m, 1H, H4'), 1.56 (m, 1H, Ile-βCH), 1.38 (m, 1H, Ile-γCH), 1.25 (s, 9H, (CH$_3$)$_3$), 0.96 (m, 1H, Ile-γCH), 0.83 (t, J=5.0 Hz, 3H, Ile-δCH$_3$), 0.73 (d, J=5.0 Hz, 3H, Ile-γCH$_3$). ISMS 597 (M+H). HRMS calculated for $C_{33}H_{48}N_4O_6$, 596.3574; found 596.3579.

[2S, 11'S, 8'S]-2-[t-butoxycarbonyl]amino-3-phenyl-1-[11'-[7',10'-dioxo-8'-(-1-methylpropyl)-2'-oxa-6',9'-diazabicyclo[11.2.2]heptadeca-13',15',16'-triene]amino]propane (I)

The macrocycle 136 was made in 3 steps by coupling 3-bromopropylamine to Boc-Ile (94%) with BOP reagent, deprotecting (TFA), coupling with Boc-Tyr (96%), and cyclization with base (50%). 12-(t-Butoxycarbonylamino)-8,11-dioxo-9-(1-methylpropyl)-2-oxa-7,10-diazabicyclo[12.2.2.]octadeca-14,16,17-triene 137 was made similarly by coupling 4-aminobutanol to Boc-Ile, converting the hydroxyl to bromide with $CBr_4/PPh_3^{16}$, deprotecting (TFA), coupling to Boc-Tyr and cyclizing (~50% yield overall) (30 mg, 69 μmol) was deprotected as above and the resultant amine was added to a solution of BocPhe aldehyde (Fehrentz, J-A. & Castro, B., 1983, Synthesis 676–678) (17 mg, 69 μmol), MgSO$_4$ (100 mg) and sodium cyanoborohydride (47 mg, 76 μmol) in THF/1% acetic acid solution 5 ml). The mixture was stirred overnight at room temperature and quenched with 1 M HCl (1 ml), evaporated in vacuo and the crude residue purified by reverse phase HPLC [gradient: (water/0.1% TFA) to 0:100 (water/0.1% TFA):(water 10%/acetonitrile 90%/TFA 0.1%) over 35 mins (flow rate 1.5 ml/min), retention time=21.24 mins. $^1$H NMR (500 MHz, 290K, CD3OD): δ 7.90 (m, 1H, NH), 6.82–7.37 (m, 11H, ArH, Phe-NH, Ile-NH), 6.3 (m, 1H, Tyr-NH), 4.39 (m, 1H, H3'), 4.25 (m, 1H, H3'), 4.08 (m, 2H, Tyr-αCH, Phe-αCH), 3.57 (m, 1H, H5'), 3.46 (m, 1H, Ile-αCH), 3.34 (m, 1H, Tyr-βCH), 2.68–3.07 (m, 6H, Tyr-βCH, Phe-βCH$_2$, H1, H1, H5'), 2.27 (m, 1H, H4'), 1.76 (m, 1H, H4'), 1.50 (m, 1H, Ile-βCH), 1.38–1.42 (m, 10H, Ile-γCH, (CH$_3$)$_3$), 0.92 (m, 1H, Ile-γCH), 0.86 (t, J=6.0 Hz, 3H, Ile-δCH$_3$), 0.73 (d, J=5.0 Hz, 3H, Ile-γCH$_3$). ISMS 567 (M+H). HRMS calculated for $C_{32}H_{46}N_4O_5$, 566.3468; found 566.3447.

[2R, 3S, 11'S, 8'S]-3-[3S-tetrahydrofuranyloxy]amino-4-phenyl-1-[11'-[7',10'-dioxo-8'-(1-methylpropyl)-2'-oxa-6',9'-diazabicyclo[11.2.2]heptadeca-13',15',16'-triene]amino]butan-2-ol (H)

The macrocycle 136 (30 mg, 69 μmol) was deprotected as above and the free amine reacted with 3-(S)-(3'-(S)-tetrahydrofuranyloxycarbonyl)amino-1-bromo-4-phenyl-butan-2-one (3-(S)-(3'(S)-tetrahydrofuranyloxycarbonyl)amino-1-bromo-4-phenyl-butan-2-one was synthesised in three steps by reaching S-3-hydroxytetrahydrofuran and phenylalanine methyl ester.HCl according to the procedure of Ghosh et al., 1992, Tet. Lett. 33 2781–2784 (78%), de-esterification of the resultant ester, preparation of the diazoketone (Abbenante et al., 1995, supra) (95%) and reaction with HBr (91%) (Abbenante et al., 1995, supra) as described for the synthesis of 5. Subsequent purification by reverse phase HPLC [gradient: (water/0.1% TFA) to 0:100 (water/0.1% TFA):(water 10%/acetonitrile 90%/TFA 0.1%) over 35 mins (flow rate 1.5 ml/min, gave the title compound (6 mg, 14.2%) as a white powder, retention time=18.03 mins. The reaction gave only a very small amount of the 2(S) diastereomer which could not be isolated. $^1$H NMR (500 MHz, 290K, CD3OD): δ 7.85 (m, 1H, NH), 7.37 (d, J=5.5 Hz, 1H, Ile-NH), 6.83–7.32 (m, 9H, ArH), 6.44 (d, J=9.0 Hz, 1H, Phe-NH), 5.05 (m, 1H, Furan-H), 4.40 (m, 1H, H3'), 4.26 (m, 1H, H3'), 3.64–3.89 (m, 6H, H2, Tyr-αCH, Phe-αCH, 3 Furan-H), 3.58 (m, 1H, H5'), 3.47–3.53 (m, 2H, Ile-αCH, Furan-H), 3.22 (m, 1H, Phe-βCH), 3.12 (m, 1H, H1), 3.00 (m, 1H, H1), 2.91 (m, 2H, Tyr-βCH, Phe-βCH), 2.78–2.84 (m, 2H, Tyr-βCH, H5'), 2.26 (m, 1H, H4'), 2.10 (m, 1H, Furan-H), 1.93 (m, 1H, Furan-H), 1.76 (m, 1H, H4'), 1.57 (m, 1H, Ile-βCH), 1.42 (m, 1H, Ile-γCH), 0.99 (m, 1H, Ile-γCH), 0.86 (t, J=5.5 Hz, 3H, Ile-δCH$_3$), 0.78 (d, J=5.0 Hz, 3H, Ile-γCH$_3$), ISMS 611 (M+H).

[2R, 3S, 11'S, 8'S]-3-[3-methylphenyl]amino-4-phenyl-1-[11'-[7',10'-dioxo-8'-(1-methylpropyl)-2'-oxa-6',9'-diazabicyclo[11.2.2]heptadeca-13',15',16'-triene]amino]butan-2-ol (G)

The macrocycle 136 (30 mg, 69 μmol) was deprotected as above and the free amine reacted with 3-(S)-(3'-methylphenylcarbonyl)amino-1-bromo-4-phenyl-butan-2-one (3-(S)-(3'-methylphenylcarbonyl)amino-1-bromo-4-phenyl-butan-2-one was synthesized in three steps by coupling m-toluic acid and phenylalanine methyl ester.HCl with BOP (100%), de-esterification of the resultant ester with base, preparation of the diazoketone (Abbenante et al., 1995, supra) (60%) and reaction with HBr (91%) (Abbenante et al., 1995, supra) (24 mg, 69 μmol) as described for the synthesis of 88. Purification by reverse phase HPLC [gradient: (water/0.1% TFA) to 0:100 (water/ 0.1% TFA):(water 10%/acetonitrile 90%/TFA 0.1%) over 35 mins (flow rate 1.5 ml/min), gave a diastereomeric mixture of 92 (7 mg, 16.5%), retention time=20.48 mins. The NMR spectra indicated the presence of a 1:1 mixture of diastereomers by a doubling of all resonances at 290K. The spectra was consistent with the structure. Several attempts to separate diastereomers by reverse phase HPLC were unsuccessful and the diastereomeric mixture was tested for HIV-1 PR inhibition. ISMS 615 (M+H), HRMS calculated for $C_{36}H_{46}N_4O_5$, 614.3468; found 614.3467.

[2R, 3S, 11'S, 8'S]-3-[2-quinolinecarbonyl]amino-4-phenyl-1-[11'-[7',10'-dioxo-8'-(1-methylpropyl)-2'-oxa-6',9'-diazabicyclo[11.2.2]heptadeca-13',15',16'-triene]amino]butan-2-ol (E)

Compound 89 (3 mg, 5 μmol) was deprotected with 25% TFA in dichloromethane (1 ml) over 15 mins and evaporated in vacuo. The residue was dissolved in DMF (1 ml) and to it added quinaldyl-(S)-valine (Quinaldyl-(S)-valine was synthesised by the BOP coupling of quinoline-2-carboxylic acid with Valine methyl ester.HCl followed by de-esterification with NaOH) (1.6 mg, 6 μmol), BOP (2.6 mg, 6 μmol) and DIPEA (3 eq.) and stirred for 1 hr at room temperature. The solvent was evaporated under reduced pressure and the residue purified by reverse phase HPLC [gradient: (water/ 0.1% TFA) to 0:100 (water/0.1% TFA):(water 10%/ acetonitrile 90%/TFA 0.1%) over 35 mins, to give 93 (3 mg, 79%), retention time=22.42 mins, as a white powder. $^1$H NMR (500 MHz, 290K, CD$_3$OD): δ 8.77 (d, J=7.48 Hz, 1H, Val-NH), 8.44 (d, J=8.45 Hz, 1H, ArH), 8.25 (d, J=8.89 Hz, 1H, Phe-NH), 8.21 (d, J=8.45 Hz, 1H, ArH), 8.16 (d, J=8.45 Hz, 1H, ArH), 7.99 (d, J=8.45 Hz, 1H, ArH), 7.83–7.91 (m, 2H, ArH, NH), 7.71 (m, 1H, ArH), 7.31 (d, J=7.33Hz, 1H, Ile-NH), 6.74–7.24 (m, 11H, ArH), 4.36 (m, 1H, H3'), 4.24 (m, 1H, H3'), 4.11–4.17 (m, 3H, Val-αCH), Tyr-αCH, Phe-αCH), 3.78 (m, 1H, H2), 3.56 (m, 1H, H5'), 3.47 (m, 1H, Ile-αCH), 3.29–3.33 (m, 2H, Phe-βCH, Tyr-βCH), 3.10 (m, 1H, H1), 3.03 (m, 1H, H1), 2.79 (m, 1H, H5'), 2.53–2.62 (m, 2H, Phe-βCH, Tyr-βCH), 2.25 (m, 1H, H4'), 2.01 (m, 1H, Val-βCH), 1.73 (m, 1H, H4'), 1.58 (m, 1H, Ile-βCH), 1.43 (m, 1H, Ile-γCH), 0.97 (m, 1H, Ile-γ 7.33 Hz, 3H, Ile-δCH$_3$), 0.77 (d, J=6.74 Hz, 3H, Ile-γCH$_3$), 0.71 (d, J=6.62 Hz, 3H, Val-γCH$_3$). ISMS 751 (M+H). HRMS calculated for $C_{43}H_{54}N_6O_6$, 750.4105; found 750.4097.

In summary, we have described a general strategy for developing a structural and functional mimic of a tri- or tetra-peptide component of an inhibitor of HIV-1 protease. The ease of synthesis variability of side chains, hydrolytic stability, ease of incorporating chiral centres, water and lipid solubility make this an attractive strategy for mimicking enzyme inhibitors.

Scheme 1
Synthesis of N-terminal cyclic inhibitors 2-17

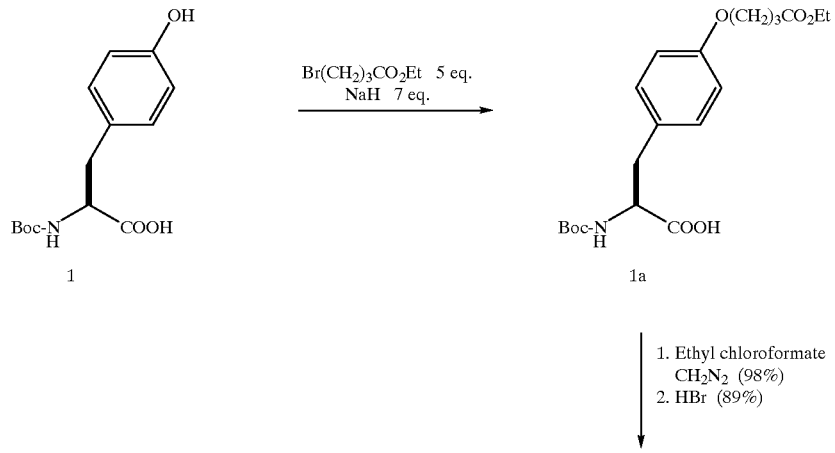

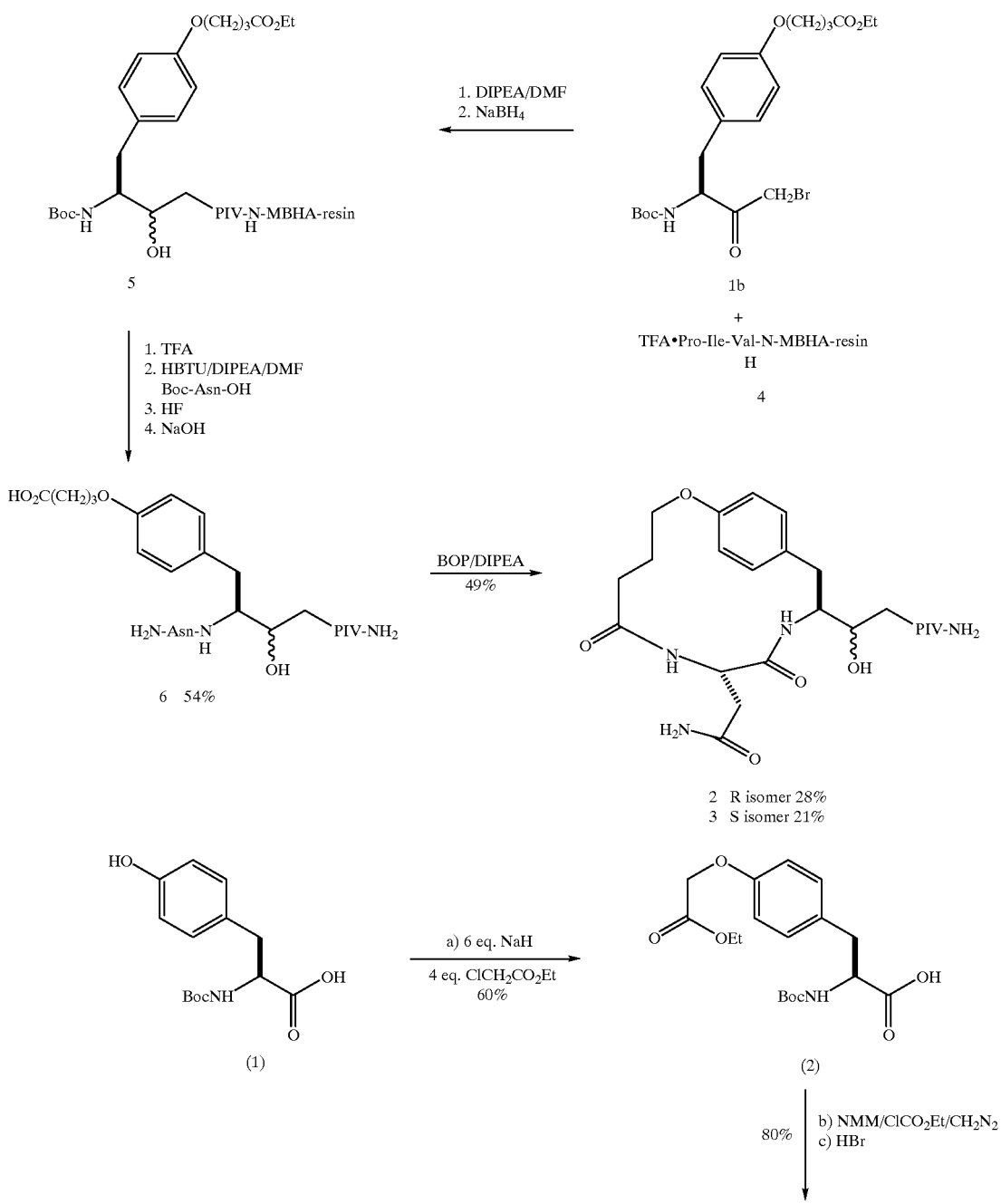

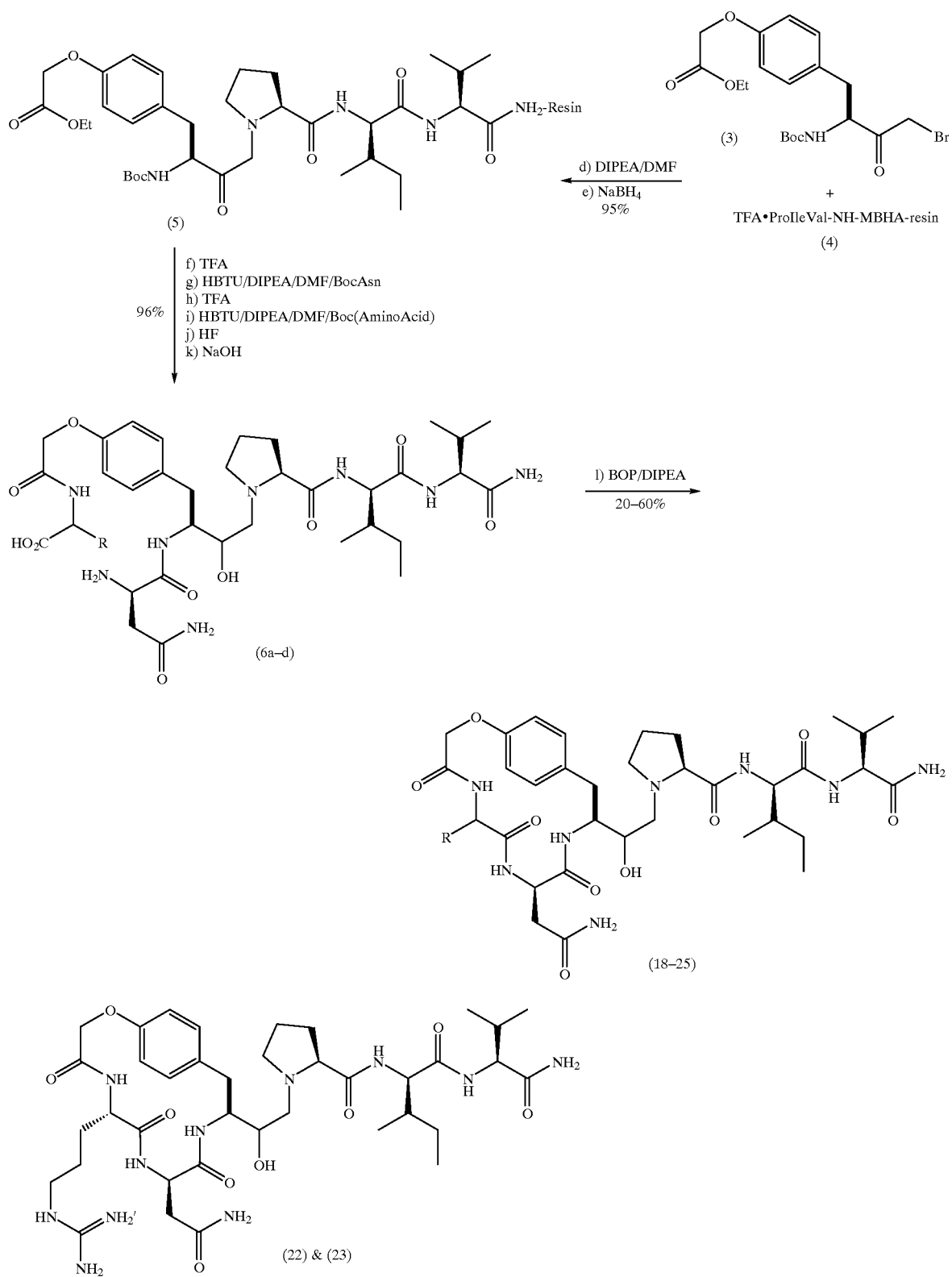

-continued
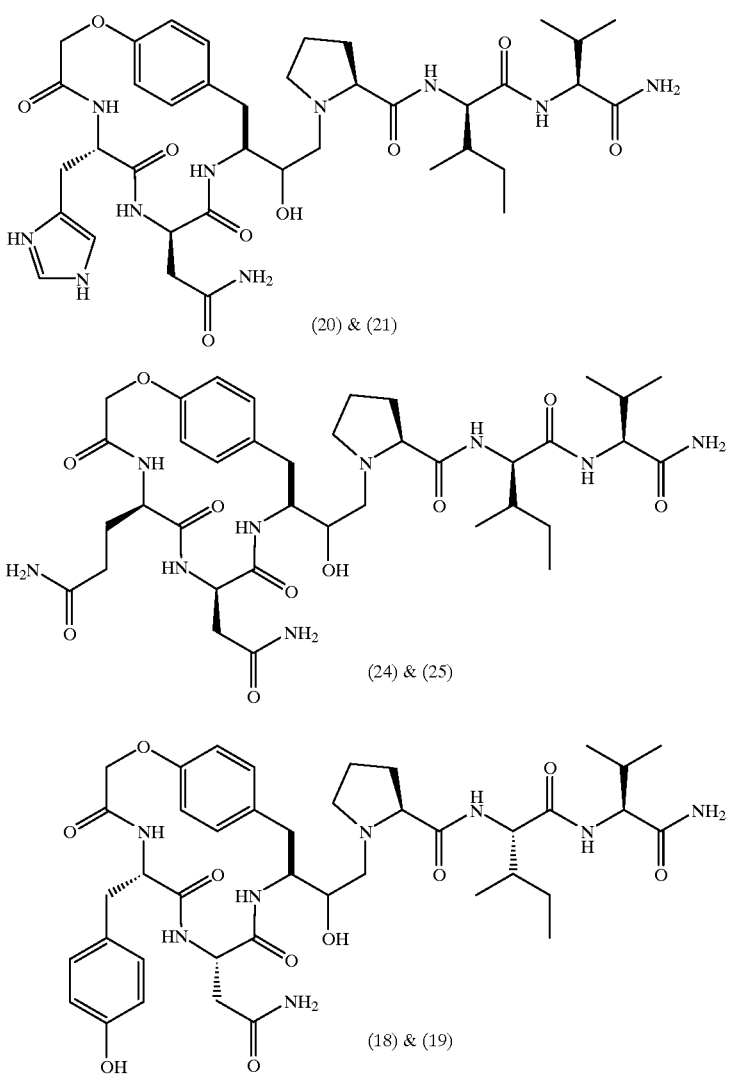
(20) & (21)
(24) & (25)
(18) & (19)
Scheme 2
Synthesis of N-terminal cyclic Inhibitors 26–39
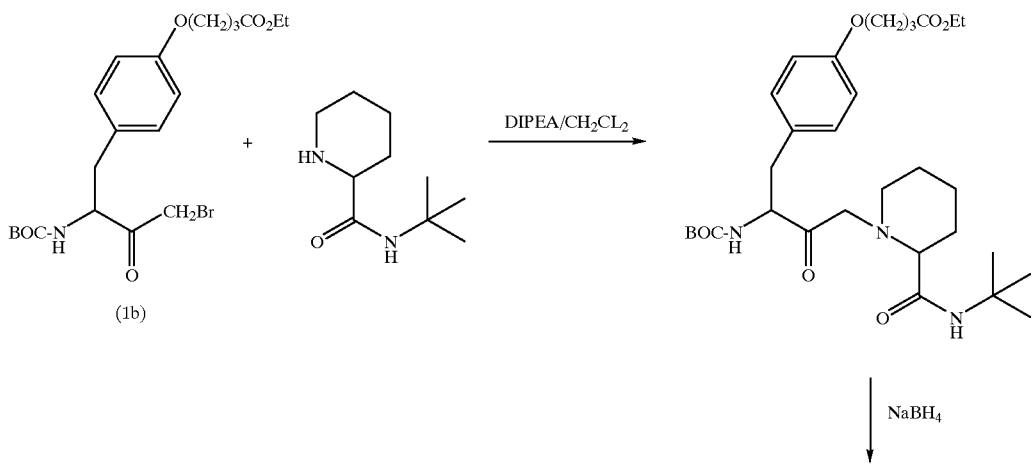

33 34
-continued
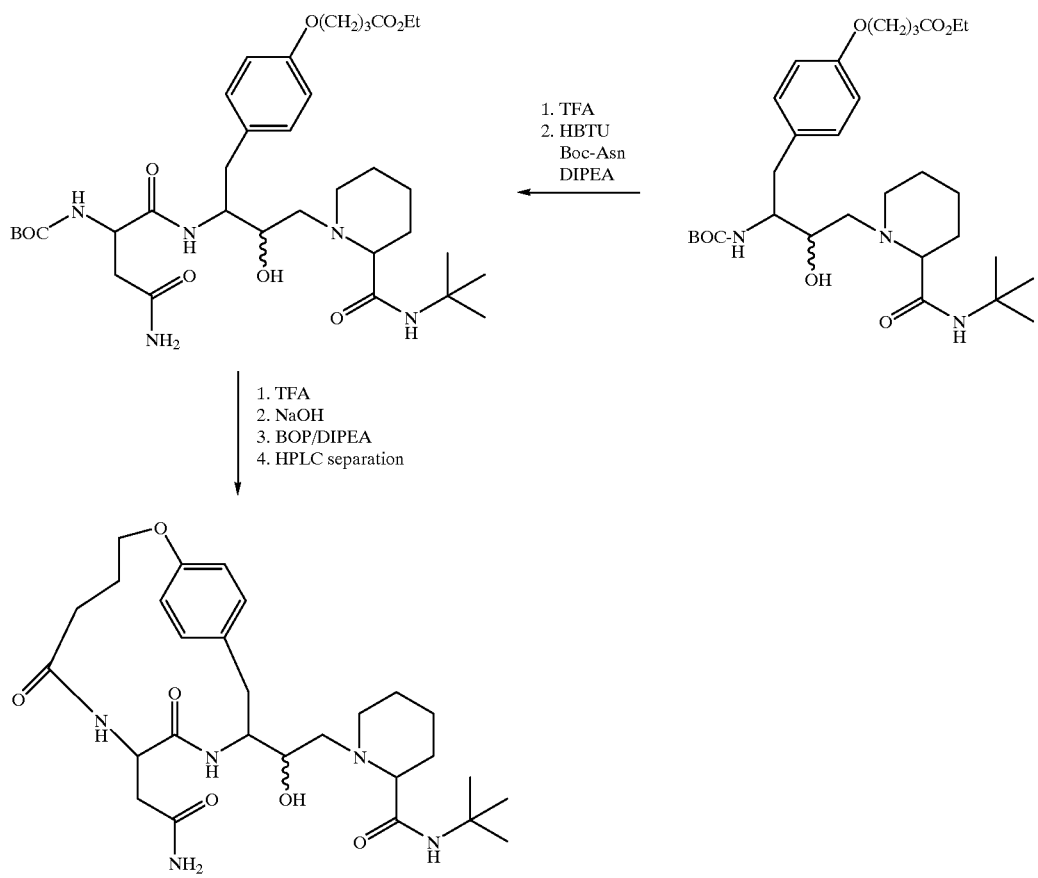
Scheme 3
Synthesis of C-terminal cyclic inhibitors 40 & 41
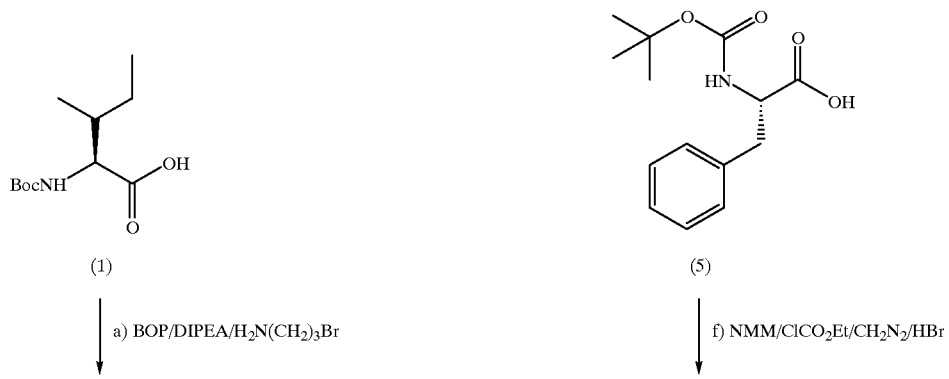

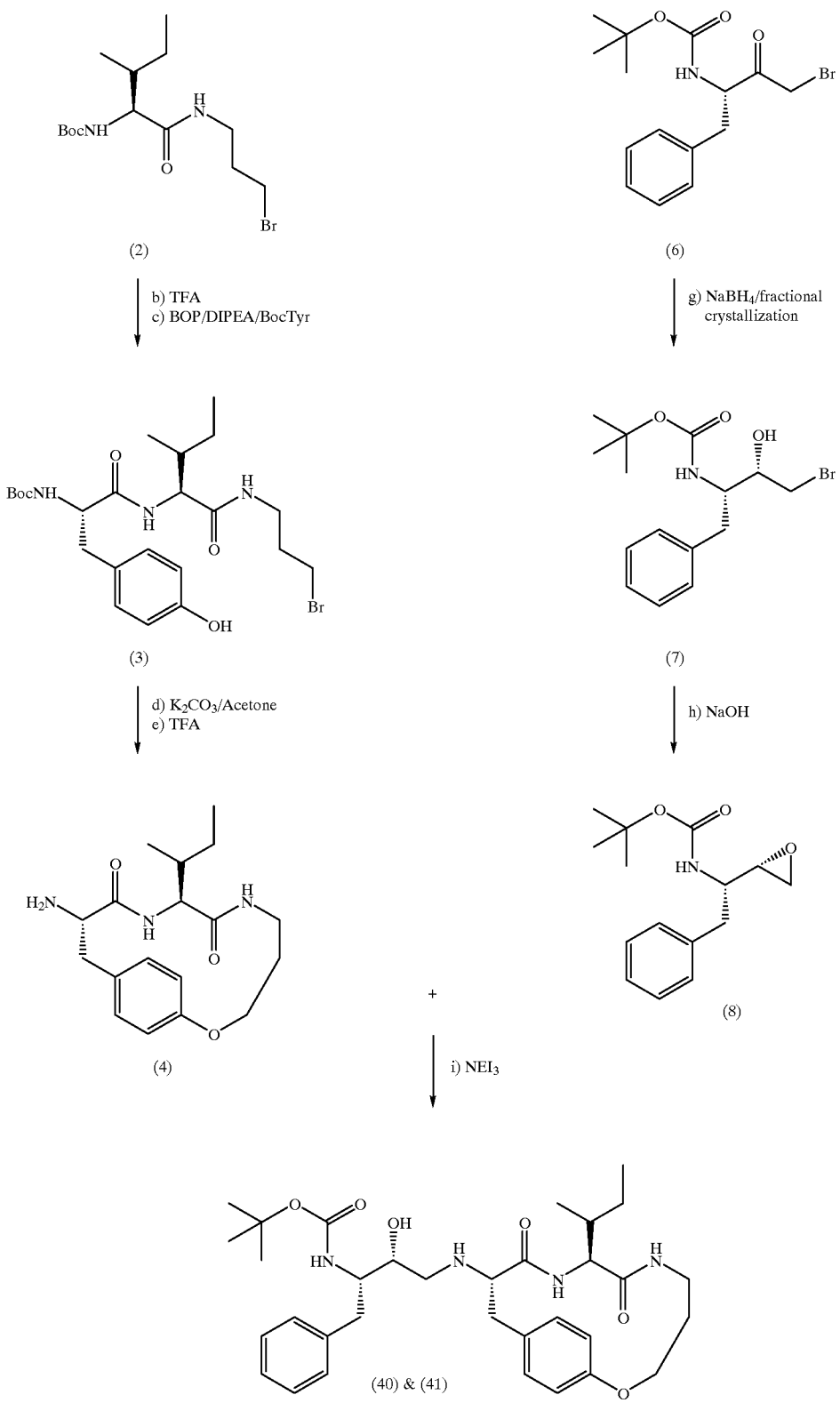

Scheme 4
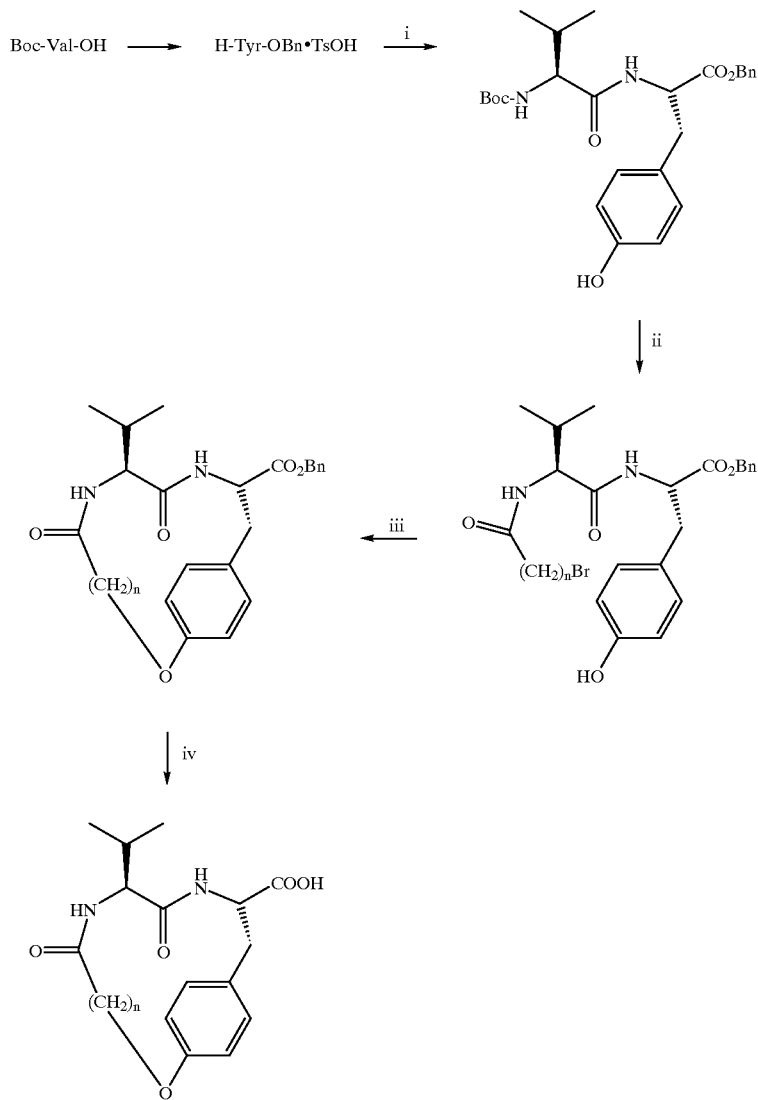
*n = 4, 5
REAGENTS: i; DCC, HOBT, Et₃N, DCM. iia; TFA, iib; Br(CH₂)ₙCOCl, KHCO₃, THF/H₂O. iii; KOtBu/DMF. iv;H₂/Pd, MeOH.
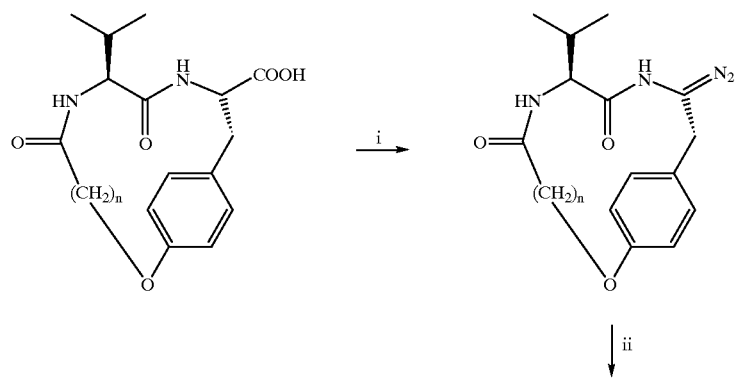

-continued
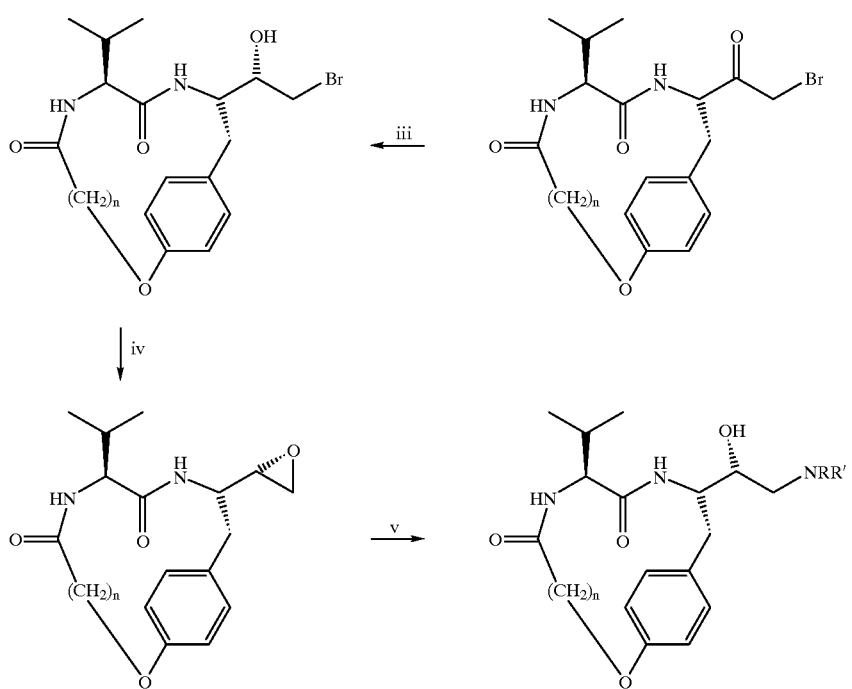
REAGENTS: ia; i-BuOCOCl, NMP, -15° C. ib; $CH_2N_2$. ii; HBr. iii; $NaBH_4$, EtOH, -10° C. iv; NaOMe/MeOH. v; RR'NH, DMF, 80° C.
TABLE 1
| Compound | $IC_{50}$, nM |
|---|---|
| 2. R Isomer | 1580 |
| 3. S Isomer | 39 |
| 4. R Isomer | 9500 |
| 5. S Isomer | 850 |

TABLE 1-continued
| Compound | IC$_{50}$, nM |
|---|---|
| 6. R Isomer | 55000 |
| 7. S Isomer | 120000 |
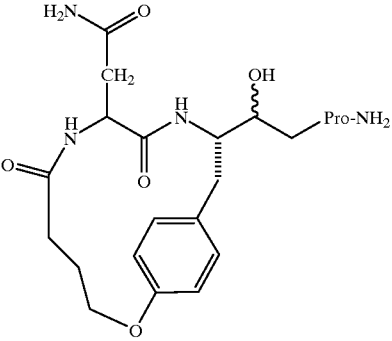
| | |
|---|---|
| 8. R Isomer | 700 |
| 9. S Isomer | 37 |
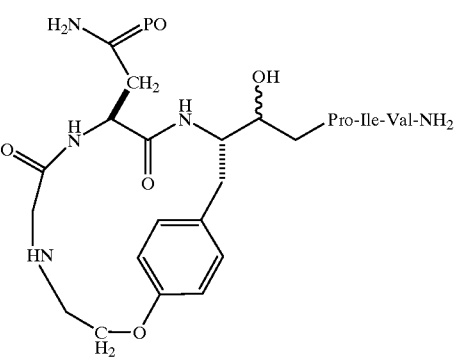
| | |
|---|---|
| 10. R Isomer | 600 |
| 11. S Isomer | 49 |
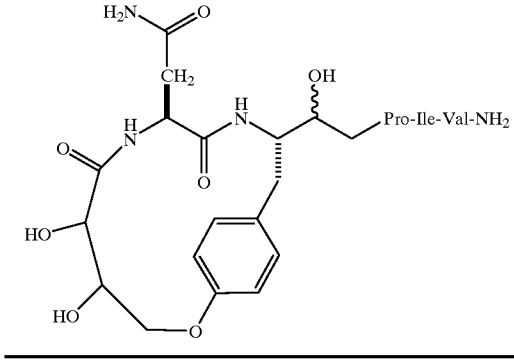

TABLE 2

| | Compound | IC$_{50}$, nM |
|---|---|---|
| [structure with H$_2$N-C(O)-CH$_2$-CH(NHC(O)-)-C(O)-NH-CH(CH$_2$-C$_6$H$_4$-O-(CH$_2$)$_4$-)-CH(OH)-Pro-Ile-Val-NH$_2$] | 12. R Isomer<br>13. S Isomer | 165<br>26 |
| [structure with Ac-NH-CH(CH$_2$C(O)NH$_2$)-C(O)-NH-CH(CH$_2$-C$_6$H$_4$-O-(CH$_2$)$_3$CO$_2$Et)-CH(OH)-Pro-Ile-Val-NH$_2$] | 14. R Isomer<br>15. S Isomer | 350<br>45 |
| [cyclic disulfide structure with Ac-Cys-Gly-...-Cys-S-S- containing Asn and hydroxy-Tyr-Pro-Ile-Val-NH$_2$] | 16. R Isomer<br>17. S Isomer | 122,000<br>28,000 |

TABLE 3

| | Compound | IC$_{50}$, nM |
|---|---|---|
| [macrocyclic structure with HO-C$_6$H$_4$-, Asn side chain with H$_2$N-C(O)-CH$_2$-, OH, and PIV-NH$_2$; ring closed through -O-CH$_2$-C(O)-NH-] | 18. S Isomer<br>19. R Isomer | 38<br>165 |

TABLE 3-continued
| | Compound | IC$_{50}$, nM |
|---|---|---|
| 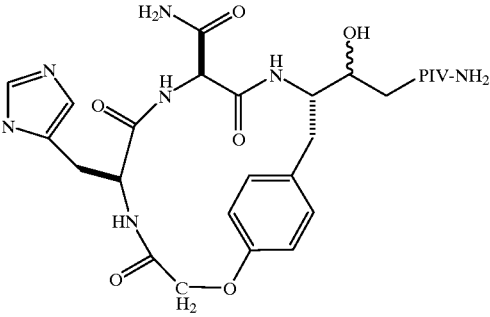 | 20. S Isomer<br>21. R Isomer | 26<br>339 |
| 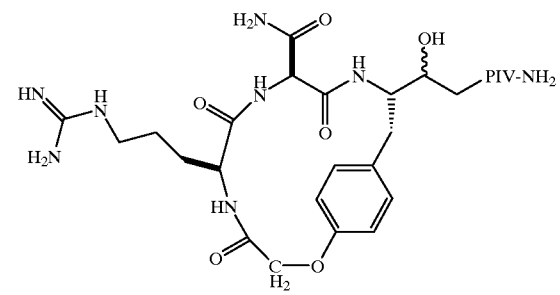 | 22. S Isomer<br>23. R Isomer | 42<br>49 |
| 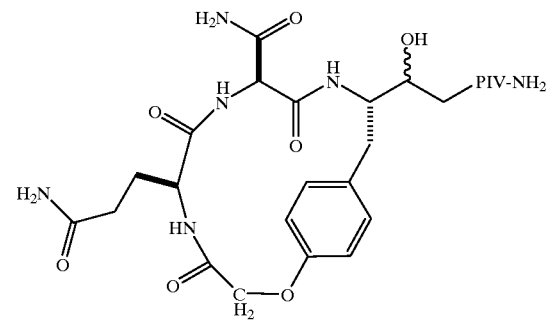 | 24. R Isomer<br>25. S Isomer | 40 rac |
TABLE 4
| | Compound | IC$_{50}$, nM |
|---|---|---|
| 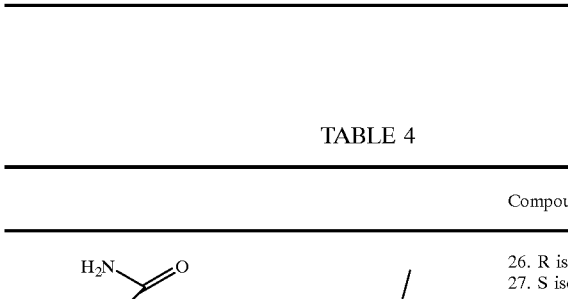 | 26. R isomer<br>27. S isomer | 1700<br>1900 |

TABLE 4-continued
| | Compound | IC$_{50}$, nM |
|---|---|---|
| 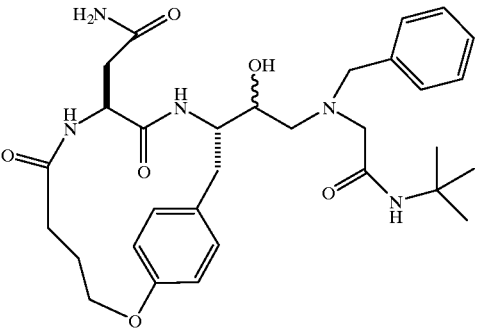 | 28. R isomer<br>29. S isomer | 1500<br>46000 |
| 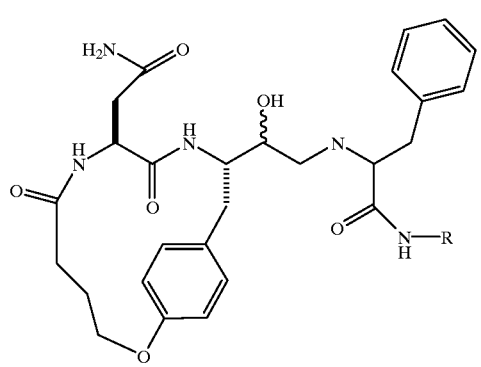 | R = tBu<br>30. R isomer<br>31. S isomer<br>R = iPr<br>32. R isomer<br>33. S isomer<br>R = iBu<br>34. R isomer<br>35. S isomer | rac 70000<br><br>rac 42000<br><br>rac 5200<br> |
TABLE 5
| | Compound | IC$_{50}$, nM |
|---|---|---|
| 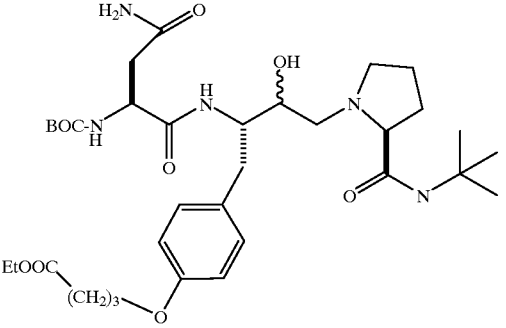 | 36. R Isomer<br>37. S Isomer | 7050<br>22000 |
| 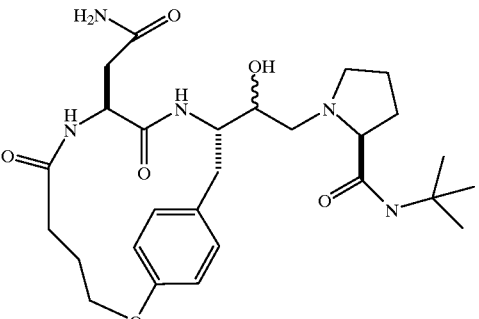 | 38. R Isomer<br>39. S Isomer | 194<br>490 |

TABLE 5-continued
| | Compound | IC$_{50}$, nM |
|---|---|---|
| 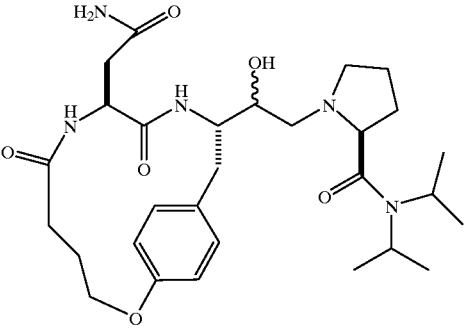 | 40. R Isomer<br>41. S Isomer | 106000<br>290000 |
| 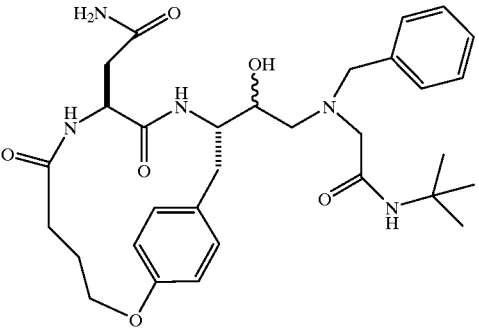 | 42. R Isomer<br>43. S Isomer | 1500<br>46000 |
| 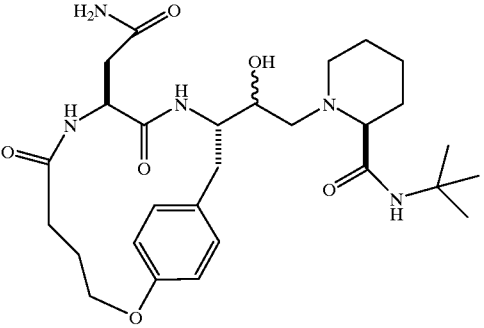 | 44. R Isomer<br>45. S Isomer | 16<br>5600 |
TABLE 6
| | Compound | IC$_{50}$, nM |
|---|---|---|
| 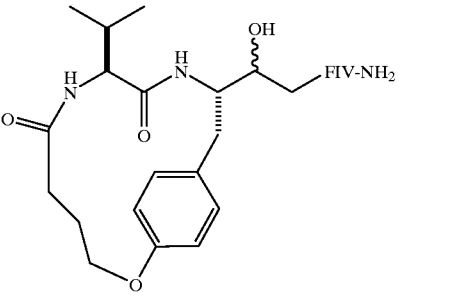 | 46. R Isomer<br>47. S Isomer | 49 |

TABLE 6-continued

| Compound | IC$_{50}$, nM |
|---|---|
| n = 3 | |
| 48. R Isomer | 40 |
| 49. S Isomer | |
| n = 4 | |
| 50. R Isomer | 30 |
| 51. S Isomer | |

| Compound | IC$_{50}$, nM |
|---|---|
| n = 5 | |
| 52. R Isomer | |
| 53. S Isomer | 85 |
| 54. R Isomer | |
| 55. S Isomer | |

| Compound | IC$_{50}$, nM |
|---|---|
| 56. R Isomer | |
| 57. S Isomer | |

TABLE 7

| Compound | IC$_{50}$, nM |
|---|---|
| 58. R Isomer | 13 |
| 59. S Isomer | |

TABLE 7-continued

| | Compound | IC$_{50}$, nM |
|---|---|---|
| | n = 3 | 2 |
| | 60. R Isomer | |
| | 61. S Isomer | |
| | n = 4 | 1 |
| | 62. R Isomer | |
| | 63. S Isomer | |
| | n = 5 | |
| | 64. R Isomer | |
| | 65. S Isomer | 2 |
| | n = 3, R 32 H | |
| | 66. R Isomer | 1.5 |
| | 67. S Isomer | |
| | n = 4, R = H | |
| | 68. R Isomer | 0.5 |
| | 69. S Isomer | |
| | n = 5, R = H | |
| | 70. R Isomer | |
| | 71. S Isomer | |
| | n = 4, R = CH$_3$ | |
| | 72. R Isomer | |
| | 73. S Isomer | |

TABLE 8

| | Compound | IC$_{50}$, nM |
|---|---|---|
| | 74. R Isomer | |
| | 75. S Isomer | |

TABLE 8-continued
| | Compound | IC$_{50}$, nM |
|---|---|---|
| 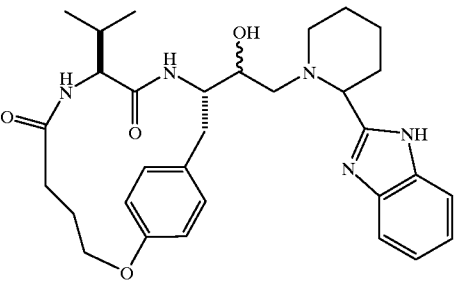 | 76. R Isomer<br>77. S Isomer | |
| 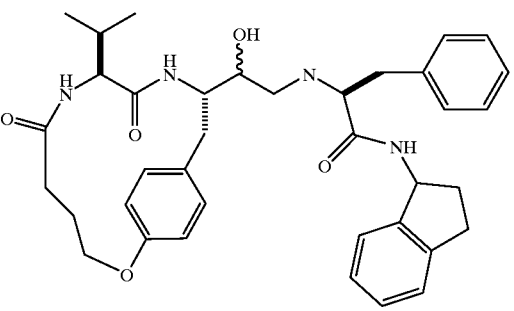 | 78. R Isomer<br>79. S Isomer | |
| 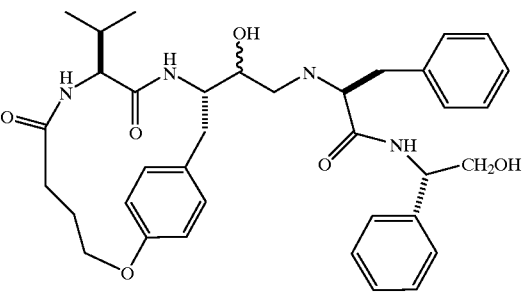 | 80. R Isomer<br>81. S Isomer | |
| 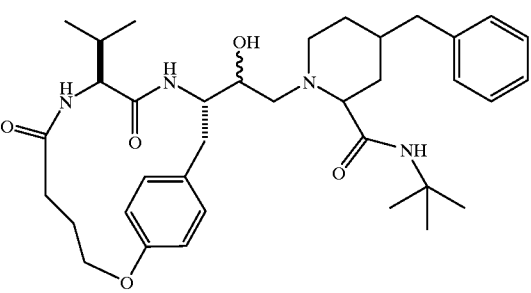 | 82. R Isomer<br>83. S Isomer | |

TABLE 9

[Structure: X—NH-CH(CH2-phenyl)-Y-C(=O)-NH-CH(-C(=O)-NH-CH(CH(CH3)CH2CH3)-C(=O)-NH-(CH2)n-O-phenyl-CH2-) macrocycle]

| Compound | X | Y | n | | IC$_{50}$, nM |
|---|---|---|---|---|---|
| 84 Ac-SLNFPIV-NH$_2$ | — | — | — | R | 22 |
|  |  |  |  | S | 1 |
| 85 Ac-LNFPIV-NH$_2$ | — | — | — | R | 60 |
|  |  |  |  | S | 9 |
| 86 Ac-LVFFIV-NH$_2$ | — | — | — | R | 5 |
| 87 | Ac-Leu-Val- | —CH(OH)CH$_2$NH | 3 | R | 2 |
| 88 | Ac-Leu-Val- | —CH(OH)CH$_2$NH | 4 | R | 5 |
| 89 | tBu-O-C(=O)-CH$_2$-C(=O)- | —CH(OH)CH$_2$NH | 3 | R | 15 |
| 90 | tBu-O-C(=O)-CH$_2$-C(=O)- | —CH$_2$NH | 3 | R | 150 |
| 91 | (3-tetrahydrofuranyl)-O-C(=O)- | —CH(OH)CH$_2$NH | 3 | R | 15 |
| 92 | 3-methylbenzoyl | —CH(OH)CH$_2$NH | 3 | R + S | 50 |
| 93 | quinoline-2-carbonyl-NH-CH(iPr)-C(=O)- | —CH(OH)CH$_2$NH | 3 | R | 1 |
| 94 | DM323 | — | — | — | 1 |

TABLE 10

| | Compound | IC$_{50}$, nM |
|---|---|---|
| | R = OH | |
| | 95. R isomer | |
| | 96. S isomer | |
| | R = CH$_2$CO$_2$H | |
| | 97. R isomer | |
| | 98. S isomer | |
| | R = CH$_2$CO$_2$H | |
| | 99. R isomer | 25 |
| | 100. S isomer | |
| | R = CH$_2$CO$_2$Me | 15 |
| | 101. R isomer | |
| | 102. S isomer | 5 |
| | R = CH$_2$CO$_2$Bu | |
| | 103. R isomer | |
| | 104. S isomer | 2 |
| | R = CH$_2$CO$_2$Hex | |
| | 105. R isomer | 2 |
| | 106. S isomer | |
| | 107. R isomer | 250 |
| | 108. S isomer | |

TABLE 11

| | Compound | IC$_{50}$, nM |
|---|---|---|
| | 109. R isomer | |
| | 110. S isomer | |

TABLE 11-continued
| Compound | IC$_{50}$, nM |
|---|---|
| 111. R isomer | 8 |
| 112. S isomer | |
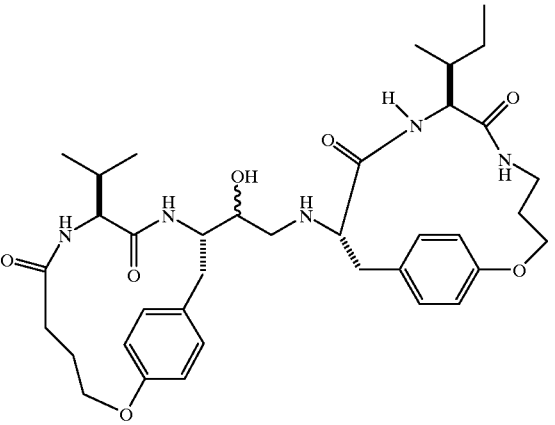
| | |
|---|---|
| 113. R isomer | |
| 114. S isomer | |
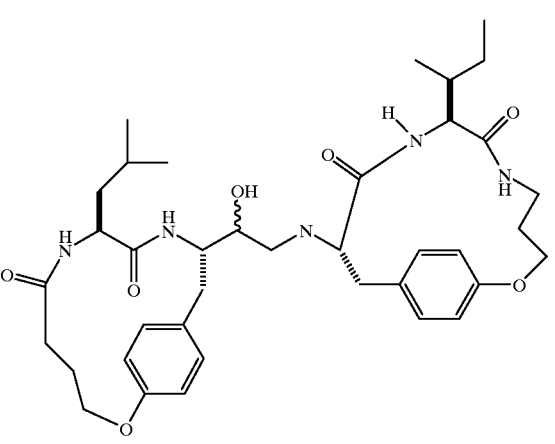
| | |
|---|---|
| 115. R isomer | |
| 116. S isomer | |
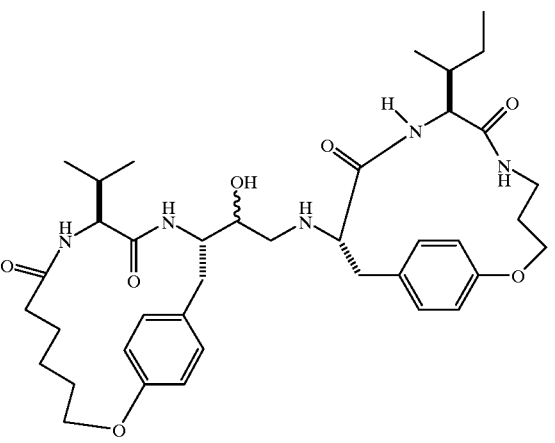

TABLE 12
| | Compound | IC$_{50}$, nM |
|---|---|---|
| 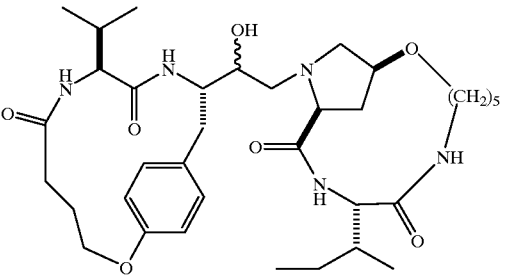 | 117. R isomer<br>118. S isomer | |
| 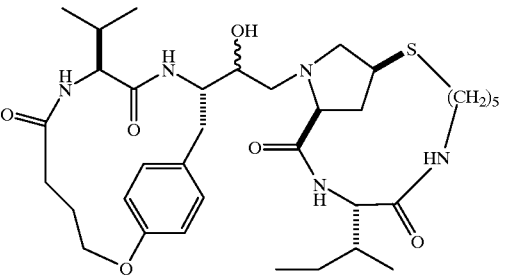 | 119. R isomer<br>120. S isomer | |
| 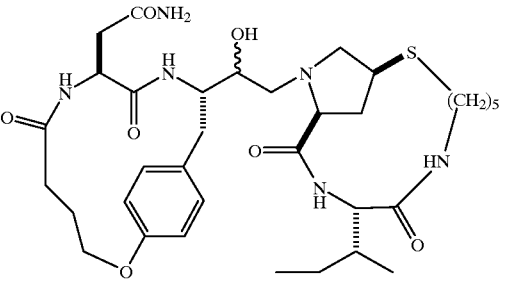 | 121. R isomer<br>122. S isomer | |
| 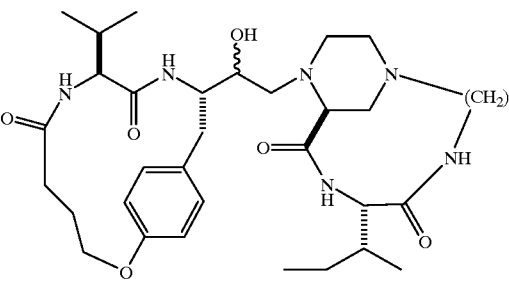 | 123. R isomer<br>124. S isomer | |
| 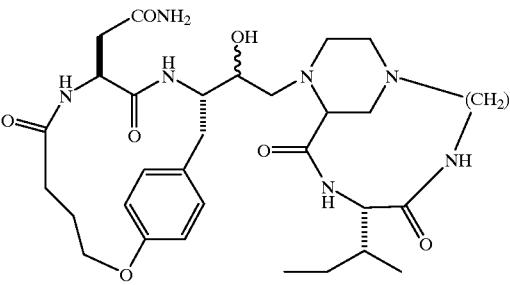 | 125. R isomer<br>126. S isomer | |

TABLE 13
| | Compound | IC$_{50}$, nM |
|---|---|---|
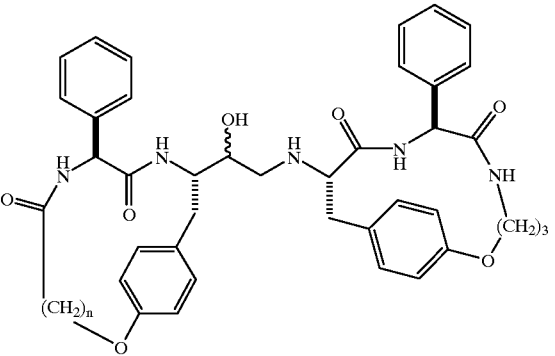
127. R isomer
128. S isomer
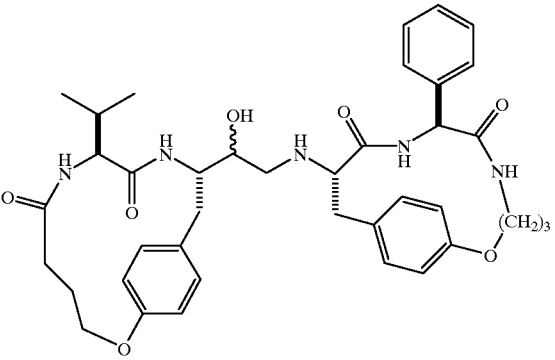
129. R isomer
130. S isomer
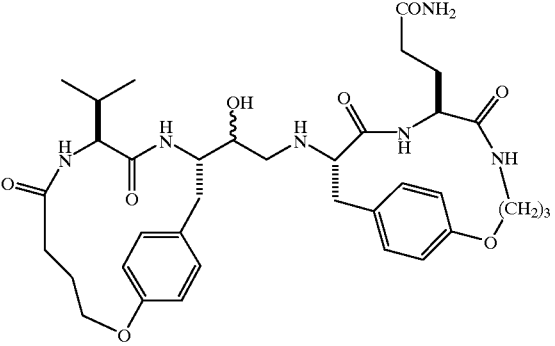
131. R isomer
132. S isomer
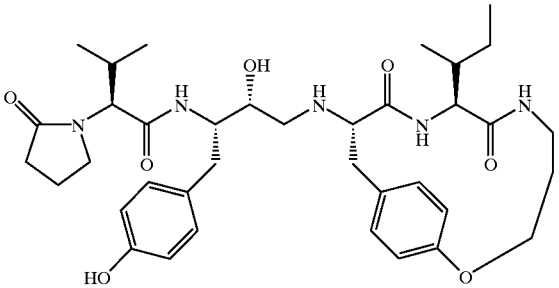
133.

TABLE 13-continued

| | Compound | IC$_{50}$, nM |
|---|---|---|

134.

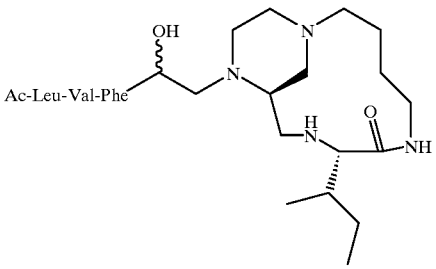

TABLE 14

Data collection and refinement statistics for HIVPR and HIVKI inhibitor complexes

| Inhibitor | 3<br>l.h.s.-PIV | 44<br>l.h.s.-tBu | 89<br>r.h.s.-tBu | 133<br>r.h.s.-5c-Tyr |
|---|---|---|---|---|
| Protease | HIVPR<br>Aba 67/95 | HIVKI<br>Aba 67/95 | HIVKI<br>Aba 67/95 | HIVKI<br>Aba 67/95 |
| Resolution limit | 2.0 Å | 1.75 Å | 1.75 Å | 1.85 Å |
| R$_{sym}$ | 0.080 | 0.067 | 0.068 | 0.063 |
| % completeness of data | 97.1% | 82.5% | 85.9% | 80.5% |
| Unit cell parameters (a, b, c) | 51.3 Å<br>58.8 Å<br>62.3 Å | 51.4 Å<br>59.3 Å<br>61.9 Å | 51.4 Å<br>58.7 Å<br>62.0 Å | 61.6 Å<br>59.1 Å<br>62.4 Å |
| Number of observations (I/sigI > 1.0) | 59.803 | 52.113 | 88.133 | 39,617 |
| Number of unique reflections | 11,924 | 16,268 | 16,528 | 13,620 |
| | 8-2.0 Å | 8-1.75 Å | 8-1.75 Å | 8-1.85 Å |
| Refinement Statistics | | | | |
| Final R-factor (R-free) | 0.163<br>(0.237) | 0.177<br>(0.239) | 0.179<br>(0.244) | 0.172<br>(0.239) |
| RMS bl | 0.009 Å | 0.010 Å | 0.010 Å | 0.009 Å |
| RMS ba | 1.59° | 1.55° | 1.66° | 1.65° |
| RMS dihe | 26.9° | 26.1° | 26.1° | 26.4° |
| RMS impr | 1.42° | 1.29° | 1.40° | 1.40° |
| Number of waters | 95 | 107 | 115 | 114 |
| Number of sulphates | 3 | 3 | 3 | 3 |
| Sidechains modelled as Ala | Lys 41, 43, 45, 70, 141, 143 | Lys 41, 43, 143 | Lys 41, 43, 141, 143 | Asn37, Lys 41, 43, 45, 55, 70, 141 |
| Residues for which two sidechain conformations were modelled | — | Arg8, Glu34, Arg57, Gln61, Glu65, Gln118, Glu135, Met148, Lys155 | Glu34, Glu35, Ile50, Gly51, Arg57, Met146, Ile150, Gly151 | Glu35, Ile50, Gly51, Gln61, Val82, Ile150, Gly151, Val182 |

LEGENDS

FIG. 1

Molecular model of cyclic inhibitor 3 (dark outline) superimposed on the protease bound conformation of JG-365 (light outline)

FIG. 2

Overlay of the crystal structure of cyclic inhibitor 3 (bound to HIVPR) superimposed on the crystal structure of JG-365 (bound to HIVPR)

FIG. 3

Mass spectral analysis of cyclic inhibitor (12) after incubation (37° C., 1h, 5 units each enzyme) with human cathespin D, pepsin 3a or gastrixin

FIG. 4

Mass spectral analysis of cyclic inhibitor (10) after incubation (37° C., 1h, 5 units each enzyme) with human cathespin D, pepsin 3a or gastrixin

FIG. 5

Mass spectral analysis of cyclic inhibitor (11) after incubation (37° C., 1h, 5 units each enzyme) with human cathespin D, pepsin 3a or gastrixin

FIG. 6

Mass spectral analysis of cyclic inhibitor (8) after incubation (37° C., 1h, 5 units each enzyme) with human cathespin D, pepsin 3a or gastrixin

FIG. 7

Mass spectral analysis of cyclic inhibitor (9) after incubation (37° C., 1h, 5 units each enzyme) with human cathespin D, pepsin 3a or gastrixin

FIG. 8

Mass spectral analysis of cyclic inhibitor (3) after incubation (37° C., 1h, 5 units each enzyme) with human cathespin D, pepsin 3a or gastrixin

FIG. 9

Mass spectral analysis of cyclic inhibitor (2) after incubation (37° C., 1h, 5 units each enzyme) with human cathespin D, pepsin 3a or gastrixin

FIG. 11

Overlay of receptor bound conformations of 3 (modelled structure) [199] on JG-365 (x-ray structure) [197]

FIG. 12

Overlay of receptor bound conformations of 87 (modelled structure) [203] on JG-365 (x-ray structure) [197]

FIG. 13

Overlay of receptor bound conformations of 134 (modelled structure) [203] on JG-365 (x-ray structure) [197]

FIG. 14

Overlay of receptor bound conformations of 111 (modelled structure) [203] on JG-365 (x-ray structure) [197]

We claim:

1. A HIV-1 protease inhibitor selected from compounds of structure

N-Terminus Cyclic Inhibitors (i)

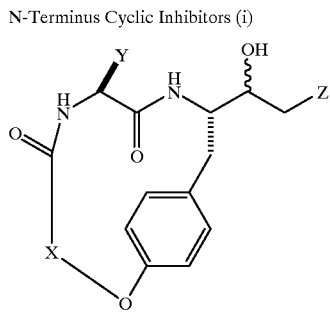

wherein Z is selected from

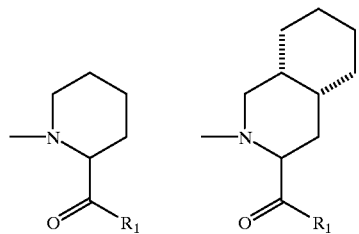

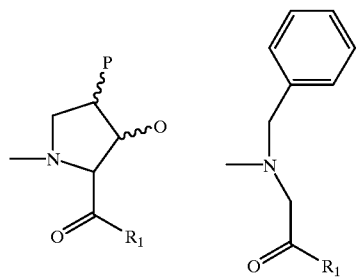

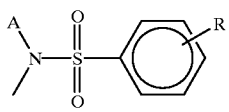

wherein X is selected from $(CH_2)_n$ where n=3–6, —CH(OH)—CH(OH)—CH$_2$—, CH(CO$_2$H)—CH$_2$—CH$_2$, CH$_2$CONHCHR where R=D or L amino acids and alkyl of 1–6 carbon atoms inclusive of linear or branched chains;

wherein Y is selected from side chains of Asn or Ile or Val or Glu and alkyl of 1–6 carbon atoms inclusive of linear or branched chains as well as cycloalkyl; and wherein Z is selected from

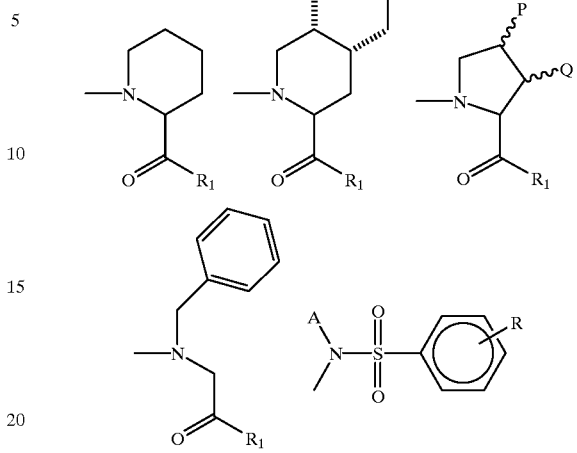

wherein P=H, alkyl, aryl, Oalkyl, Nalkyl

Q=H, alkyl, aryl, Oalkyl, Nalkyl

R$_1$=NHtBu, OtBu, NHiBu, NHiPr, NHnBu, NHnPr, NHalkyl, Oalkyl; or

A=alkyl of 1–6 carbon atoms inclusive of linear or branched structures as well as cycloalkyl; and R=is selected from amino, O-alkyl or N-alkyl.

2. A HIV-1 protease inhibitor selected from compound of the structure

C-Terminus Cyclic Inhibitors (ii)

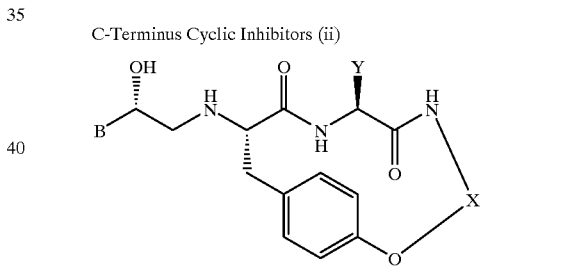

wherein B is selected from

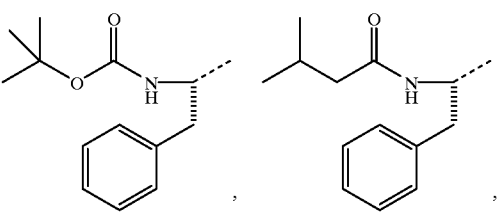

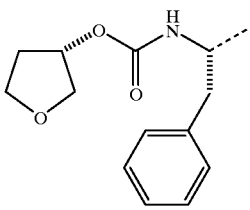

wherein X is selected from $(CH_2)_n$ where n=3–6, —CH(OH)—CH(OH)—CH$_2$—, CH(CO$_2$H)—CH$_2$—CH$_2$, CH$_2$CONHCHR where R=D or L amino acids and alkyl of 1–6 carbon atoms inclusive of linear or branched chains;

wherein Y is selected from side chains of Asn or Ile or Val or Glu and alkyl of 1–6 carbon atoms inclusive of linear or branched chains as well as cycloalkyl; and wherein B is selected from

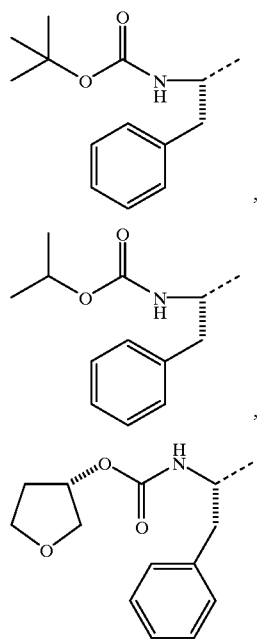

or quinoline—Val-Phe-.

3. A HIV-1 protease inhibitor having the structure

Bicyclic Inhibitors (iii)

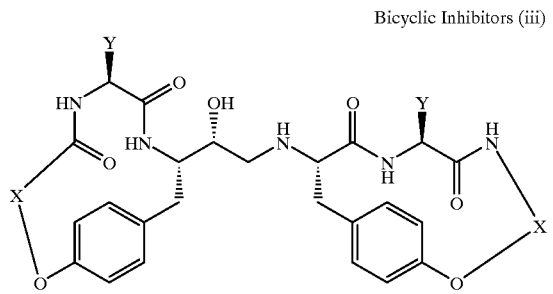

wherein X is selected from $(CH_2)_n$ where n=3–6, —CH(OH)—CH(OH)—CH$_2$—, CH(CO$_2$H)—CH$_2$—CH$_2$, CH$_2$CONHCHR where R=D or L amino acids and alkyl of 1–6 carbon atoms inclusive of linear or branched chains; and wherein Y is selected from side chains of Asn or Ile or Val or Glu and alkyl of 1–6 carbon atoms inclusive of linear or branched chains as well as cycloalkyl.

4. A HIV protease inhibitor as claimed in claim 2 wherein Y is a side chain of Ile and X is $(CH_2)_n$ wherein n is 5.

5. A HIV protease inhibitor selected from the group of compounds of the formula:

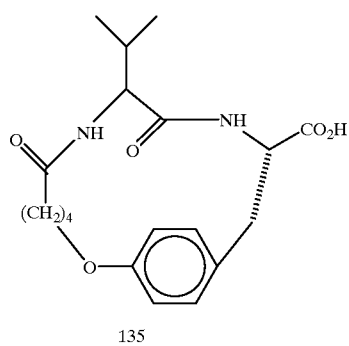

135 and

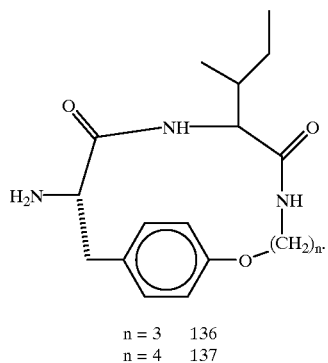

n = 3  136
n = 4  137

6. A HIV protease inhibitor selected from the group consisting of compounds 2–13, 16–35, 38–83, 87–93 and 95–134 as follows:

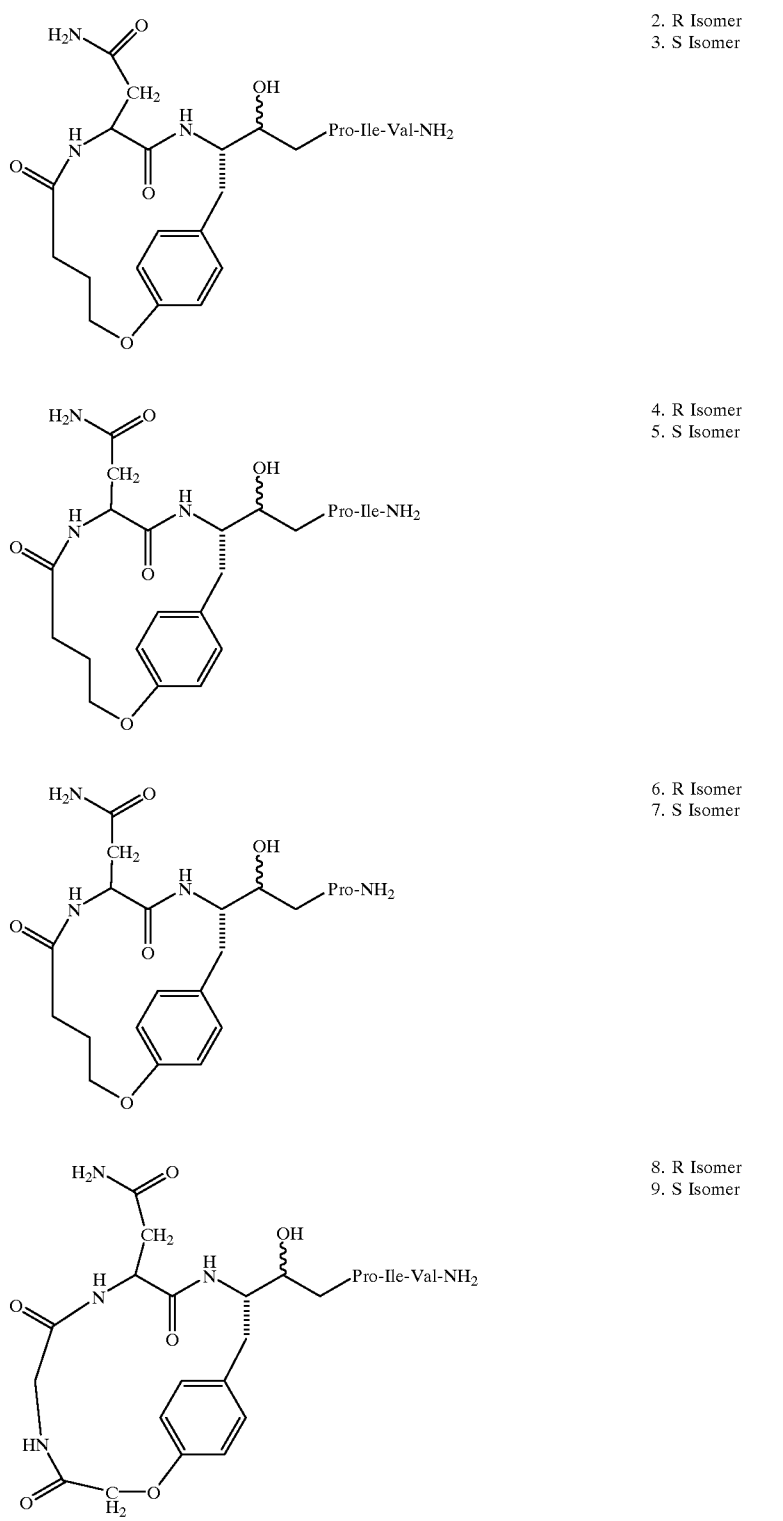

-continued
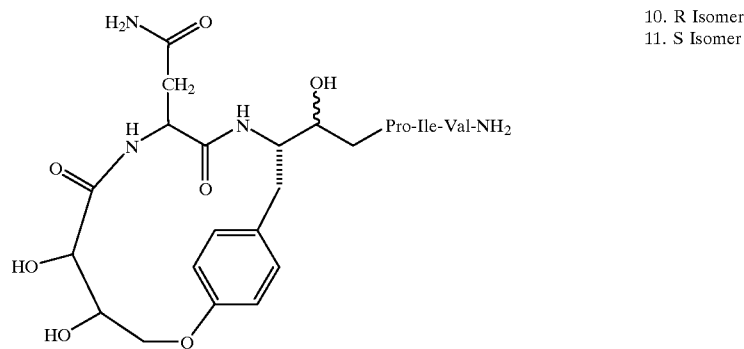
10. R Isomer
11. S Isomer
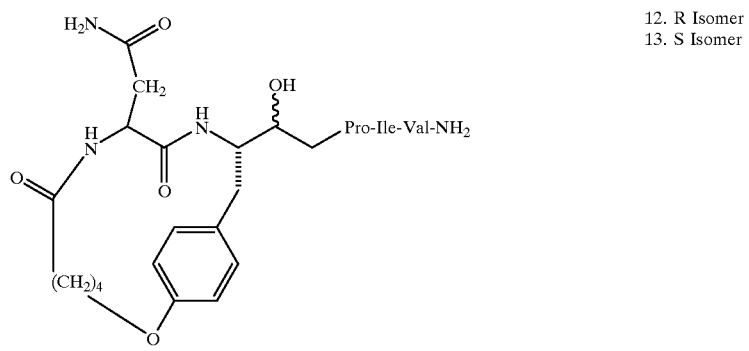
12. R Isomer
13. S Isomer
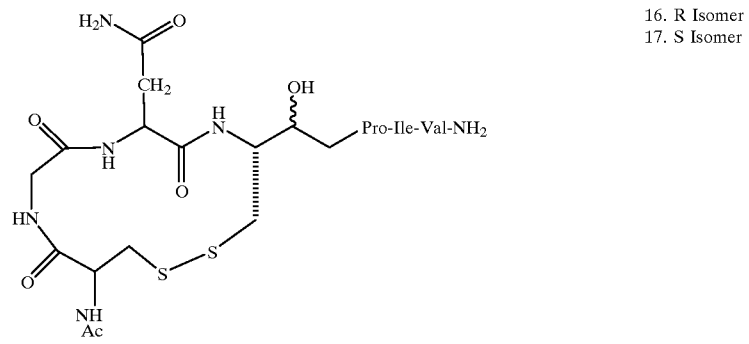
16. R Isomer
17. S Isomer
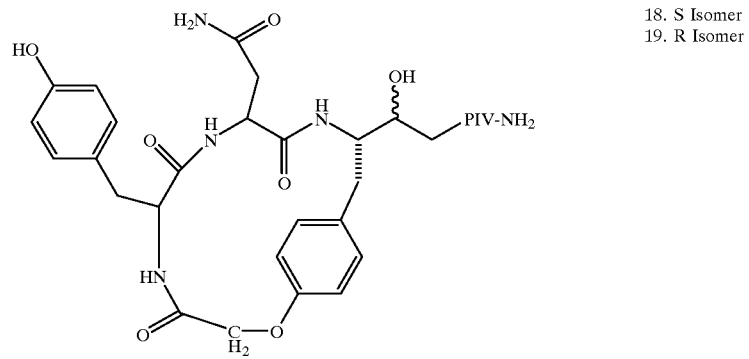
18. S Isomer
19. R Isomer -continued
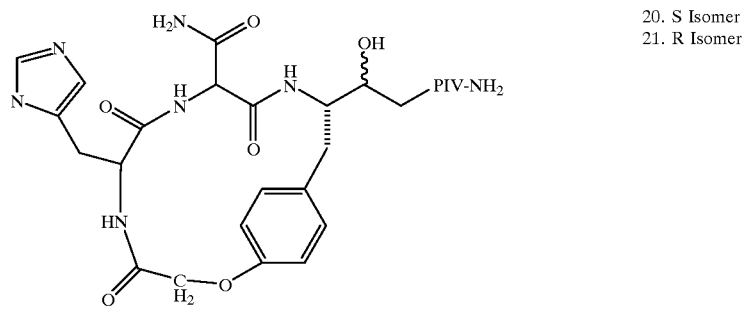 20. S Isomer
21. R Isomer
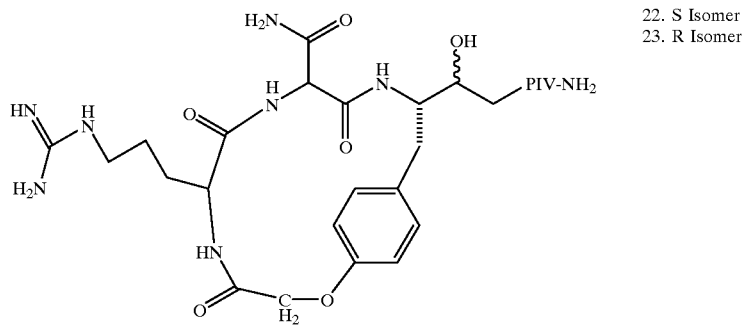 22. S Isomer
23. R Isomer
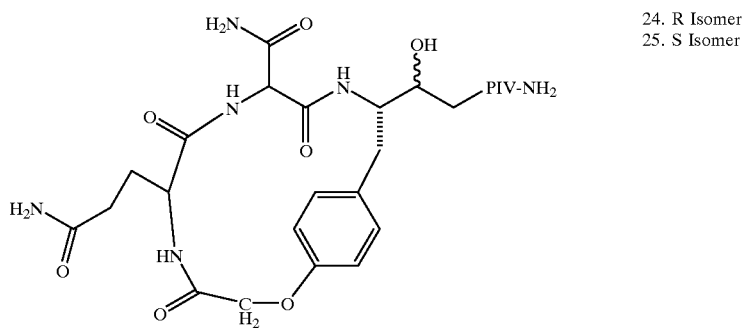 24. R Isomer
25. S Isomer
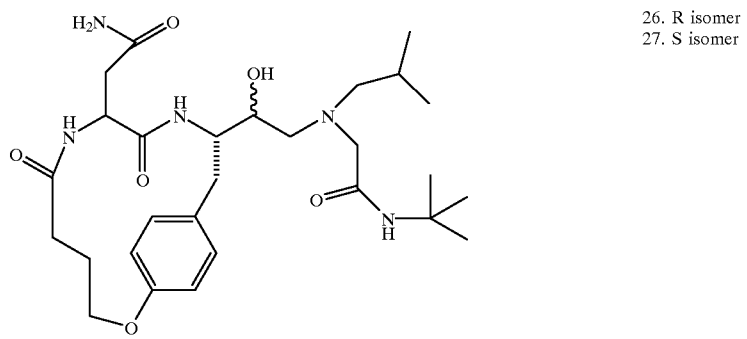 26. R isomer
27. S isomer -continued
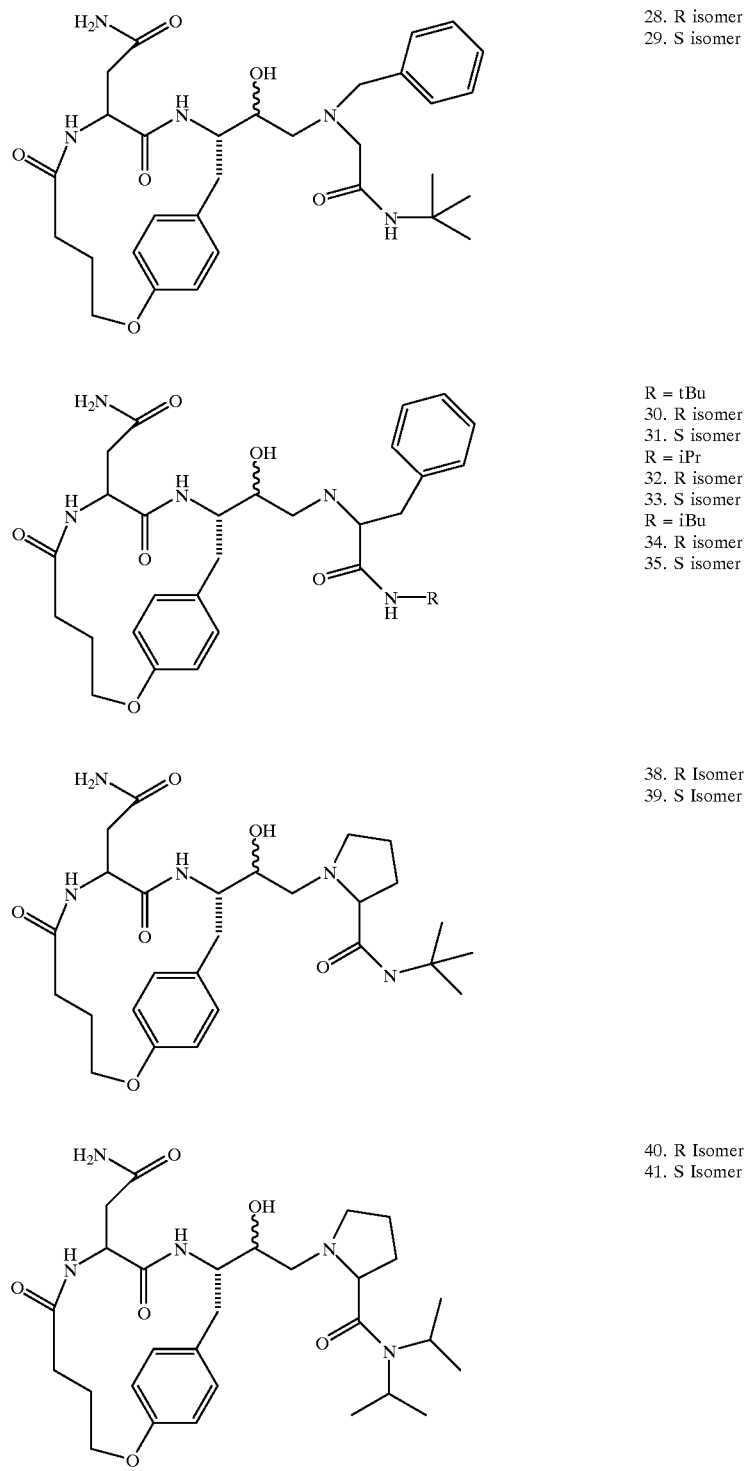
28. R isomer
29. S isomer
R = tBu
30. R isomer
31. S isomer
R = iPr
32. R isomer
33. S isomer
R = iBu
34. R isomer
35. S isomer
38. R Isomer
39. S Isomer
40. R Isomer
41. S Isomer -continued
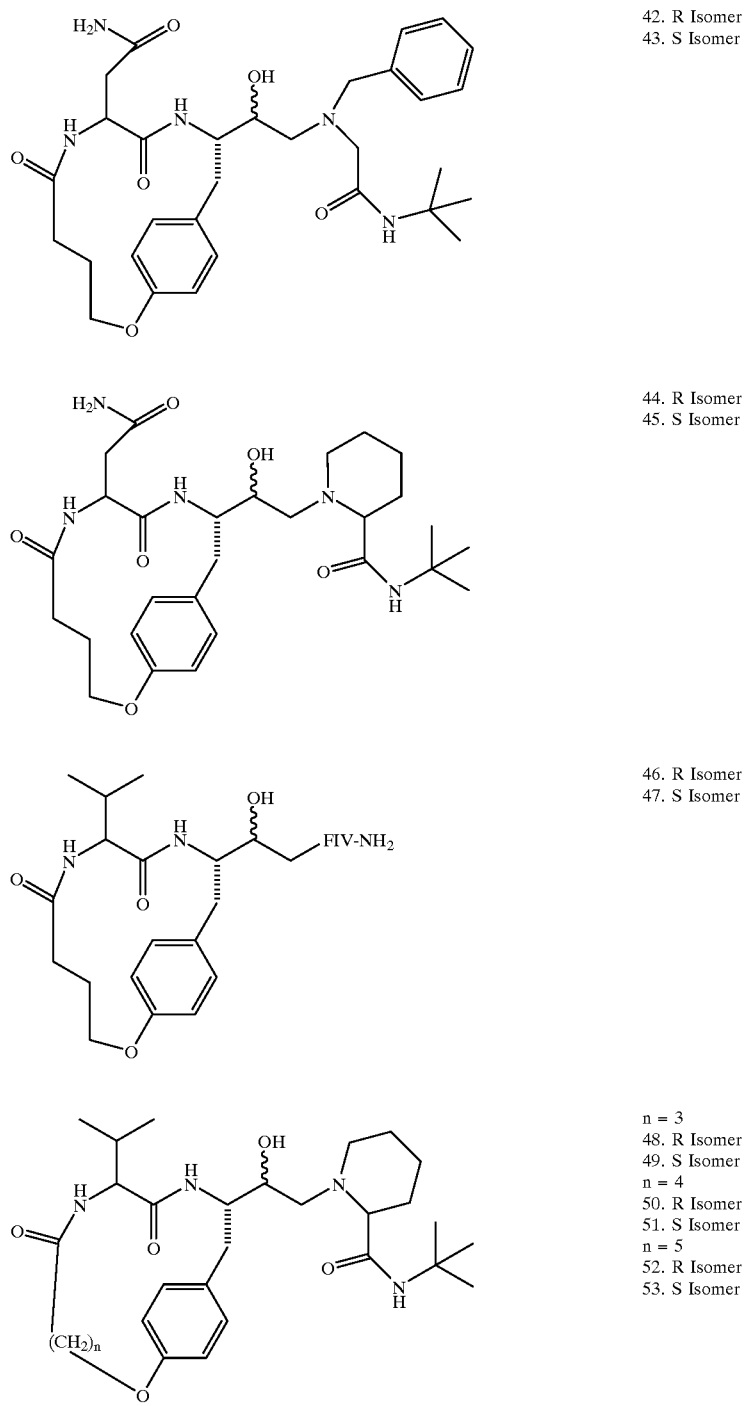
42. R Isomer
43. S Isomer
44. R Isomer
45. S Isomer
46. R Isomer
47. S Isomer
n = 3
48. R Isomer
49. S Isomer
n = 4
50. R Isomer
51. S Isomer
n = 5
52. R Isomer
53. S Isomer -continued
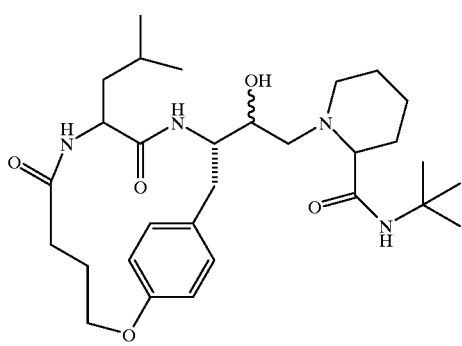
54. R Isomer
55. S Isomer
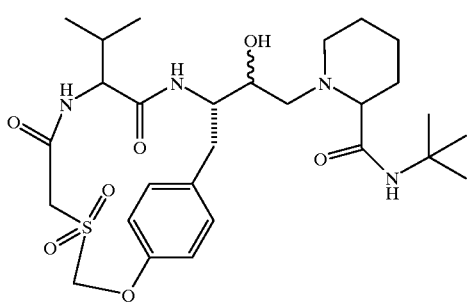
56. R Isomer
57. S Isomer
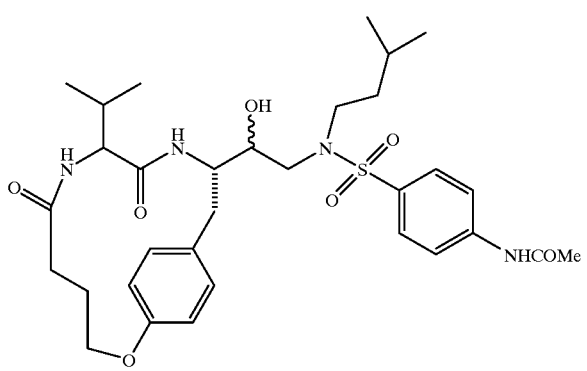
58. R Isomer
59. S Isomer
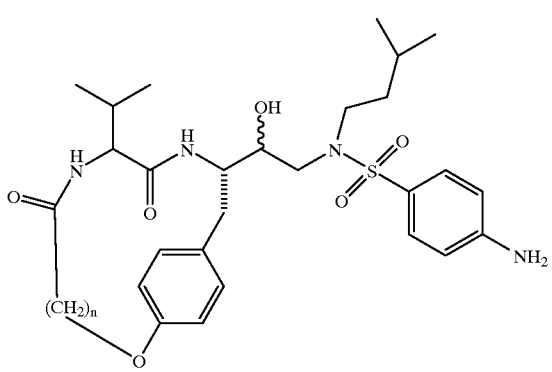
n = 3
60. R Isomer
61. S Isomer
n = 4
62. R Isomer
63. S Isomer
n = 5
64. R Isomer
S Isomer -continued
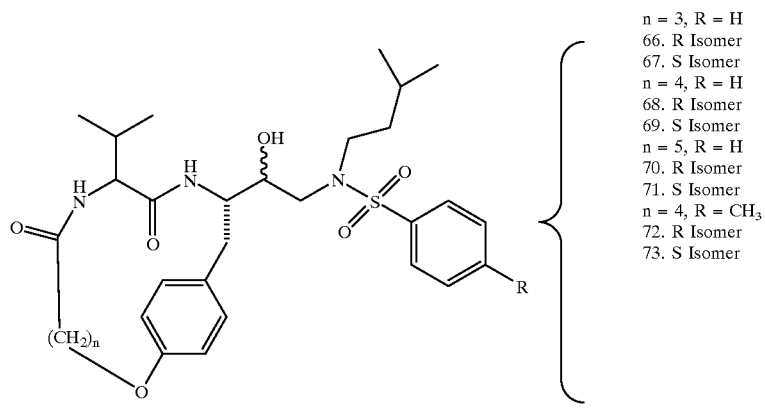
n = 3, R = H
66. R Isomer
67. S Isomer
n = 4, R = H
68. R Isomer
69. S Isomer
n = 5, R = H
70. R Isomer
71. S Isomer
n = 4, R = CH₃
72. R Isomer
73. S Isomer
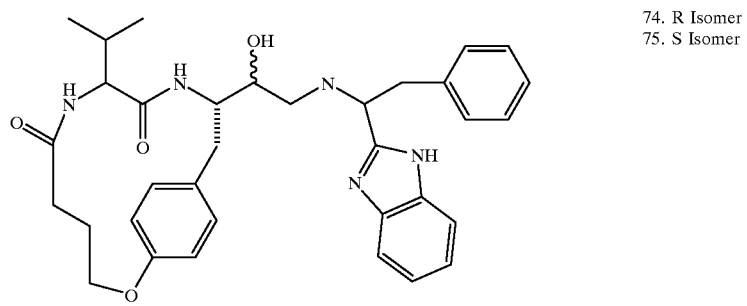
74. R Isomer
75. S Isomer
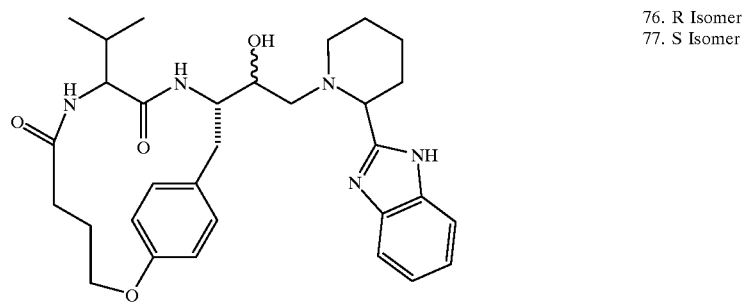
76. R Isomer
77. S Isomer
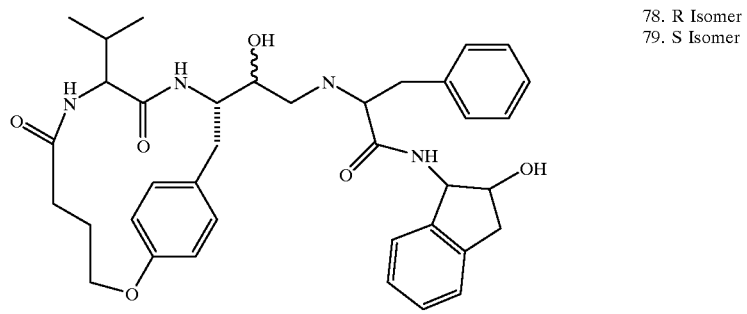
78. R Isomer
79. S Isomer -continued
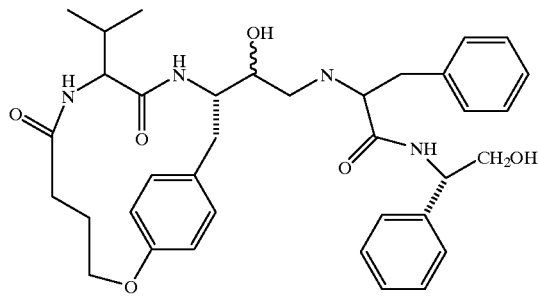
80. R Isomer
81. S Isomer
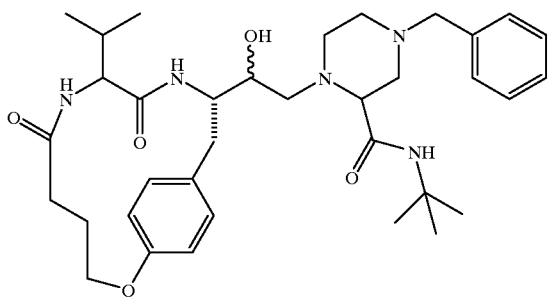
82. R Isomer
83. S Isomer
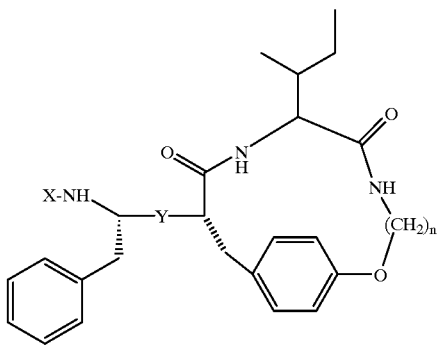
| 87–93 | X | Y | n |
|---|---|---|---|
| 87 | Ac-Leu-Val- | —CH(OH)CH$_2$NH | 3 |
| 88 | Ac-Leu-Val- | —CH(OH)CH$_2$NH | 4 |
| 89 | 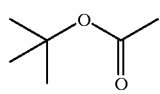 | —CH(OH)CH$_2$NH | 3 |
| 90 | 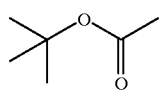 | —CH$_2$NH | 3 |

-continued
| | | | |
|---|---|---|---|
| 91 | 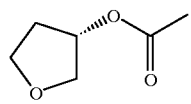 | —CH(OH)CH₂NH | 3 |
| 92 | 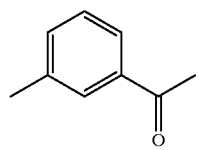 | —CH(OH)CH₂NH | 3 |
| 93 |  | —CH(OH)CH₂NH | 3 |
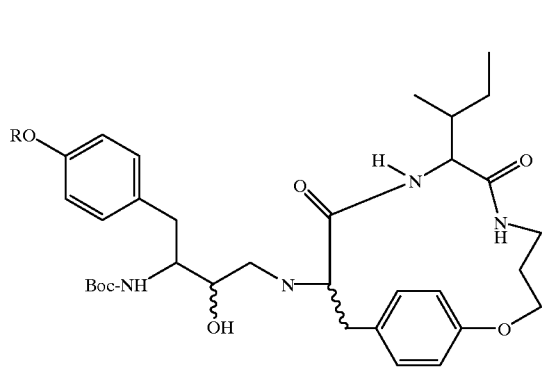
R = OH
95. R isomer
96. S isomer
R = CH₂CO₂H
97. R isomer
98. S isomer
R = CH₂CO₂H
99. R isomer
100. S isomer
R = CH₂CO₂Me
101. R isomer
102. S isomer
R = CH₂CO₂Bu
103. R isomer
104. S isomer
R = CH₂CO₂Hex
105. R isomer
106. S isomer
107. R isomer
108. S isomer
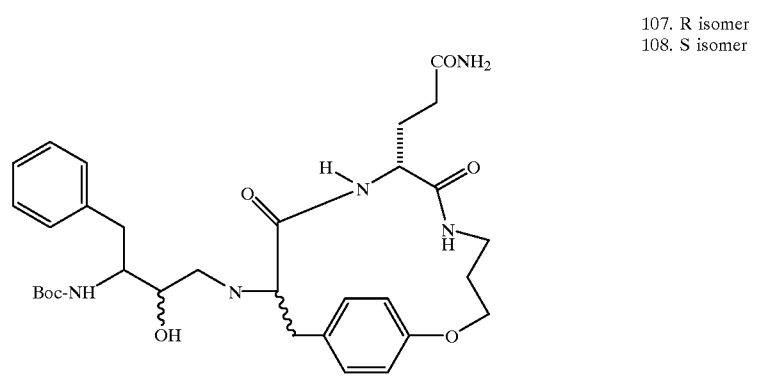

-continued
109. R isomer
110. S isomer
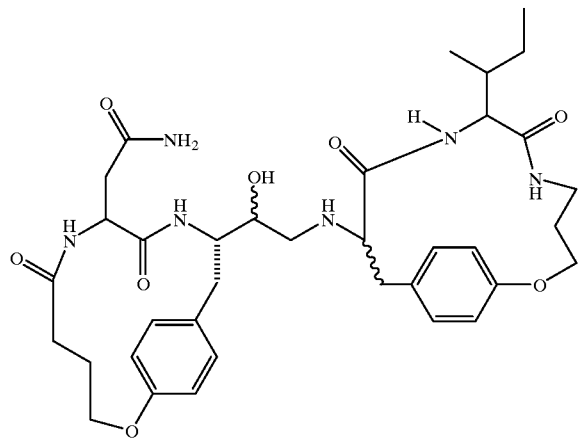
111. R isomer
112. S isomer
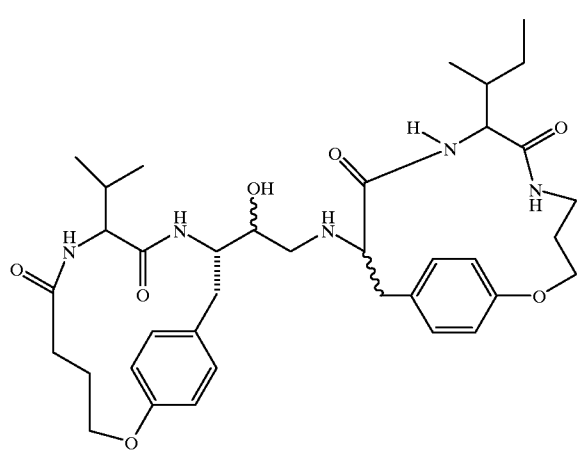
113. R isomer
114. S isomer
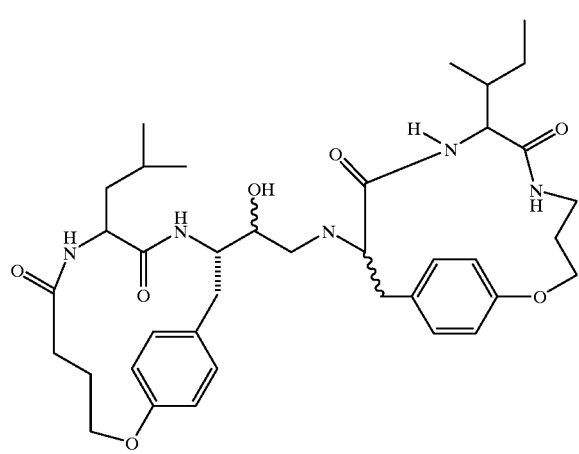

-continued
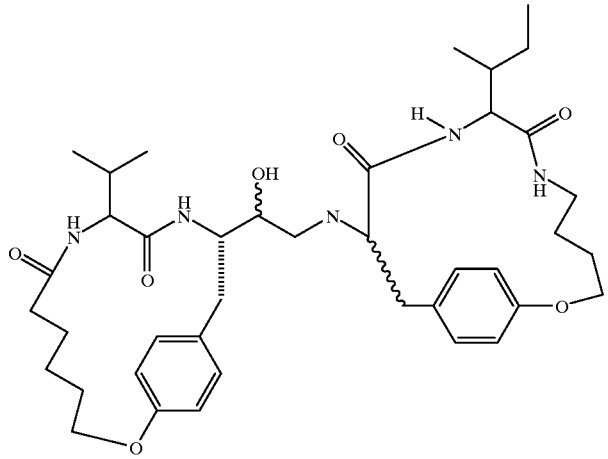
115. R isomer
116. S isomer
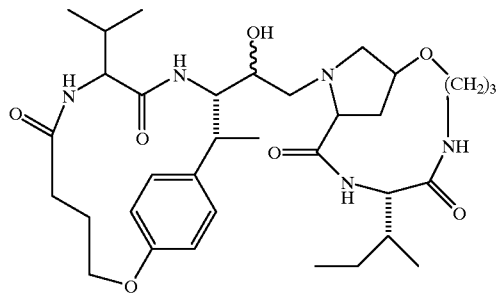
117. R isomer
118. S isomer
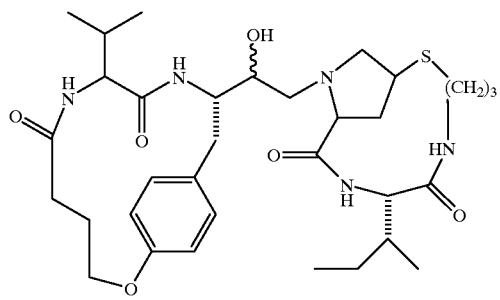
119. R isomer
120. S isomer
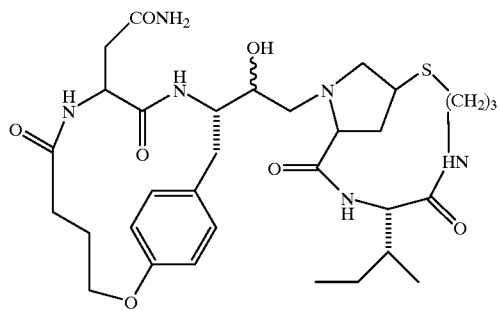
121. R isomer
122. S isomer -continued
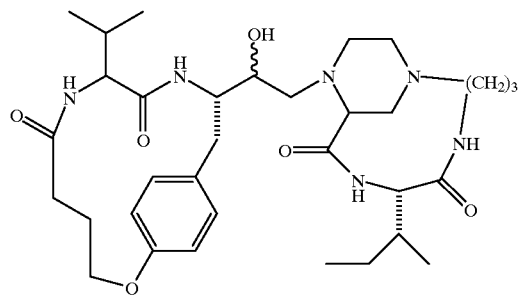
123. R isomer
124. S isomer
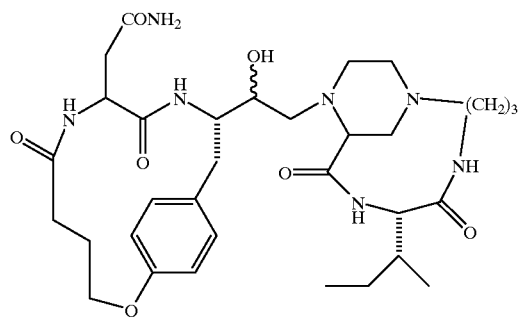
125. R isomer
126. S isomer
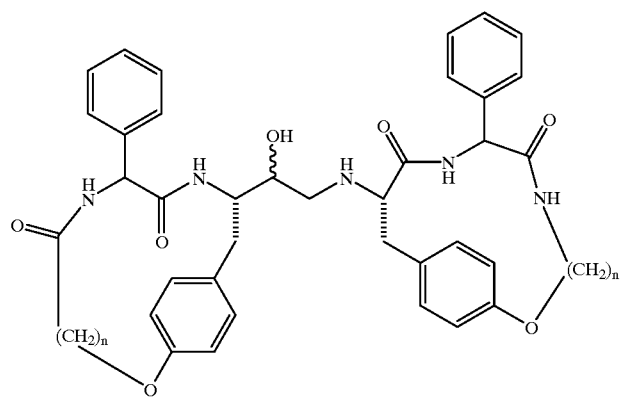
127. R isomer
128. S isomer
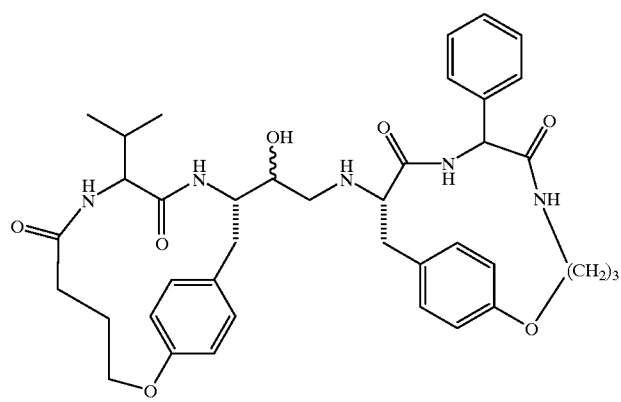
129. R isomer
130. S isomer -continued 131. R isomer
132. S isomer

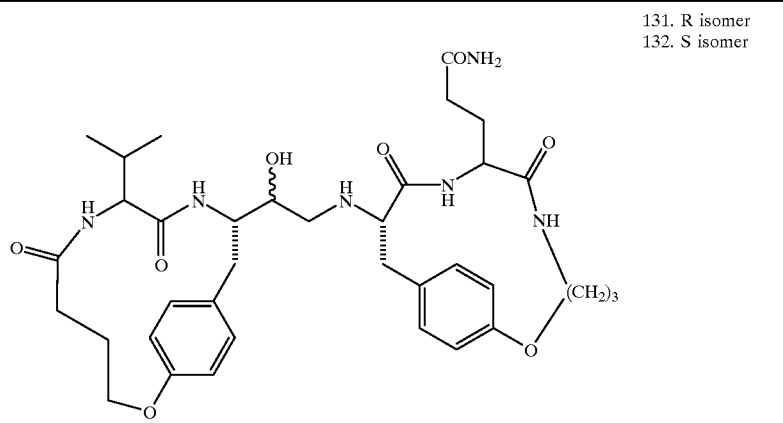

133.

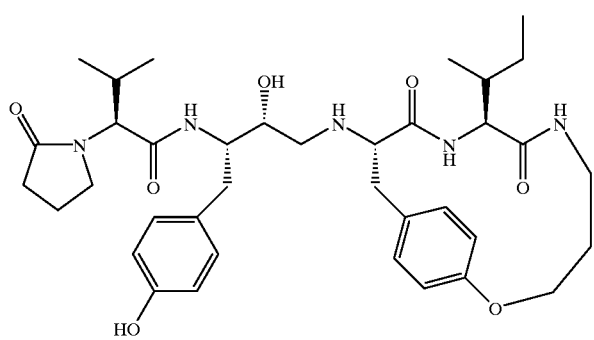

134.

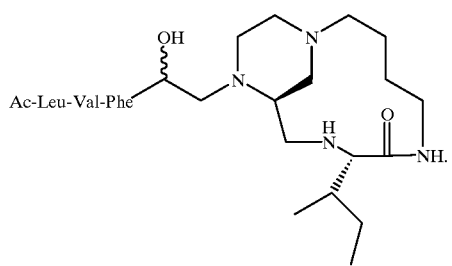

7. A HIV protease inhibitor as claimed in claim 6 which is compound 60.

8. A HIV protease inhibitor as claimed in claim 6 which is compound 61.

9. A HIV protease inhibitor as claimed in claim 6 which is compound 62.

10. A HIV protease inhibitor as claimed in claim 6 which is compound 63.

11. A HIV protease inhibitor as claimed in claim 6 which is compound 64.

12. A HIV protease inhibitor as claimed in claim 6 which is compound 65.

13. A HIV protease inhibitor as claimed in claim 6 which is compound 93.

14. A HIV protease inhibitor selected from the group consisting of compounds 14, 15, 36 and 37 as follows:

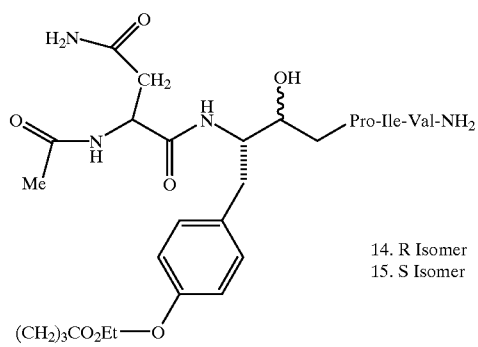
14. R Isomer
15. S Isomer
-continued
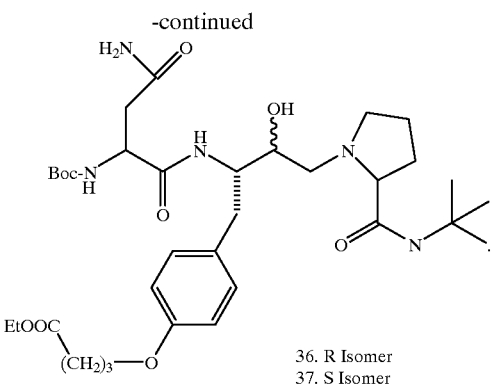
36. R Isomer
37. S Isomer
* * * * *